(12) United States Patent
Hall et al.

(10) Patent No.: US 11,045,620 B2
(45) Date of Patent: Jun. 29, 2021

(54) ELECTRODES FOR NITRIC OXIDE GENERATION

(71) Applicant: Third Pole, Inc., Waltham, MA (US)

(72) Inventors: Gregory W. Hall, Belmont, MA (US); Ian J. Gillerman, Somerville, MA (US); Sina Mohsenian, Billerica, MA (US); Aubrey Ortiz, Boston, MA (US); Christopher Miles, Acton, MA (US); Wolfgang Scholz, Beverly, MA (US); Adam J. Young, Dedham, MA (US); Benjamin Apollonio, Lunenburg, MA (US)

(73) Assignee: Third Pole, Inc., Waltham, MA (US)

( * ) Notice: Subject to any disclaimer, the term of this patent is extended or adjusted under 35 U.S.C. 154(b) by 0 days.

(21) Appl. No.: 16/875,687

(22) Filed: May 15, 2020

(65) Prior Publication Data
US 2020/0360649 A1    Nov. 19, 2020

Related U.S. Application Data

(60) Provisional application No. 62/959,942, filed on Jan. 11, 2020, provisional application No. 62/959,933, (Continued)

(51) Int. Cl.
*A61M 16/12* (2006.01)
*A61K 33/00* (2006.01)
*A61M 16/00* (2006.01)

(52) U.S. Cl.
CPC ............ *A61M 16/12* (2013.01); *A61K 33/00* (2013.01); *A61M 16/024* (2017.08); *A61M 2202/0275* (2013.01); *A61M 2205/33* (2013.01)

(58) Field of Classification Search
CPC ................ A61M 16/12; A61M 16/024; A61M 2202/0275; A61M 2205/33;
(Continued)

(56) References Cited

U.S. PATENT DOCUMENTS

| 709,867 A | 9/1902 | Bradley et al. |
|---|---|---|
| 2,485,478 A | 10/1949 | Cotton |

(Continued)

FOREIGN PATENT DOCUMENTS

| CN | 1099997 | 3/1995 |
|---|---|---|
| CN | 1730115 | 2/2006 |

(Continued)

OTHER PUBLICATIONS

Charles, et al., "SiO2 Deposition from Oxygen/Silane Pulsed Helicon Diffusion Plasmas" Applied Physics Letters, Vol. 67, No. 1, pp. 40-42, Jul. 3, 1995.

(Continued)

*Primary Examiner* — Xiuyu Tai
(74) *Attorney, Agent, or Firm* — Greenberg Traurig, LLP; David J. Dykeman; Jaime L. Burke

(57) ABSTRACT

Systems and methods for nitric oxide (NO) generation systems are provided. In some embodiments, an NO generation system comprises at least one pair of electrodes configured to generate a product gas containing NO from a flow of a reactant gas. The electrodes have elongated surfaces such that a plasma produced is carried by the flow of the reactant gas and glides along the elongated surfaces from a first end towards a second end of the electrode pair. A controller is configured to regulate the amount of NO in the product gas by the at least one pair of electrodes using one or more parameters as an input to the controller. The one or more parameters include information from a plurality of sensors configured to collect information relating to at least (Continued)

one of the reactant gas, the product gas, and a medical gas into which the product gas flows.

18 Claims, 52 Drawing Sheets

Related U.S. Application Data filed on Jan. 11, 2020, provisional application No. 62/848,530, filed on May 15, 2019.

(58) Field of Classification Search
CPC ............ A61M 16/101; A61M 16/0093; A61M 16/202; A61M 16/0057; A61M 16/022; A61M 16/107; A61M 16/04; A61M 16/0666; A61M 2205/80; A61M 2016/0027; A61M 16/0078; A61M 2015/0033; A61M 2016/1035; A61M 2205/14; A61M 2205/3306; A61M 2205/3368; A61M 2205/7527; A61M 2205/6054; A61M 15/02; A61M 16/085; A61M 16/0051; A61M 16/0808; A61M 2205/7545; A61M 2205/18; A61M 2205/505; A61M 2016/1025; A61M 2202/0208; A61M 2205/6072; A61M 16/161; A61M 2205/3358; A61M 2205/3334; A61M 2205/6018; A61M 16/203; A61M 2205/3317; A61M 16/16; A61M 2205/125; A61M 2205/3584; A61M 2205/8206; A61M 2205/054; A61M 2202/0283; A61M 2205/502; A61M 2209/088; A61M 2205/05; A61M 2202/0007; A61M 2202/0057; A61K 33/00; A61K 9/0014; C01B 21/32; C01B 21/24; C01B 21/30; A61P 7/00; A61P 25/00; A61P 1/02; A61P 9/08; A61P 19/02; A61P 35/00; A61P 25/04; A61P 33/00; A61P 9/00; A61P 29/00; A61P 21/00; A61P 9/10; A61P 31/10; A61P 11/00; A61P 31/00; A61P 17/10; A61P 17/14; A61P 3/10; A61P 17/02; A61P 15/14; A61P 31/04; A61P 9/12; A61P 19/10; A61P 17/16; A61P 43/00; A61P 31/02; A61P 7/10; A61P 19/04; A61P 31/12; A61L 2202/11; A61L 2202/26; A61L 2/20; A61L 2/14; A61N 1/44; A61D 7/00; D06M 11/64; D06M 10/06; H05H 1/48; H05H 1/3405; H05H 1/0081; H05H 2001/3442; B01J 19/088; B01J 12/002; B01J 2219/083; B01J 2219/0824; B01J 2219/0875; B01J 2219/0869; B01J 2219/0809; B01J 7/00; B01D 53/00

See application file for complete search history.

(56) References Cited

U.S. PATENT DOCUMENTS

| | | | |
|---|---|---|---|
| 2,485,481 A | 10/1949 | Cotton | |
| 2,525,938 A | 10/1950 | Peck | |
| 2,684,448 A | 7/1954 | Nilles | |
| 3,225,309 A | 10/1965 | Phelps | |
| 4,287,040 A | 9/1981 | Alamaro | |
| 4,500,563 A | 2/1985 | Ellenberger et al. | |
| 4,505,795 A | 3/1985 | Alamaro | |
| 4,680,694 A | 7/1987 | Huynh et al. | |
| 4,695,358 A | 9/1987 | Mizuno et al. | |
| 4,705,670 A | 11/1987 | O'Hare | |
| 4,816,229 A | 3/1989 | Jensen et al. | |
| 4,877,589 A | 10/1989 | Conrad | |
| 5,285,372 A | 2/1994 | Huynh et al. | |
| 5,378,436 A | 1/1995 | Endoh et al. | |
| 5,396,882 A | 3/1995 | Zapol | |
| 5,471,977 A | 12/1995 | Olsson et al. | |
| 5,485,827 A | 1/1996 | Zapol et al. | |
| 5,531,218 A | 7/1996 | Krebs | |
| 5,546,935 A | 8/1996 | Champeau | |
| 5,558,083 A | 9/1996 | Bathe et al. | |
| 5,573,733 A | 11/1996 | Salama | |
| 5,674,381 A | 10/1997 | Dekker | |
| 5,692,495 A | 12/1997 | Sheu | |
| 5,732,693 A | 3/1998 | Bathe et al. | |
| 5,749,937 A | 5/1998 | Detering et al. | |
| 5,752,504 A | 5/1998 | Bathe | |
| 5,827,420 A | 10/1998 | Shirazi et al. | |
| 5,839,433 A | 11/1998 | Higenbottam | |
| 5,845,633 A | 12/1998 | Psaros | |
| 6,089,229 A | 7/2000 | Bathe et al. | |
| 6,109,260 A | 8/2000 | Bathe | |
| 6,125,846 A | 10/2000 | Bathe et al. | |
| 6,164,276 A | 12/2000 | Bathe et al. | |
| 6,186,140 B1 | 2/2001 | Hoague | |
| 6,197,091 B1 | 3/2001 | Ji et al. | |
| 6,224,653 B1 | 5/2001 | Shvedchikov et al. | |
| 6,250,302 B1 | 6/2001 | Rantala | |
| 6,296,827 B1 | 10/2001 | Castor et al. | |
| 6,432,077 B1 | 8/2002 | Stenzler | |
| 6,532,956 B2 | 3/2003 | Hill | |
| 6,536,429 B1 | 3/2003 | Pavlov et al. | |
| 6,581,599 B1 | 6/2003 | Stenzler | |
| 6,668,828 B1 | 12/2003 | Figley et al. | |
| 6,758,214 B2 | 7/2004 | Fine et al. | |
| 6,920,876 B2 | 7/2005 | Miller et al. | |
| 6,955,171 B1 | 10/2005 | Figley et al. | |
| 6,955,790 B2 | 10/2005 | Castor et al. | |
| 6,984,256 B2 | 1/2006 | Lamprecht et al. | |
| 6,986,351 B2 | 1/2006 | Figley et al. | |
| 7,025,869 B2 | 4/2006 | Fine et al. | |
| 7,040,313 B2 | 5/2006 | Fine et al. | |
| 7,122,018 B2 | 10/2006 | Stenzler et al. | |
| 7,220,393 B2 | 5/2007 | Miller et al. | |
| 7,255,105 B2 | 8/2007 | Figley et al. | |
| 7,312,584 B2 | 12/2007 | Tamita et al. | |
| 7,335,181 B2 | 2/2008 | Miller et al. | |
| 7,520,866 B2 | 1/2009 | Stenzler et al. | |
| 7,485,324 B2 | 2/2009 | Miller et al. | |
| 7,498,000 B2 | 3/2009 | Pekshev et al. | |
| 7,516,742 B2 | 4/2009 | Stenzler et al. | |
| 7,523,752 B2 | 4/2009 | Montgomery et al. | |
| 7,531,133 B2 | 5/2009 | Hole et al. | |
| 7,560,076 B2 | 7/2009 | Rounbehler et al. | |
| 7,589,473 B2 | 9/2009 | Suslov | |
| 7,597,731 B2 | 10/2009 | Palmerton et al. | |
| 7,618,594 B2 | 11/2009 | Rounbehler et al. | |
| 7,744,812 B2 | 6/2010 | Witherspoon et al. | |
| 7,861,516 B2 | 1/2011 | Allanson et al. | |
| 7,861,717 B1 | 1/2011 | Krebs | |
| 7,914,743 B2 | 3/2011 | Fine et al. | |
| 7,947,227 B2 | 5/2011 | Fine et al. | |
| 7,955,294 B2 | 6/2011 | Stenzler et al. | |
| 8,030,849 B2 | 10/2011 | Suslov | |
| 8,043,252 B2 | 10/2011 | Miller et al. | |
| 8,057,742 B2 | 11/2011 | Rounbehler et al. | |
| 8,066,904 B2 | 11/2011 | Fine et al. | |
| 8,079,998 B2 | 12/2011 | Hole et al. | |
| 8,083,997 B2 | 12/2011 | Rounbehler et al. | |
| 8,091,549 B2 | 1/2012 | Montgomery et al. | |
| 8,151,791 B2 | 4/2012 | Arlow et al. | |
| 8,173,072 B2 | 5/2012 | Fine et al. | |
| 8,187,544 B2 | 5/2012 | Fine et al. | |
| 8,211,368 B2 | 7/2012 | Fine et al. | |
| 8,221,800 B2 | 7/2012 | Fine et al. | |
| 8,226,916 B2 | 7/2012 | Rounbehler et al. | |
| 8,246,725 B2 | 8/2012 | Rounbehler et al. | |
| 8,268,252 B2 | 9/2012 | Fuller et al. | |
| 8,282,966 B2 | 10/2012 | Baldassarre et al. | |
| 8,291,904 B2 | 10/2012 | Bathe et al. | |

(56) References Cited

U.S. PATENT DOCUMENTS

| | | |
|---|---|---|
| 8,293,284 B2 | 10/2012 | Baldassarre et al. |
| 8,344,627 B1 | 1/2013 | Hooke et al. |
| 8,371,296 B2 | 2/2013 | Fine et al. |
| 8,377,462 B2 | 2/2013 | DesNoyer et al. |
| 8,397,721 B2 | 3/2013 | Montgomery et al. |
| D679,366 S | 4/2013 | Fuller |
| 8,408,206 B2 | 4/2013 | Montgomery et al. |
| 8,431,163 B2 | 4/2013 | Baldassarre et al. |
| D688,352 S | 8/2013 | Fuller |
| 8,517,015 B2 | 8/2013 | Montgomery et al. |
| 8,518,457 B2 | 8/2013 | Miller et al. |
| 8,573,209 B2 | 11/2013 | Bathe et al. |
| 8,573,210 B2 | 11/2013 | Bathe et al. |
| 8,574,531 B2 | 11/2013 | Miller et al. |
| 8,580,109 B2 | 11/2013 | Kruckenberg et al. |
| 8,607,785 B2 | 12/2013 | Fine et al. |
| 8,607,792 B2 | 12/2013 | Montgomery et al. |
| 8,609,026 B2 | 12/2013 | Fine et al. |
| 8,609,028 B2 | 12/2013 | Rounbehler et al. |
| 8,613,958 B2 | 12/2013 | Fine |
| 8,616,204 B2 | 12/2013 | Montgomery et al. |
| 8,646,445 B2 | 2/2014 | Fine et al. |
| D701,963 S | 4/2014 | Abarbanel et al. |
| 8,685,467 B2 | 4/2014 | Miller et al. |
| 8,701,657 B2 | 4/2014 | Fine et al. |
| 8,715,577 B2 | 5/2014 | Fine et al. |
| 8,717,733 B2 | 5/2014 | Gefter et al. |
| 8,720,440 B2 | 5/2014 | Montgomery et al. |
| 8,741,222 B2 | 6/2014 | Fine et al. |
| 8,757,148 B2 | 6/2014 | Montgomery et al. |
| 8,770,199 B2 | 7/2014 | Flanagan et al. |
| 8,776,794 B2 | 7/2014 | Bathe et al. |
| 8,776,795 B2 | 7/2014 | Bathe et al. |
| 8,790,715 B2 | 7/2014 | Montgomery et al. |
| 8,795,222 B2 | 8/2014 | Stenzler et al. |
| 8,795,741 B2 | 8/2014 | Baldassarre |
| 8,808,655 B2 | 8/2014 | Solovyov et al. |
| 8,821,801 B2 | 9/2014 | Rounbehler et al. |
| 8,821,828 B2 | 9/2014 | Hilbig et al. |
| 8,846,112 B2 | 9/2014 | Baldassarre |
| 8,887,720 B2 | 11/2014 | Fine et al. |
| 8,893,717 B2 | 11/2014 | Montgomery et al. |
| 8,944,049 B2 | 2/2015 | Fine et al. |
| 9,095,534 B2 | 8/2015 | Stenzler et al. |
| 9,108,016 B2 | 8/2015 | Acker et al. |
| 9,180,217 B2 | 11/2015 | Arnold et al. |
| 9,192,718 B2 | 11/2015 | Fine |
| 9,265,911 B2 | 2/2016 | Bathe et al. |
| 9,279,794 B2 | 3/2016 | Tolmie et al. |
| 9,295,802 B2 | 3/2016 | Bathe et al. |
| 9,351,994 B2 | 5/2016 | Montgomery et al. |
| 9,408,994 B2 | 5/2016 | Fine et al. |
| 9,408,993 B2 | 8/2016 | Bathe et al. |
| 9,522,249 B2 | 12/2016 | Rounbehler et al. |
| 9,550,039 B2 | 1/2017 | Flanagan et al. |
| 9,550,040 B2 | 1/2017 | Acker et al. |
| 9,573,110 B2 | 2/2017 | Montgomery et al. |
| 9,604,028 B2 | 3/2017 | Fine et al. |
| 9,701,538 B2 | 7/2017 | Fine et al. |
| 9,713,244 B2 | 7/2017 | Tabata et al. |
| 9,770,570 B2 | 9/2017 | Schnictman et al. |
| 9,795,756 B2 | 10/2017 | Flanagan et al. |
| 9,895,199 B2 | 2/2018 | Montgomery et al. |
| 9,896,337 B2 | 2/2018 | Montgomery et al. |
| 9,956,373 B2 | 5/2018 | Rounbehler et al. |
| 9,982,354 B2 | 5/2018 | Kim |
| 10,081,544 B2 | 9/2018 | Fine et al. |
| 10,086,352 B2 | 10/2018 | Fine et al. |
| 10,099,029 B2 | 10/2018 | Montgomery et al. |
| 10,124,142 B2 | 11/2018 | Rounbehler et al. |
| 10,179,222 B2 | 1/2019 | Fine et al. |
| 10,213,572 B2 | 2/2019 | Gellman et al. |
| 10,239,038 B2 | 3/2019 | Zapol et al. |
| 10,279,139 B2 | 5/2019 | Zapol et al. |
| 10,286,176 B2 | 5/2019 | Zapol et al. |
| 10,293,133 B2 | 5/2019 | Zapol et al. |
| 10,328,228 B2 | 6/2019 | Zapol et al. |
| 10,398,820 B2 | 9/2019 | Potenziano et al. |
| 10,426,913 B2 | 10/2019 | Tolmie et al. |
| 10,434,276 B2 | 10/2019 | Zapol et al. |
| 10,532,176 B2 | 1/2020 | Zapol et al. |
| 10,548,920 B2 | 2/2020 | Montgomery et al. |
| 10,556,082 B2 | 2/2020 | Flanagan et al. |
| 10,556,086 B2 | 2/2020 | Goldstein et al. |
| 10,576,239 B2 | 3/2020 | Zapol et al. |
| 10,682,486 B1 | 6/2020 | Moon et al. |
| 10,695,523 B2 | 6/2020 | Zapol et al. |
| 10,737,051 B2 | 8/2020 | Gellman et al. |
| 10,758,703 B2 | 9/2020 | Kohlmann et al. |
| 10,773,046 B2 | 9/2020 | Schnitman et al. |
| 10,780,241 B2 | 9/2020 | Fine et al. |
| 10,814,092 B2 | 10/2020 | Rounbehler et al. |
| 10,946,163 B2 | 3/2021 | Gillerman et al. |
| 2001/0031230 A1 | 10/2001 | Castor et al. |
| 2001/0035186 A1 | 11/2001 | Hill |
| 2002/0185126 A1 | 12/2002 | Krebs |
| 2004/0019274 A1 | 1/2004 | Galloway, Jr. et al. |
| 2004/0028753 A1 | 2/2004 | Hedenstierna et al. |
| 2004/0031248 A1 | 2/2004 | Lindsay |
| 2004/0181149 A1 | 9/2004 | Langlotz et al. |
| 2005/0172971 A1 | 8/2005 | Kolobow et al. |
| 2005/0218007 A1 | 10/2005 | Pekshev et al. |
| 2005/0263150 A1 | 12/2005 | Chathampally et al. |
| 2005/0281465 A1 | 12/2005 | Marquart et al. |
| 2006/0025700 A1 | 2/2006 | Fallik |
| 2006/0172018 A1 | 8/2006 | Fine et al. |
| 2006/0207594 A1 | 9/2006 | Stenzler et al. |
| 2006/0276844 A1 | 12/2006 | Alon et al. |
| 2007/0151561 A1 | 7/2007 | Laurila |
| 2007/0181126 A1 | 8/2007 | Tolmie et al. |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0135044 A1 | 6/2008 | Freitag et al. |
| 2008/0176335 A1 | 7/2008 | Alberti et al. |
| 2008/0202509 A1 | 8/2008 | Dillon et al. |
| 2010/0030091 A1 | 2/2010 | Fine |
| 2010/0043789 A1 | 2/2010 | Fine et al. |
| 2010/0089392 A1 | 4/2010 | Fine et al. |
| 2010/0189808 A1 | 7/2010 | Gupta et al. |
| 2010/0275911 A1 | 11/2010 | Arlow et al. |
| 2010/0330193 A1 | 12/2010 | Baldassarre et al. |
| 2011/0140607 A1 | 6/2011 | Moore et al. |
| 2011/0240019 A1 | 10/2011 | Fine et al. |
| 2012/0093948 A1 | 4/2012 | Fine et al. |
| 2012/0279500 A1 | 11/2012 | Singvogel et al. |
| 2012/0285449 A1 | 11/2012 | Fine et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2013/0239963 A1 | 9/2013 | Goldstein et al. |
| 2013/0309328 A1 | 11/2013 | Watts et al. |
| 2014/0020685 A1 | 1/2014 | Szabo |
| 2014/0031668 A1 | 1/2014 | Mobasser et al. |
| 2014/0127081 A1 | 5/2014 | Fine et al. |
| 2014/0127330 A1 | 5/2014 | Fine et al. |
| 2014/0144436 A1 | 5/2014 | Fine et al. |
| 2014/0144444 A1 | 5/2014 | Fine et al. |
| 2014/0158121 A1 | 6/2014 | Flanagan et al. |
| 2014/0166009 A1 | 6/2014 | Flanagan et al. |
| 2014/0216452 A1 | 8/2014 | Miller et al. |
| 2014/0251787 A1 | 9/2014 | Montgomery et al. |
| 2014/0363525 A1 | 12/2014 | Montgomery et al. |
| 2014/0377378 A1 | 12/2014 | Baldassarre |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0090261 A1 | 4/2015 | Crosbie |
| 2015/0101604 A1 | 4/2015 | Crosbie |
| 2015/0174158 A1 | 6/2015 | Av-Gay et al. |
| 2015/0272988 A1 | 10/2015 | Av-Gay et al. |
| 2015/0328430 A1 | 11/2015 | Miller et al. |

(56) References Cited

U.S. PATENT DOCUMENTS

| | | |
|---|---|---|
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0106949 A1 | 4/2016 | Kohlmann et al. |
| 2016/0121071 A1 | 5/2016 | Moon et al. |
| 2016/0151598 A1 | 6/2016 | Fine |
| 2016/0183841 A1 | 6/2016 | Duindam et al. |
| 2016/0191887 A1 | 6/2016 | Casas |
| 2016/0228670 A1 | 8/2016 | Av-Gay et al. |
| 2016/0243328 A1 | 8/2016 | Tolmie et al. |
| 2016/0271169 A1 | 9/2016 | Potenziano et al. |
| 2016/0279165 A1 | 9/2016 | Av-Gay et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0112871 A1* | 4/2017 | Nelson ............... A61P 7/00 |
| 2017/0128694 A1 | 5/2017 | Acker et al. |
| 2017/0143758 A1 | 5/2017 | Greenberg et al. |
| 2017/0165294 A1 | 6/2017 | Dasse et al. |
| 2017/0182088 A1 | 6/2017 | Dasse et al. |
| 2017/0232166 A1 | 8/2017 | Potenziano et al. |
| 2017/0239289 A1 | 8/2017 | Av-Gay et al. |
| 2017/0259025 A1 | 9/2017 | Fine et al. |
| 2018/0049622 A1 | 2/2018 | Ryan et al. |
| 2018/0104432 A1 | 4/2018 | Flanagan et al. |
| 2018/0125883 A1 | 5/2018 | Av-Gay et al. |
| 2018/0126111 A1 | 5/2018 | Moon et al. |
| 2018/0133246 A1 | 5/2018 | Av-Gay et al. |
| 2018/0169370 A1 | 6/2018 | Montgomery et al. |
| 2018/0243527 A1 | 8/2018 | Zapol et al. |
| 2018/0243528 A1 | 8/2018 | Zapol et al. |
| 2018/0280920 A1 | 10/2018 | Zapol et al. |
| 2018/0296790 A1 | 10/2018 | Zapol et al. |
| 2018/0311460 A1 | 11/2018 | Rounbehler et al. |
| 2019/0038864 A1 | 2/2019 | Montgomery et al. |
| 2019/0092639 A1 | 3/2019 | Fine et al. |
| 2019/0127223 A1 | 5/2019 | Montgomery et al. |
| 2019/0135633 A1 | 5/2019 | Montgomery et al. |
| 2019/0143068 A1 | 5/2019 | Rounbehler et al. |
| 2019/0209993 A1 | 7/2019 | Fine et al. |
| 2019/0217042 A1 | 7/2019 | Zapol et al. |
| 2019/0217043 A1 | 7/2019 | Fine et al. |
| 2019/0233288 A1 | 8/2019 | Montgomery et al. |
| 2019/0233289 A1 | 8/2019 | Montgomery et al. |
| 2019/0276313 A1 | 9/2019 | Montgomery et al. |
| 2019/0314596 A1 | 10/2019 | Zapol et al. |
| 2019/0374739 A1 | 12/2019 | Tolmie et al. |
| 2020/0094011 A1 | 3/2020 | Zapol et al. |
| 2020/0139071 A1 | 5/2020 | Fine et al. |
| 2020/0139072 A1 | 5/2020 | Zapol et al. |
| 2020/0139073 A1 | 5/2020 | Tector et al. |
| 2020/0163989 A1 | 5/2020 | Montgomery et al. |
| 2020/0171259 A1 | 6/2020 | Flanagan et al. |
| 2020/0171264 A1 | 6/2020 | Goldstein et al. |
| 2020/0180958 A1 | 6/2020 | Fine et al. |
| 2020/0282375 A1 | 9/2020 | Fine et al. |
| 2020/0361772 A1 | 11/2020 | Hall et al. |
| 2020/0361773 A1 | 11/2020 | Gillerman et al. |
| 2020/0390994 A1 | 12/2020 | Gillerman et al. |

FOREIGN PATENT DOCUMENTS

| | | |
|---|---|---|
| CN | 201037113 Y | 3/2008 |
| CN | 100404083 C | 7/2008 |
| CN | 101036482 B | 12/2010 |
| CN | 110872714 A | 3/2020 |
| DE | 101 51 270 | 10/2006 |
| EP | 621051 | 10/1994 |
| EP | 0763500 A2 | 3/1997 |
| EP | 1036758 | 9/2000 |
| EP | 2151554 | 2/2010 |
| EP | 1854494 | 6/2012 |
| JP | H04132560 | 5/1992 |
| JP | 2000102616 | 4/2000 |
| JP | 2004065636 | 3/2004 |
| JP | 2006273677 | 10/2006 |
| KR | 20100087977 | 8/2010 |
| RU | 2199167 C1 | 2/2003 |
| WO | WO199507610 | 3/1995 |
| WO | WO2004032719 | 4/2004 |
| WO | 2005110441 A2 | 11/2005 |
| WO | WO2009018837 | 2/2009 |
| WO | WO2010021944 | 2/2010 |
| WO | WO2011/002606 | 1/2011 |
| WO | WO2012/034089 | 3/2012 |
| WO | WO2012/094008 | 7/2012 |
| WO | WO2013/052548 | 4/2013 |
| WO | WO2013/070712 | 5/2013 |
| WO | WO2013/181179 | 12/2013 |
| WO | WO2014/085719 | 6/2014 |
| WO | WO2014/143842 | 9/2014 |
| WO | WO2014/144151 | 9/2014 |
| WO | WO2015/066278 | 5/2015 |
| WO | WO2015/127085 | 8/2015 |
| WO | WO2016/064863 | 4/2016 |
| WO | WO2018/157172 | 8/2018 |
| WO | WO2018/157175 | 8/2018 |
| WO | 2019046415 A1 | 3/2019 |
| WO | WO2019/046413 | 3/2019 |
| WO | WO2019/133776 | 7/2019 |
| WO | WO2019/133777 | 7/2019 |
| WO | 2019222640 A1 | 11/2019 |
| WO | 2020033768 A1 | 2/2020 |
| WO | 2020142658 A1 | 7/2020 |
| WO | 2020150195 A1 | 7/2020 |
| WO | 2020232414 A1 | 11/2020 |
| WO | 2020232419 A1 | 11/2020 |

OTHER PUBLICATIONS

Patil et al., Plasma Assisted Nitrogen Oxide Production from Air, AIChE Journal, vol. 64, Issue 2, Aug. 14, 2017.
Pawlat et al., Evaluation of Oxidative Species in Gaseous, Plasma Chemistry and Plasma Processing, vol. 39, pp. 627-642, Mar. 28, 2019.
Wang et al., Gliding Arc Plasma for CO2 Conversion, Chemical Engineering Journal, vol. 330, pp. 11-25, 2017.
International Search Report in PCT/US2020/033245 dated Sep. 21, 2020.
Arjunan Thesis—Plasma Produced Reactive Oxygen and Nitrogen Species in Angiogenesis—May, 2011—Krishna Priya Arjunan.
Arora et al., Nitric Oxide Regulation of Bacterial Biofilms, Biochemistry, vol. 54, pp. 3717-3728, May 21, 2015.
Barraud et al., Involvement of Nitric Oxide n Biofilm Dispersal of Pseudomonas Aeruginosa, Journal of Bacteriology, vol. 188, No. 21, pp. 7344-7353, Nov. 2006.
Bentur et al., Pilot Study to Test Inhaled Nitric Oxide in Cystic Fibrosis Patients with Refractory *Mycobacterium abscessus* Lung Infection, Journal of Cystic Fibrosis, vol. 19, pp. 225-231, May 23, 2019.
Bogdonovski et al., Anti-Mycobacterial Activity of High-Dose Nitric Oxide Against *Mycobacterium abscessus* In Vitro, National Institutes of Health Poster, Jul. 8, 2018.
Deppisch et al., Gaseous Nitric Oxide to Treat Antibiotic Resistant Bacterial and Fungal Lung Infections in Patients with Cystic Fibrosis: A Phase I Clinical Study, Infection, vol. 44, pp. 513-520, Feb. 9, 2016.
Dobrynin et al., "Direct and Controllable Nitric Oxide Delivery into Biological Media and Living Cells by a Pin-to-Hole Spark Discharge (PHD) Plasma" Journal of Physics D: Applied Physics, vol. 44, pp. 1-10, Jan. 28, 2011.
Howlin et al., Low-Dose Nitric Oxide as Targeted Anti-Biofilm Adjunctive Therapy to Treat Chronic Pseudomonas Aeruginosa Infection in Cystic Fibrosis, Molecular Therapy, vol. 25, No. 9, pp. 2104-2116, Sep. 2017.

(56) References Cited

OTHER PUBLICATIONS

Hu et al., "Study on Production of Inhaled Nitric Oxide for Medical Applications by Pulsed Discharge" IEEE Transactions on Plasma Science, vol. 35, No. 3, pp. 619-625, Jun. 2007.
Kuo, Spencer P. "Air Plasma for Medical Applications" J. Biomedical Science and Engineering, vol. 5, pp. 481-495, Sep. 2012.
McMullin et al., The Antimicrobial Effect of Nitric Oxide on the Bacteria That Cause Nosocomial Pneumonia in Mechanically Ventilated Patients in the Intensive Care Unit, Respiratory Care, vol. 50, No. 11, pp. 1451-1456, Nov. 2005.
Miller et al., Gaseous Nitric Oxide Bactericidal Activity Retained During Intermittent High-Dose Short Duration Exposure, Nitric Oxide, vol. 20, Issue 1, pp. 16-23, Feb. 2009.
Miller et al., Inhaled Nitric Oxide Decreases the Bacterial Load in a Rat Model of Pseudomonas Aeruginosa Pneumonia, Journal of Cystic Fibrosis, vol. 12, pp. 817-820, Mar. 6, 2013.
Miller et al., Nitric Oxide is a Potential Antimicrobial Against Slow and Fast Growing Mycobacteria, Online Abstracts Issue, American Journal Respiratory Care Medicine, vol. 193, A7498, May 18, 2016.
Miller et al., A Phase I Clinical Study of Inhaled Nitric Oxide in Healthy Adults, Journal of Cystic Fibrosis, vol. 11, pp. 324-331, Apr. 18, 2012.
Namihira et al., "Temperature and Nitric Oxide Generation in a Pulsed Arc Discharge Plasma" Plasma Science and Technology, vol. 9, No. 6, pp. 747-751, Dec. 2007.
Navarro-Gonzalez et al., "The Physical Mechanism of Nitric Oxide Formation in Simulated Lightning" Geophysical Research Letters, vol. 28, No. 20, pp. 3867-3870, Oct. 15, 2001.
Olivier et al., Treatment of Refractory *Mycobacterium abscessus* Lung Infection with Inhaled Intermittent Nitric Oxide, Poster, Jul. 8, 2018.
Sakai et al., "Nitric Oxide Generator Based on Pulsed Arc Discharge" Acta Physica Polonica A, vol. 115, No. 6, pp. 1104-1106, Jun. 2009.
Tal et al., Nitric Oxide Inhalations in Bronchiolitis: A Pilot, Randomized, Double-Blinded, Controlled Trial, Pediatric Pulmonology, vol. 53, Issue 1, pp. 95-102, Jan. 2018.
Yaacoby-Bianu et al., Compassionate Nitric Oxide Adjuvant Treatment of Persistent *Mycobacterium* Infection in Cystic Fibrosis Patients, The Pediatric Infectious Disease Journal, vol. 37, No. 4, Apr. 2018.
Bellerophon, "A Dose Escalation Study to Assess the Safety and Efficacy of Pulsed iNO in Subjects With Pulmonary Fibrosis", Aug. 30, 2017, https://clinicaltrials.gov/ct2/show/NCT03267108.
Fowler, "Exercise Intolerance in Pulmonary Arterial Hypertension", Pulmonary Medicine, vol. 2012, Article ID 39204, 11 pages, (2012).
Keshav, Saurabh. "Using Plasmas for High-speed Flow Control and Combustion Control" Diss. The Ohio State University, 2008.
Li et al., Production of Medically Useful Nitric Monoxide Using AC Arc Discharge, Nitric Oxide, Feb. 28, 2018, vol. 73, pp. 89-95.
Mok et al. "Application of Positive Pulsed Corona Discharge to Removal of SO2 and NOx," Proceedings, ICESP VII, Sep. 20-25, 1998, Kyongiu, Korea.
Namihara et al., Production of Nitric Oxide Using a Pulsed Arc Discharge, IEEE Transactions on Plasma Science, 2002, 30(5):1993-1998.
Namihara et al., Production of Nitric Monoxide Using Pulsed Discharges for a Medical Application, IEEE Transactions on Plasma Science, vol. 29, No. 1, pp. 109-114, Feb. 2000.
Schilz, "Treatment of Pulmonary Hypertension Related to Disorders of Hypoxia" Advances in Pulmonary Hypertension, vol. 4, No. 2, pp. 14-22, May 2005.
Birkeland, K., "On the Oxidation of Atmospheric Nitrogen in Electric Arcs", A Paper read before the Faraday Society on Monday, Jul. 2, 1906, Published on Jan. 1, 1906.
Feigerle, C., et al., "Multiphoton Ionization of Vibrationally Hot Nitric Oxide Produced in a Pulsed Supersonic Glow Discharge", Journal of Chemical Physics, vol. 90, Issue 6, pp. 2900-2908, Mar. 15, 1989.
Hu, Hui et al., "Study on Pulsed Arc Discharge Conditions on Production of Nitric Oxide for Medical Application", High Voltage Apparatus, Issue 3, Mar. 2005.
Hu, Hui et al., "Study on Production of Nitric Monoxide for Respiratory Distress by Pulsed Discharge", Proceedings of the CSEE, vol. 23, No. 2, Jan. 2005.
Hu, Hui et al., "The Effect of Flow Distribution on the Concentration of NO Produced by Pulsed Arc Discharge", Plasma Science and Technology, vol. 9, No. 6, pp. 766-769, Dec. 2007.
Johns Hopkins University—"American Chemical Journal vol. XXXV"—No. 4, Reports Chapter, pp. 358-368, Apr. 1906.
Kornev, J., et al., "Generation of Active Oxidant Species by Pulsed Dielectric Barrier Discharge in Water-Air Mixtures", Ozone: Science & Engineering, vol. 28, Issue 4, pp. 207-215, Jul. 2006.
Li, Z. et al., "Development of Miniature Pulsed Power Generator," 2005 IEEE Pulsed Power Conference, Monterey, CA, pp. 1053-1056, Jul. 2005.
Matsuo, K. et al., "Nitric Oxide Generated by Atmospheric Pressure Air Microplasma," 2009 IEEE Pulsed Power Conference, Washington, DC, Jun. 28-Jul. 2, 2009, pp. 999-1003, Jan. 19, 2010.
Namihara et al., "Production of NO Using Pulsed Arc Discharges and Its Medical Applications", Journal of Plasma and Fusion Research, vol. 79, No. 1 pp. 35-38, Jun. 25, 2002.
Namihara et al., "Production of Nitric Monoxide in Dry Air Using Pulsed Ddischarge," Digest of Technical Papers. 12th IEEE International Pulsed Power Conference. (Cat. No. 99CH36358), Monterey, CA, pp. 1313-1316 vol. 2, Aug. 6, 2002.
Overzet, et al. "Why and How to Pulse a Plasma"—slide show presentation, Oct. 1997.
Pontiga, F., et al., "Nitrogen Oxides Generation Induced by Negative Corona Discharge in N2+O2 Mixtures," 2006 IEEE Conference on Electrical Insulation and Dielectric Phenomena, Kansas City, MO, pp. 264-267, Oct. 2006.
Sakai, et al., "A Compact Nitric Oxide Supply for Medical Application," 2007 16th IEEE International Pulsed Power Conference, Albuquerque, NM, pp. 752-755, Oct. 14, 2008.
Heli, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages (Includes English Language Translation of Title Page and Abstract).
Hui, Research on the Production of Nitric Oxide by Pulsed Arc Discharge and the Curing of Respiratory Distress Instrument, Dissertation for Degree of Doctor of Philosophy in Engineering, Huazhong University of Science and Technology, China, Apr. 2005, 138 pages (Includes English Language Translation of Title Page and Abstract).

\* cited by examiner

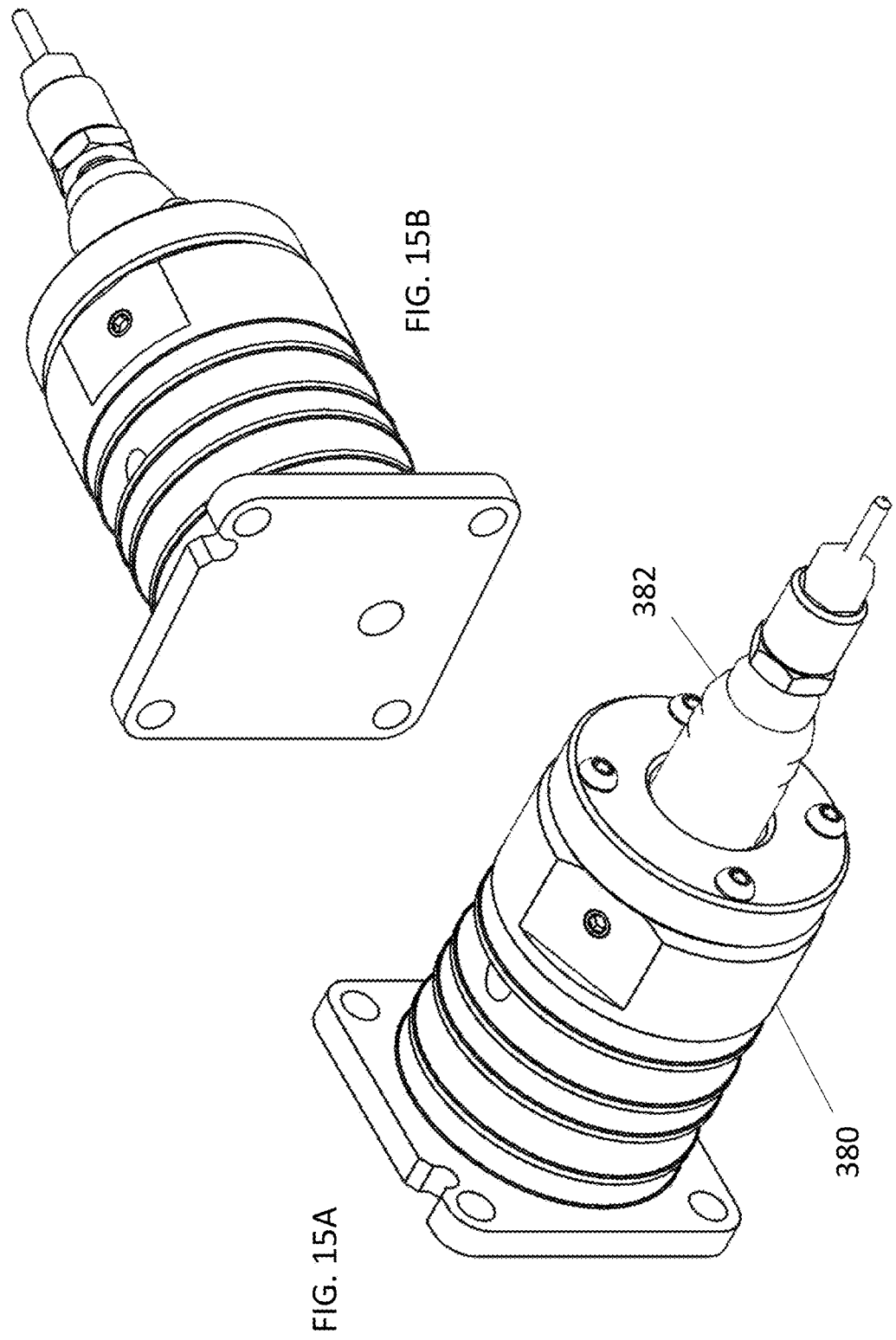

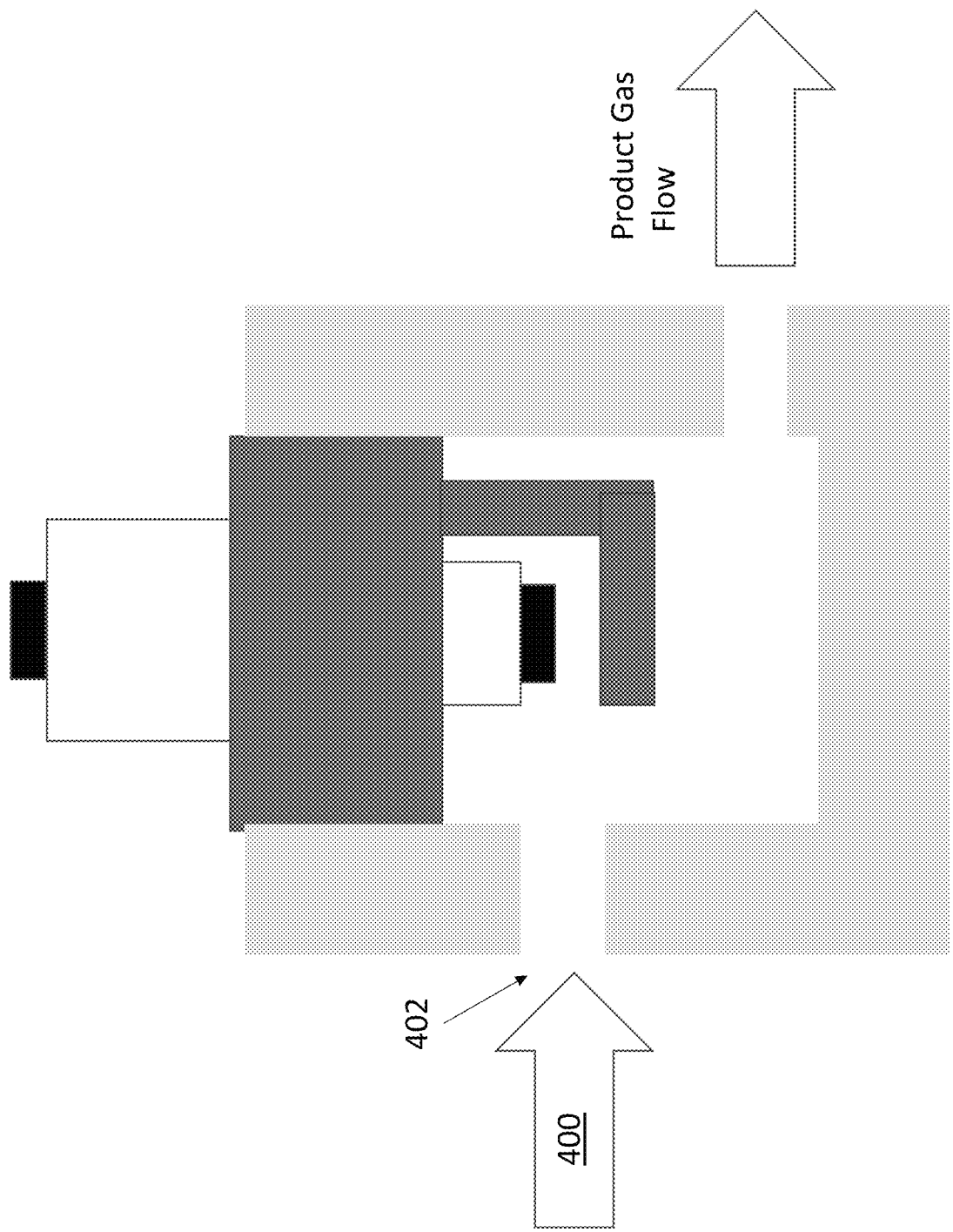

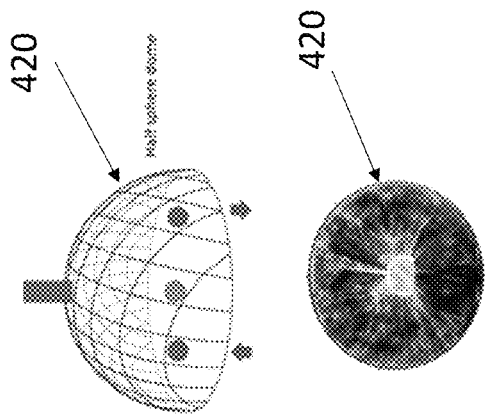
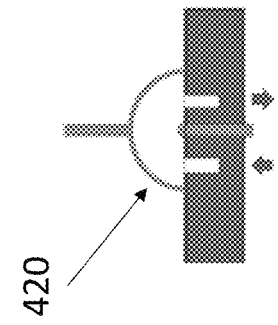
FIG. 17A  FIG. 17B  FIG. 17C

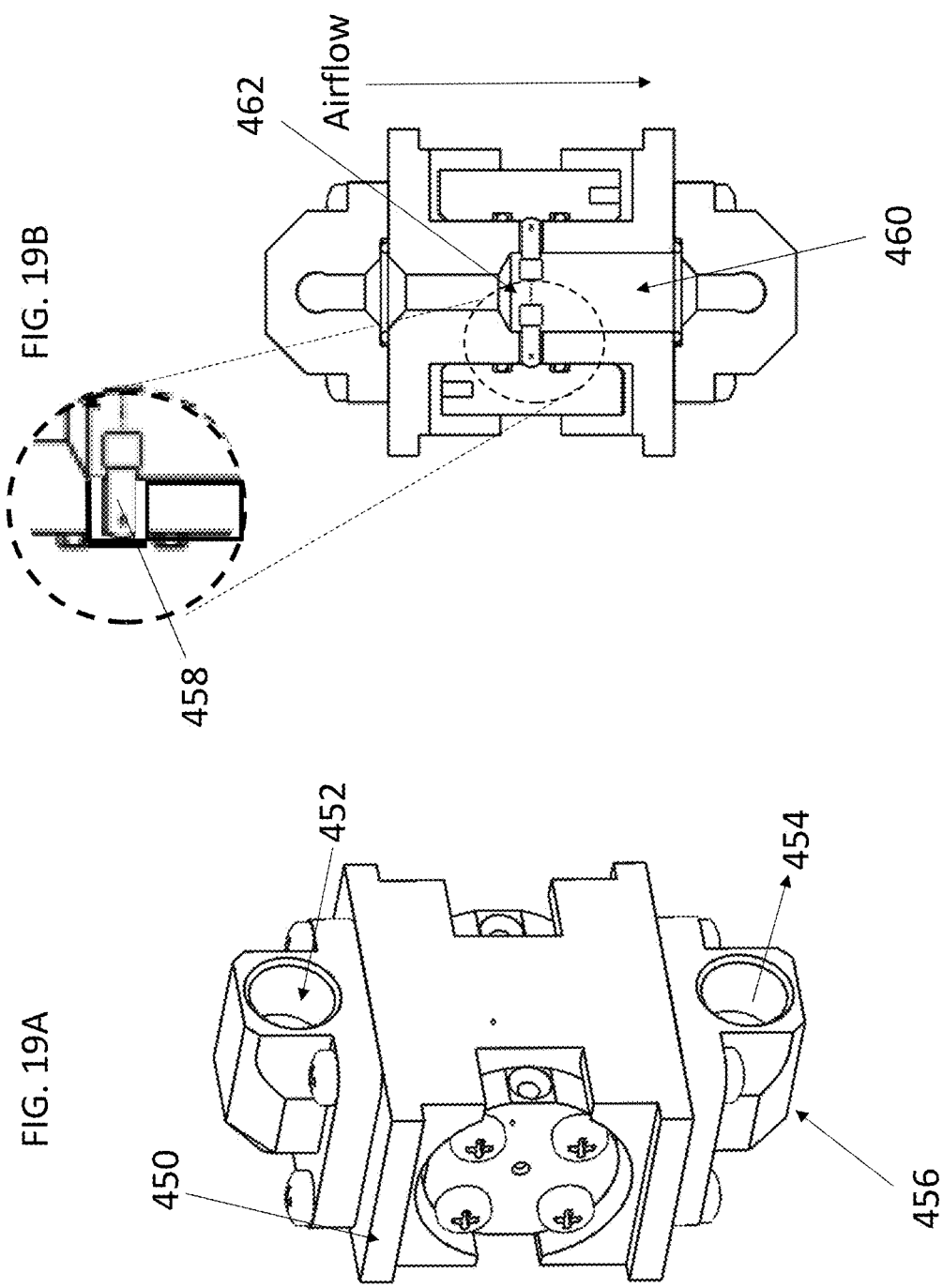

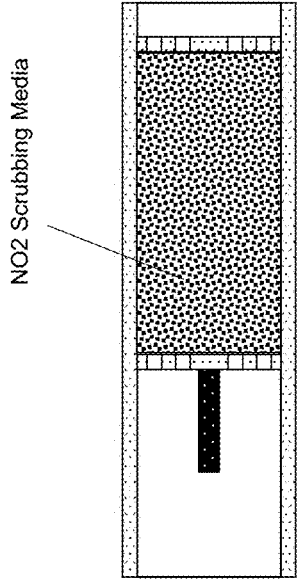
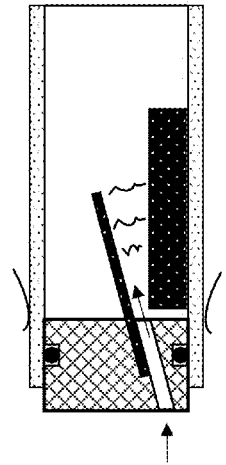
FIG. 46B
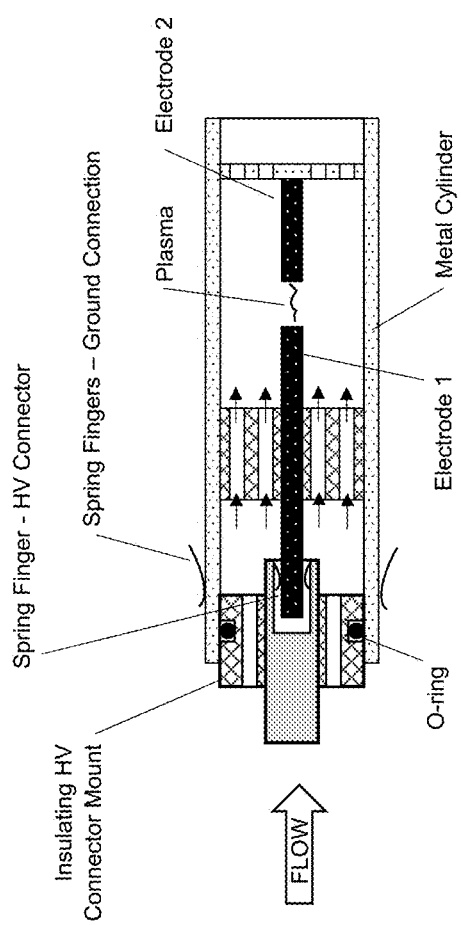
FIG. 46A
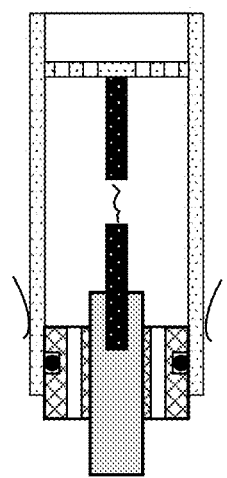
FIG. 46D
FIG. 46C

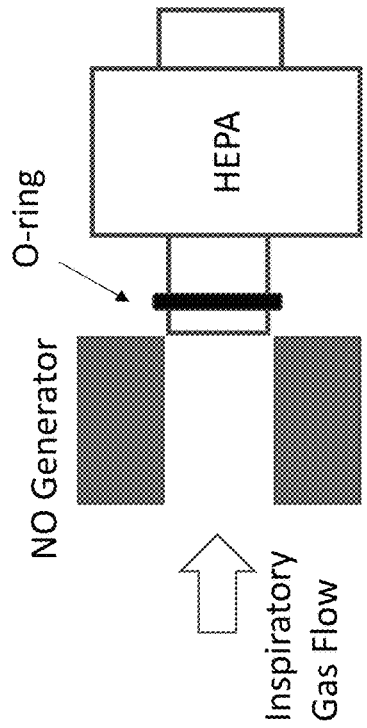
FIG. 47A
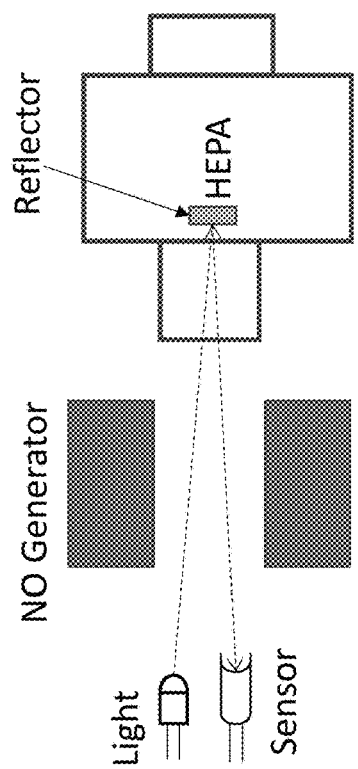
FIG. 47B
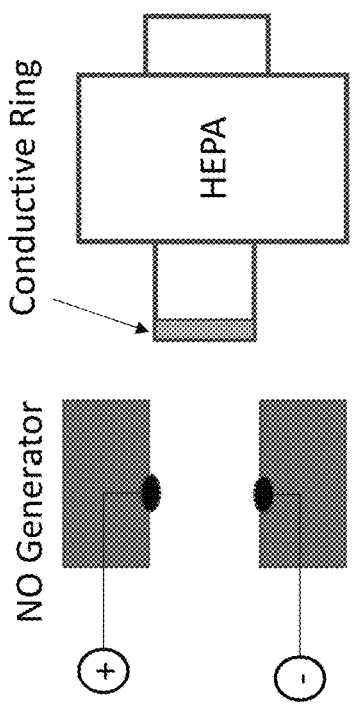
FIG. 47C
FIG. 47D

ELECTRODES FOR NITRIC OXIDE GENERATION

RELATED APPLICATIONS

This application claims the benefit of and priority to U.S. Provisional Application No. 62/959,942 filed Jan. 11, 2020, U.S. Provisional Application No. 62/959,933 filed Jan. 11, 2020, and U.S. Provisional Application No. 62/848,530 filed May 15, 2019, and the contents of each of these applications are hereby incorporated herein by reference in their entireties.

FEDERALLY SPONSORED RESEARCH OR DEVELOPMENT

This invention was made with government support under Grant No. R44 HL134429 and Grant No. R44 TR001704, awarded by the National Institutes of Health (NIH). The government has certain rights in the invention.

FIELD

The present disclosure relates to systems and methods for generating nitric oxide and various electrode designs associated therewith.

BACKGROUND

Nitric oxide has found to be useful in a number of ways for treatment of disease, particularly cardiac and respiratory ailments. Previous systems for producing NO and delivering the NO gas to a patient have a number of disadvantages. For example, tank-based systems required large tanks of NO gas at a high concentration and pressure. When treatment using this system is paused, NO in the circuit stalls and converts into $NO_2$, requiring the user to purge the manual ventilation circuit before resuming manual ventilation. Synthesizing NO from $NO_2$ or $N_2O_4$ requires the handling of toxic chemicals. Prior electric generation systems involve generating plasma in the main flow of air to be delivered to patients or pumped through a delivery tube.

SUMMARY

The present disclosure is directed to systems, methods and devices for nitric oxide generation for use with various ventilation and/or medical devices and having various electrode designs for generating the nitric oxide (NO).

In some embodiments, a nitric oxide (NO) generation system includes at least one pair of electrodes configured to generate a product gas containing NO from a flow of a reactant gas, the at least one pair of electrodes having a first end and second end with a length therebetween such that a plasma produced is carried by the flow of the reactant gas and glides along the length of the at least one pair of electrodes from the first end towards the second end; and a controller configured to regulate the amount of nitric oxide in the product gas produced by the at least one pair of electrodes using one or more parameters as an input to the controller, the one or more parameters including information from a plurality of sensors configured to collect information relating to at least one of the reactant gas, the product gas, and a medical gas into which the product gas flows. The pair of electrodes is formed from a material selected from the group consisting of hafnium, glassy carbon, iridium, rhodium, platinum, graphite, carbon-carbon composite, steel, stainless steel, titanium, copper, nickel, tungsten-silver alloy, tungsten, and alloys thereof. In some embodiments, more than one material is used to form at least one of the electrodes in the at least one pair of electrodes along an edge thereof.

In some embodiments, the electrodes in the at least pair of electrodes diverge from one another such that the electrodes move away from each along their length from the first end to the second end. In some embodiments, the diverging electrodes form a gap at the first end in a range of about 0.05 mm to about 10 mm. In some embodiments, the diverging electrodes form a gap at the second end in a range of about 1 mm to about 100 mm. In some embodiments, a distance the plasma glides along the length of the electrodes ranges from 1 mm to 200 mm.

In some embodiments, the nitric oxide (NO) generation further comprises a nozzle through which the reactant gas flows to the at least one pair of electrodes. In some embodiments, the nozzle ranges in diameter from about 0.1 to about 15 mm. In some embodiments, a cross-sectional area of the nozzle ranges from 0.03 $mm^2$ to 707 $mm^2$. In some embodiments, a cross-sectional area of the nozzle can be varied by the NO generation system. In some embodiments, the reactant gas flow along the electrode surfaces ranges in velocity from about 1 to about 100 m/second.

In some embodiments, a shape of an edge of the electrodes in the at least one electrode pair are configured to increase the length of an arc at a specific rate for a specific flow rate of reactant gas. In some embodiments, a shape of an edge of the electrodes in the at least one electrode pair is configured to increase the length of an arc at a specific rate for a specific reactant gas flow velocity.

In some embodiments, a nitric oxide (NO) generation system includes a plasma chamber comprising: at least one pair of electrodes configured to generate a product gas containing NO from a flow of a reactant gas. The at least one pair of electrodes have a first end and a second end and a length therebetween such that a plasma produced is carried by the flow of the reactant gas and glides along the length of the at least one pair of electrodes from the first end towards the second end of the at least one electrode pair. The system also includes at least one nozzle through which the reactant gas flows into the plasma chamber to the at least one pair of electrodes. A controller is configured to regulate the amount of nitric oxide in the product gas by the at least one pair of electrodes using one or more parameters as an input to the controller. The one or more parameters include information from a plurality of sensors configured to collect information relating to at least one of the reactant gas, the product gas, and a medical gas into which the product gas flows.

In some embodiments, a shape of an edge of the electrodes in the at least one electrode pair are configured to increase the length of an arc at a specific rate for a specific flow rate of reactant gas. In some embodiments, the at plasma chamber is formed from a material selected from the group consisting of a high temperature polymer, ceramic, metal, coated metal, and composite materials.

In some embodiments, the at least one nozzle comprises a first nozzle configured to supply reactant NO gas to the at least one pair of electrodes and a second nozzle configured to cool the plasma chamber. In some embodiments, the at least one nozzle comprises a first nozzle configure to supply reactant gas to the at least one pair of electrodes and a second nozzle configured to vary an interaction between the plasma and the reactant gas.

A method of generating nitric oxide includes ionizing a reactant gas inside one or more plasma chambers to generate a plasma for producing a product gas containing nitric oxide using a flow of the reactant gas through the one or more plasma chambers, the plasma chamber including at least one pair of electrodes for generating the product gas and having a first end and a second end and a length therebetween such that a plasma produced is carried by the flow of the reactant gas and glides along the length of the at least one pair of electrodes from the first end towards the second end; and controlling the amount of nitric oxide in the product gas using one or more parameters as input to a control algorithm used by one or more controllers to control the one or more plasma chambers, at least one of the one or more parameters being related to a target concentration of NO in an inspired gas, where the inspired gas is one of the product gas or a combination of the product gas and a medical gas into which the product gas flows.

In some embodiments, control outputs of the control algorithm include one or more of reactant gas flow rate, duty cycle, AC waveform, frequency current, voltage, and power.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 15A, FIG. 15B, FIG. 15C, FIG. 15D, FIG. 15E, FIG. 15F, FIG. 15G, and FIG. 15H illustrate an embodiment of a removable plasma chamber;

FIG. 16A and FIG. 16B illustrate embodiments of a plasma chamber that is aligned with a plasma chamber entry point;

FIG. 17A, FIG. 17B, and FIG. 17C illustrate an embodiment of a plasma chamber in the form of a dome;

FIG. 19A, FIG. 19B, and FIG. 19C illustrate various views of an embodiment of an electrode design;

FIG. 46A, FIG. 46B, FIG. 46C, FIG. 46D, FIG. 46E, and FIG. 46F illustrate an embodiment of an electrode cartridge; and FIG. 47A, FIG. 47B, FIG. 47C, and FIG. 47D illustrate examples of pneumatic connections that can be used between the HEPA filter and ventilator cartridge and/or NO generator.

Figure 1:
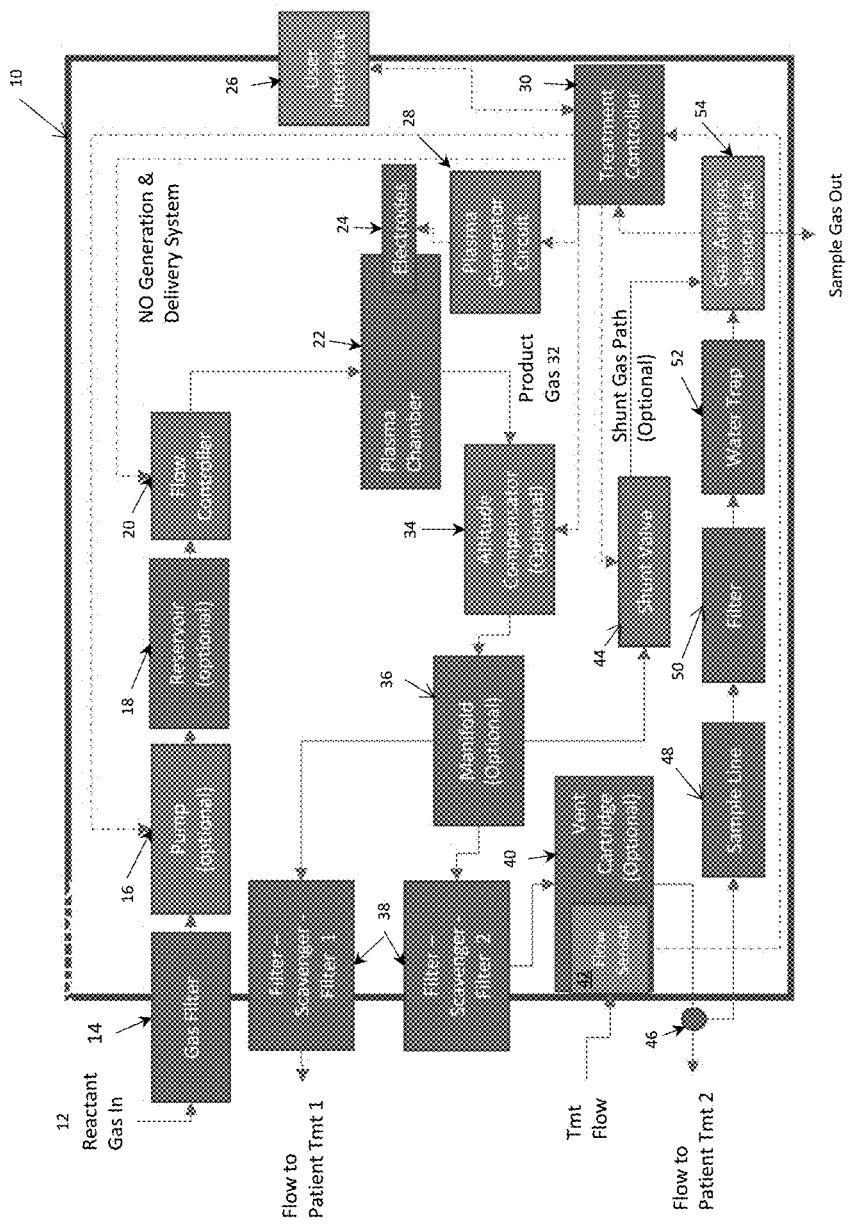
FIG. 1 is an exemplary embodiment of a system for generating an NO-enriched product gas.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure relates to systems and methods of nitric oxide (NO) delivery for use in various applications, for example, inside a hospital room, in an emergency room, in a doctor's office, in a clinic, and outside a hospital setting as a portable or ambulatory device. An NO generation and/or delivery system can take many forms, including but not limited to a device configured to work with an existing medical device that utilizes a product gas, a stand-alone (ambulatory) device, a module that can be integrated with an existing medical device, one or more types of cartridges that can perform various functions of the NO system, and an electronic NO tank. The NO generation system uses a reactant gas, including but not limited to ambient air, to produce a product gas that is enriched with NO.

An NO generation device can be used with any device that can utilize NO, including but not limited to a ventilator, an anesthesia device, a defibrillator, a ventricular assist device (VAD), a Continuous Positive Airway Pressure (CPAP) machine, a Bilevel Positive Airway Pressure (BiPAP) machine, a non-invasive positive pressure ventilator (NIPPV), a nasal cannula application, a nebulizer, an extracorporeal membrane oxygenation (ECMO), a bypass system, an automated CPR system, an oxygen delivery system, an oxygen concentrator, an oxygen generation system, and an automated external defibrillator AED, MRI, and a patient monitor. In addition, the destination for nitric oxide produced can be any type of delivery device associated with any medical device, including but not limited to a nasal cannula, a manual ventilation device, a face mask, inhaler, or any other delivery circuit. The NO generation capabilities can be integrated into any of these devices, or the devices can be used with an NO generation device as described herein.

FIG. 1 illustrates an exemplary embodiment of an NO generation system 10 that includes components for reactant gas intake 12 and delivery to a plasma chamber 22. The plasma chamber 22 includes one or more electrodes 24 therein that are configured to produce, with the use of a high voltage circuit (plasma generator) 28, a product gas 32 containing a desired amount of NO from the reactant gas. The system includes a controller 30 in electrical communication with the plasma generator 28 and the electrode(s) 24 that is configured to control the concentration of NO in the product gas 32 using one or more control parameters relating to conditions within the system and/or conditions relating to a separate device for delivering the product gas to a patient and/or conditions relating to the patient receiving the product gas. In some embodiments, the plasma generator circuit is a high voltage circuit that generates a potential difference across an electrode gap.

In some embodiments, plasma is generated with radio frequency energy. In some embodiments, NO generation can be modulated by adjusting one or more of the following parameters: RF Frequency, wave guide spacing, electrode gap, flow, pressure, temperature, etc. as variables in production. In some embodiments, the plasma generator circuit is a radio frequency (RF) power generator delivering RF power to one or more RF electrodes. In some embodiments, the RF power operates around 13.56 MHz with power in the 50-100 W range, however other power ranges can be effective depending on electrode design, production targets and reactant gas conditions. In some embodiments, RF power operates around 2.45 GHz for improved coupling and excitation of $N_2$ molecules. The controller 30 is also in communication with a user interface 26 that allows a user to interact with the system, view information about the system and NO production, and control parameters related to NO production.

In some embodiments, the reactant gas flow makes the plasma arc increase beyond the length of the electrode gap. NO production for a given electrode spacing is maximized by stretching the arc with reactant gas flow.

In some embodiments, the NO system pneumatic path includes a pump pushing air through a manifold 36. The manifold is configured with one or more valves: three-way valves, binary valves, check valves, and/or proportional orifices. The treatment controller 30 controls the flow of the pump, the power in the plasma and the direction of the gas flow post-electrical discharge. By configuring valves, the treatment controller can direct gas to the manual respiration pathway, the ventilator pathway or the gas sensor chamber for direct measurement of NO, $NO_2$ and $O_2$ levels in the product gas. In some embodiments, respiratory gas (i.e. the treatment flow) can be directed through a ventilator cartridge that measures the flow of the respiratory gas and can merge the respiratory gas with NO product gas.

The output from the NO generation system in the form of the product gas 32 enriched with the NO produced in the plasma chamber 22 can either be directed to a respiratory or other device for delivery to a patient, or can be directed to a plurality of components provided for self-test or calibration of the NO generation system. In some embodiments, the system collects gases to sample in two ways: 1) gases are collected from a patient inspiratory circuit near the patient and pass through a sample line 48, a filter 50, and a water trap 52, or 2) gases are shunted directly from the pneumatic circuit as they exit the plasma chamber 22. In some embodiments, product gases are shunted with a shunt valve 44 to the gas sensors after being scrubbed but before dilution into a patient airstream. In some embodiments, product gases are collected from an inspiratory air stream near the device and/or within the device post-dilution. Within the gas analysis portion of the device, the product gas passes through one or more sensors to measure one or more of temperature, humidity, concentrations, pressure, and flow rate of various gasses therein.

Figure 2:
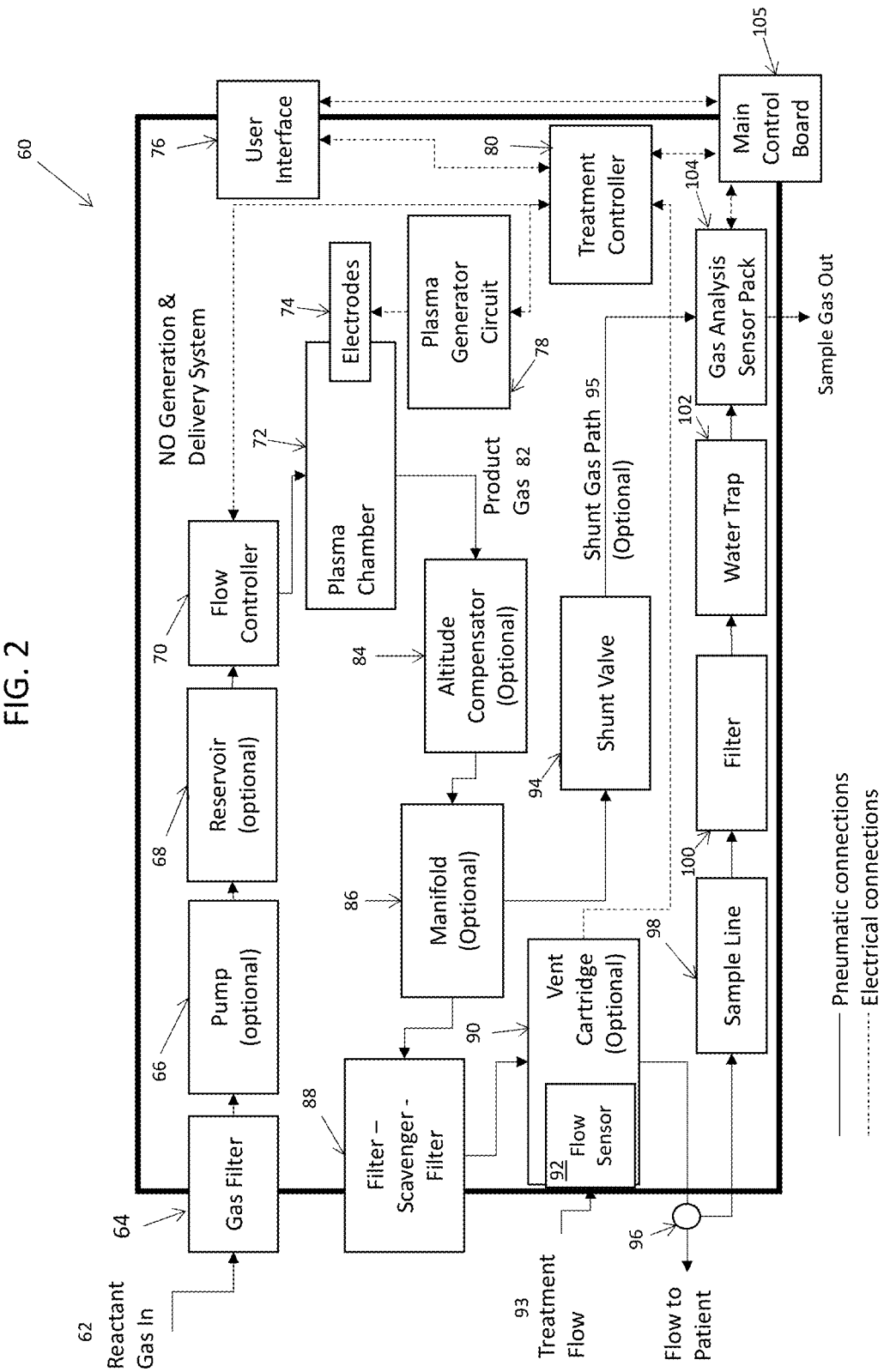
FIG. 2 is another exemplary embodiment of a system for generating an NO-enriched product gas.

FIG. 2 depicts an embodiment of a NO generation and delivery system 60. Reactant gas 62 enters the system through a gas filter 64. A pump 66 is used to propel gas through the system. Whether or not a system includes a pump can depend on the pressure of the reactant gas supply. If reactant gas is pressurized, a pump may not be required. If reactant gas is at atmospheric pressure, a pump or other means to move reactant gas through the system is required. A reservoir 68 after the pump attenuates rapid changes in pressure and/or flow from a pump. Coupled with a flow controller 70, the reservoir, when pressurized, can enable a system to provide flow rates to the plasma chamber 72 that are greater than the pump 66 flow rate. Electrodes 74 within the plasma chamber 72 are energized by a plasma generation circuit 78 that produces high voltage inputs based on desired treatment conditions received from a treatment controller 80. A user interface 76 receives desired treatment conditions (dose, treatment mode, etc.) from the user and communicates them to the main control board 105. The main control board 105 relays to the treatment controller 80 a target dose and monitors measured NO concentrations from the gas analysis sensor pack 104. The main control board 105 monitors the system for error conditions and can generate alarms, as required. Reactant gas 62 is converted into product gas 82 when it passes through the plasma chamber 72 and is partially converted into nitric oxide and nitrogen dioxide. An altitude compensator 84, typically consisting of one or more valves (i.e. proportional valves, binary valves, 3-way valves, etc.), is optionally used to provide a back-pressure within the plasma chamber 72 for additional controls in nitric oxide production. Product gases pass through a manifold 86, as needed, to reach a filter-scavenger-filter 88 assembly that removes nitrogen dioxide from the product gas. From the filter-scavenger-filter 88, product gas is introduced to a patient treatment flow directly, or indirectly through a vent cartridge 90. In some embodiments, the vent cartridge 90 includes a flow sensor 92 that measures the treatment flow 93. The treatment flow measurements from the flow sensor 92 serve as an input into the reactant gas flow controller 70 via the treatment controller 80. After product gas 82 is introduced to the treatment flow, it passes through inspiratory tubing. Near the patient, a fitting 96 is used to pull a fraction of inspired gas from the inspiratory flow, through a sample line 98, filter 100, water trap 102 and Nafion tubing to prepare the gas sample and convey it to gas sensors 104. Sample gas exits the gas analysis sensor pack 104 to ambient air. In some embodiments, the system 60 can optionally direct gas through a shunt valve 94 and shunt gas path 95 directly to the gas sensor pack and out of the system. In some embodiments involving the shunt valve 94, the manifold 86 includes a valve (not shown) to block flow to the filter-scavenger-filter when the shunt valve 94 is open.

Figure 3:
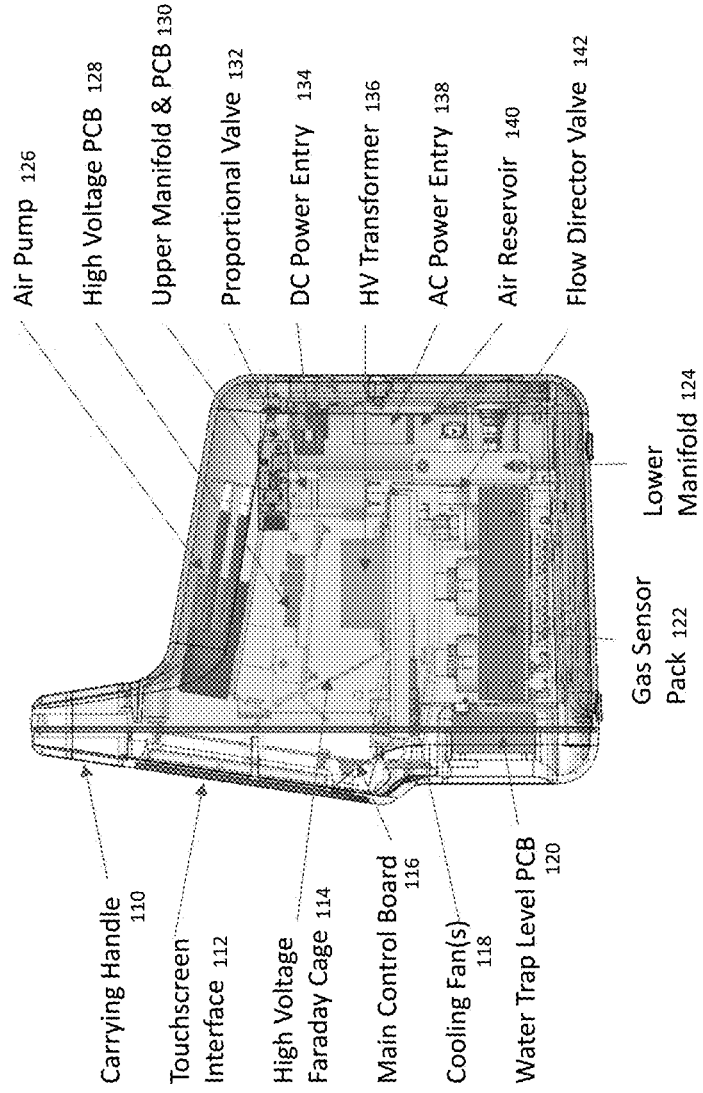
FIG. 3 is an exemplary embodiment of an NO generation system.

Another exemplary embodiment of an NO generation system is shown in FIG. 3, which includes a carrying handle 110, an interface 112, a high voltage cage 114, a control board 116, one or more cooling fans 118, and a water trap PCB 120. The system also includes a gas sensor pack 122, a lower manifold 124, an air pump 126, a high voltage PCB 128, an upper manifold 130, a proportional valve 132, a DC power entry 134, a high voltage (HV) transformer 136, an AC power entry 138, a reservoir 140, and a flow director valve 142.

Figure 4:
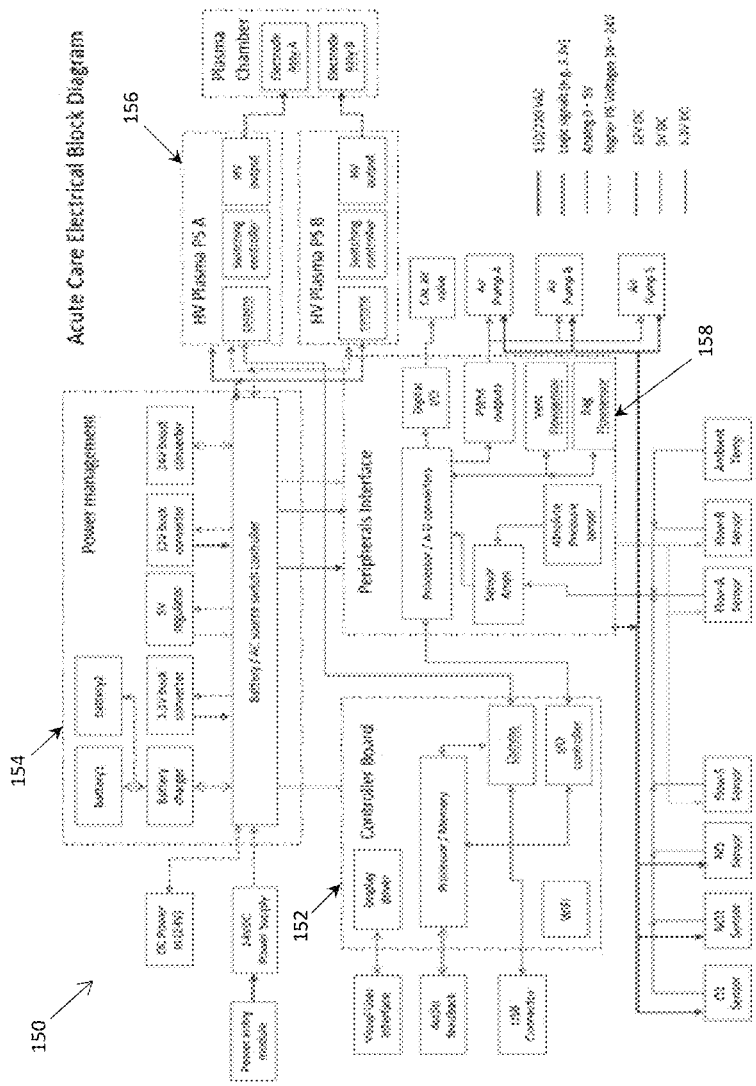
FIG. 4 illustrates an embodiment of a schematic of a controller of an NO generation system.

FIG. 4 depicts a schematic showing all the components of an embodiment of an NO device 150, including a control board 152, a power management circuit 154, one or more electrode assemblies 156, and a peripherals interface 158. A plasma chamber can be part of the reusable controller or removable and disposable.

Figure 5:
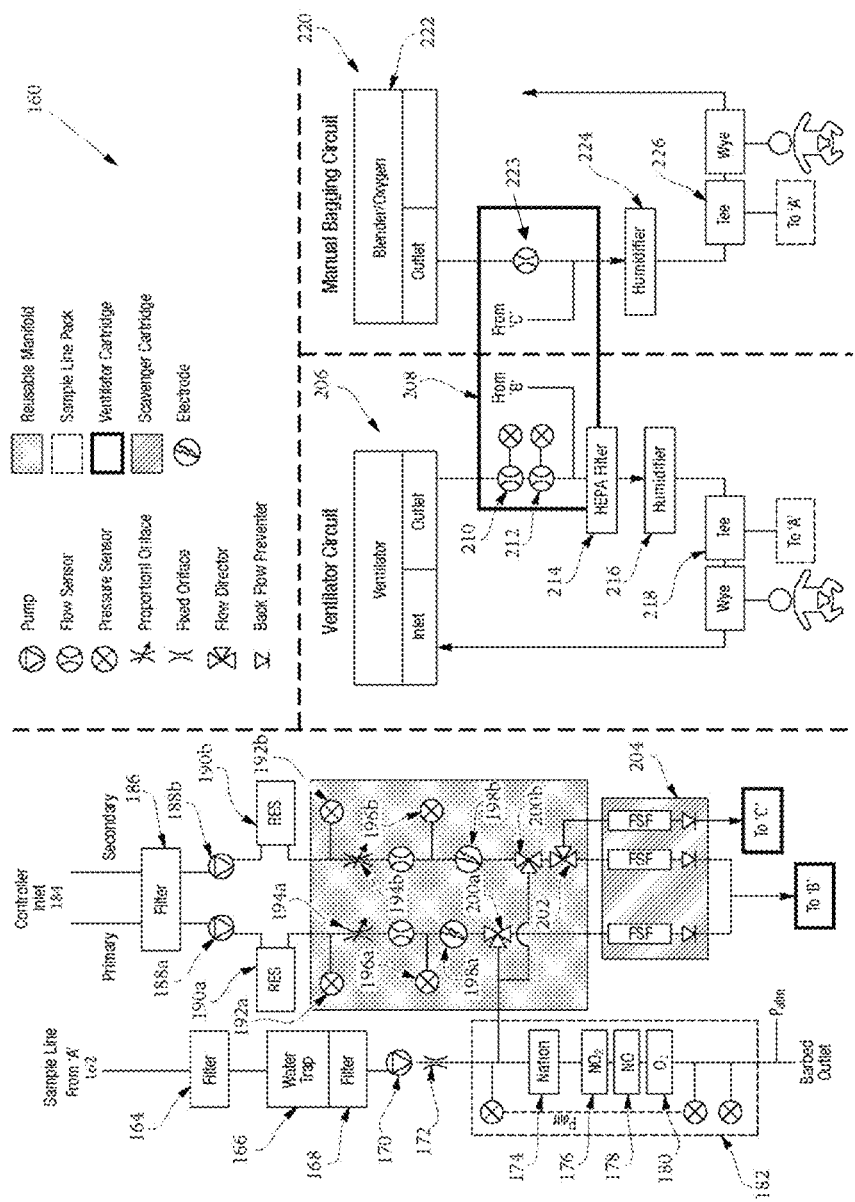
FIG. 5 is an embodiment of a pneumatic circuit.
Figure 6:
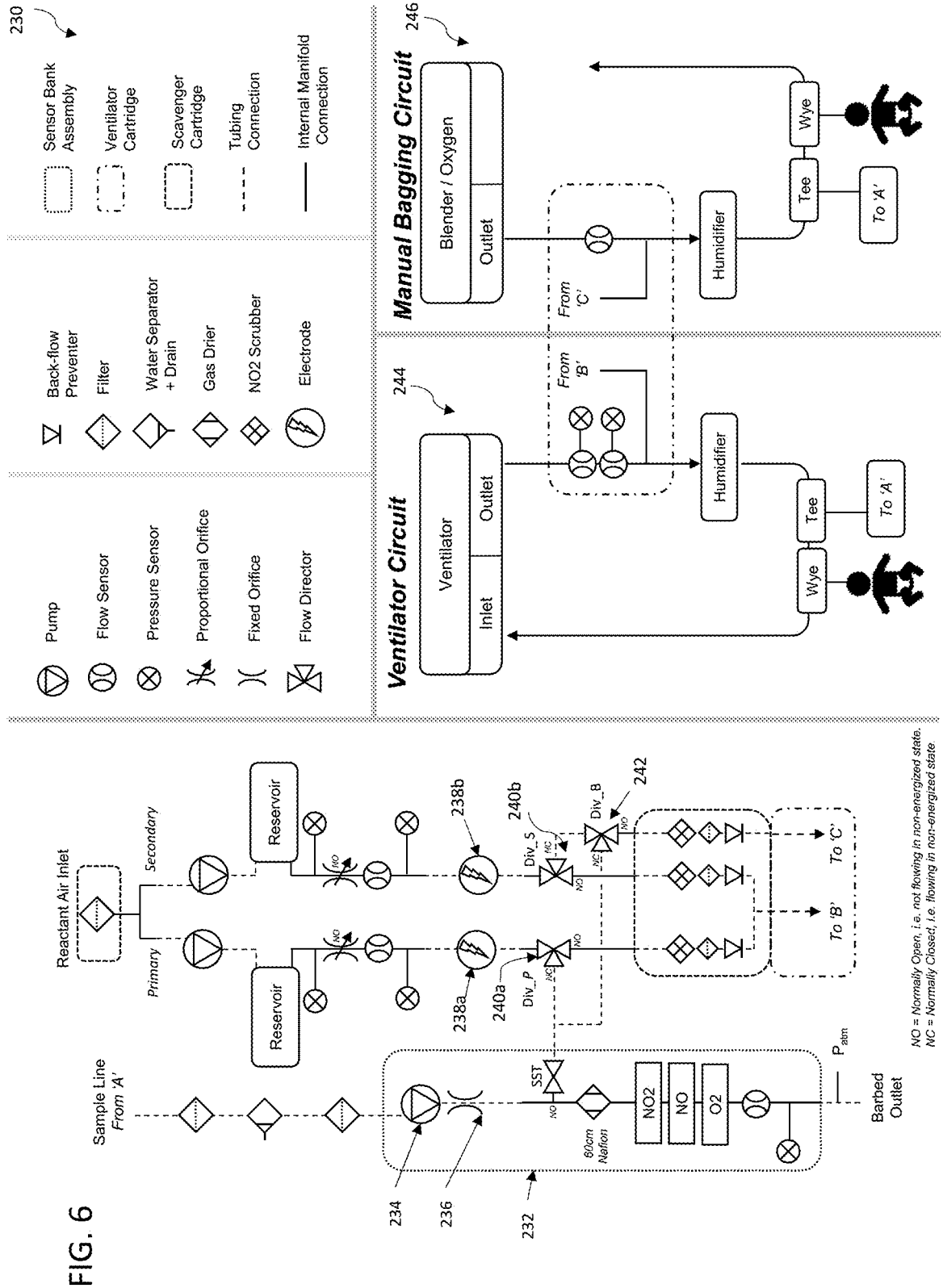
FIG. 6 is another embodiment of a pneumatic circuit.

FIG. 5 and FIG. 6 depict embodiments of NO generation and delivery systems with redundant NO generators. FIG. 5 depicts an exemplary pneumatic design 160 for an NO generation and delivery system. In the upper left of the diagram, sample gases 162 originating in the treatment circuit (lower right of FIG. 5 labeled 'A') enter the system through a hydrophilic filter 164 and travel through a water trap 166. In some embodiments, this filter 164 is disposable so that the user can replace it as needed when it clogs. An additional filter 168 after the water trap 166 protects the gas analysis sensors from contaminants. In some embodiments, the additional filter 168 is hydrophobic to prevent liquid contents from the water trap from entering the gas sensor assembly. Sample gases then flow through a pump 170 and then through a fixed orifice 172 that limits the gas flow rate through the sensors and diminishes pulsatility in the sample gas flow. Some gas sensors, for example electrochemical sensors, are sensitive to the amount of water content within a sample gas and can require the gas to have approximately 50% relative humidity. Gas flows through Nafion tubing 174 to add humidity to the sample from the atmosphere in the event that sample gases are very dry as can be the case when calibration gases are used. Conversely, if the gas sample to too humid, Nafion tubing 174 can remove humidity from the gas sample, driving the sample gas humidity towards ambient levels. Next, the sample gas flows through one or more gas analysis sensors. Sensor 176 measures $NO_2$, sensor 178 measures NO, sensor 180 measures $O_2$. A differential pressure sensor shown on the left side of the sensor manifold block is used to measure the flow rate through the gas sensor manifold 182. This flow rate can be used to ensure that the sample pump is functioning and that the sample line, disc filter, and water trap are not clogged and/or kinked. An absolute pressure sensor near the end (bottom) of the sensor manifold is used to measure atmospheric pressure. Gases exit the sensor manifold and flow through a T-fitting, where one leg is connected to atmospheric pressure and the other leg is connected to an external port in the device. The second leg is connected to atmosphere to prevent hospital vacuum from affecting the flow rate through the gas sensor manifold and potentially affecting patient treatment. The external port can be connected to hospital vacuum or just vented to atmosphere.

Moving to the right in FIG. 5, at the top of the diagram there is an inlet 184 to receive reactant gas into the system. In some embodiments, this is a 22 mm medical air connection. Incoming reactant gas flows through a filter 186 to remove particulate then bifurcates into two parallel NO generation paths. Each path consists of a pump 188a, 188b, a reservoir 190a, 190b, a reservoir pressure sensor 192a, 192b, a proportional flow valve 194a, 194b, a fixed orifice, a plasma chamber pressure sensor 196a, 196b, and a plasma chamber 198a, 198b. After the plasma chamber 198a, 198b, each flow path has a flow director 200a, 200b that can direct gases to either the gas sensor manifold 182 or towards the patient inspiratory air. These side paths to the gas sensor manifold 182 enable a system to evaluate the gas produced and/or redirect gases within the plasma chamber away from the patient. After the gas analysis side paths, one of the gas paths utilizes a flow director 202 to select whether product gases will flow to a ventilator circuit (B in the figure) or to a manual bag outlet (C in the figure). Gases then flow through one of three parallel scrubber passages in a disposable cartridge 204. The scrubber passages consist of a filter, scrubber material, a second filter and a one-way valve. The one-way valve ensures that pressures and materials outside of the system do not enter the cartridge and controller.

In the lower right corner of FIG. 5, a treatment setup is depicted. In a ventilator circuit 206, inspiratory gases exit the ventilator and enter a ventilator cartridge 208. The gases flow through two flow sensors 210, 212. In some embodiments, the flow sensors measure pressure, humidity and temperature in addition to flow. NO-containing product gas is merged with the inspiratory flow after the flow sensors. Inspiratory flow continues through a HEPA filter 214, a humidifier 216 and on to a "T" fitting 218, where sample gases are pulled, then on to the patient.

Also shown in the lower right corner of FIG. 5 is a manual bagging circuit 220. Inspiratory gases are sourced from a blender/wall outlet/cylinder 222 and enter the ventilator cartridge 208. Flow is measured within the ventilator cartridge 208 prior to adding NO-containing gas. Gases flow through an optional humidifier 224 and on to a "T" fitting 226 where sample gases are pulled and then on to the patient.

FIG. 6 illustrates a similar system to the embodiment of the system shown in FIG. 5. As explained above, FIG. 5 depicts how the filter-scrubber-filter assemblies can be grouped into a cartridge 204, and FIG. 5 also depicts how gas sensors (176, 178, 180), Nafion tubing 174, a manifold, and pressure/flow sensors can be grouped into a gas sensor assembly 182. In FIG. 6, a gas sensor assembly 232 includes a pump 234 and a flow sensor 236. FIG. 5 depicts how vent flow sensors 210, 212, a bag flow sensor 223, pressure sensors, and NO injectors can be grouped into the vent cartridge 208.

A HEPA filter 214 connects to the ventilator cartridge 208 to keep the ventilator cartridge clean. In some embodiments, the HEPA filter utilizes a standard, 22 mm pneumatic connection for ease of replacement and optional use. In some embodiments, the HEPA filter connects to the ventilator cartridge with a connection to ensure that the system cannot be used without it. The connection prevents uses from connecting an inspiratory limb to a NO generator with standard 10 mm, 15 mm, and 22 mm male and female tubing fittings. FIG. 47A, FIG. 47B, FIG. 47C and FIG. 47D depict examples of pneumatic connections that can be used between the HEPA filter and ventilator cartridge and/or NO generator. FIG. 47A is an O-ring seal between HEPA and controller. As the HEPA is inserted, the O-ring is compressed within a bore within the controller. In some embodiments, a retention feature (not shown) is engaged that prevents the HEPA filter from pulling out without a use-step of releasing the retention feature. In some embodiments, the interface between HEPA filter and vent cartridge is comprised of a tapered tubing connection similar to standard connections but with a different diameter that prevents engagement of standard tubing sizes. FIG. 47B shows another embodiment where the HEPA filter includes a magnet. When the HEPA filter is engaged, the magnet actuates a Reed switch within the NO generator that informs the NO generator that the HEPA filter is present.

FIG. 47C depicts an embodiment where the HEPA filter includes a conductive surface that closes a circuit within the NO generator when the HEPA filter is fully inserted. FIG. 47D depicts an embodiment where the HEPA filter has a reflective feature that closes an optical circuit when the HEPA filter is fully inserted. In some embodiments, the HEPA filter is engages the ventilator cartridge or NO generation device with threads.

FIG. 5 and FIG. 6 further differ in pneumatic design post-plasma chamber. In FIG. 5, in both NO generation channels, a first flow-director (200a, 200b) directs product gases to either the gas sensor pack 182 or the gas scrubber cartridge 204. In the secondary channel, a second flow director directs product gases to either a vent circuit (path B) or a bag circuit (path C). In FIG. 6, the pneumatic pathway differs in that a first flow director selects between vent circuit and the sensors while a second flow director selects between shunting to the sensors and bag circuit. The pneumatic design in FIG. 6 has an advantage over the flow design of FIG. 5 due to having equal flow restriction in both channels between the plasma chamber and the vent flow injector. This relates to minimizing the flow path length and having the flow restriction of the two paths be substantially identical so that they can have similar if not identical calibration settings and NO production.

In some embodiments, a scrubber cartridge can be used for demonstration purposes. The demo device can be identified by RFID, memory device, 2-d bar code, mechanical interface, optical interface, lower flow restriction, or other means by a controller to enable a demonstration mode for training purposes. In some embodiments, the demonstration scrubber cartridge is non-functional for clinical purposes.

Electrode Design

The orientation of electrodes can vary with respect to the reactant gas flow. In some embodiments, the electrode gap is orthogonal with the reactant gas flow. Typically, the reactant gas flow is directed towards or through the gap. This allows for stretching of the arc, which facilitates higher NO productions for a given input power than would otherwise be possible for a specified gap. Larger gaps are more power efficient (production per watt), so stretching the arc achieves efficiencies of larger gaps. Larger gaps also require higher voltages to initiate the plasma, so a stretched arc requires less voltage for the same production. In some embodiments, the electrode gap is parallel, or axial, to the reactant gas flow. Axial orientation can be less sensitive to reactant gas velocity changes. The gap can be increased for larger production levels or higher efficiencies.

Figure 7:
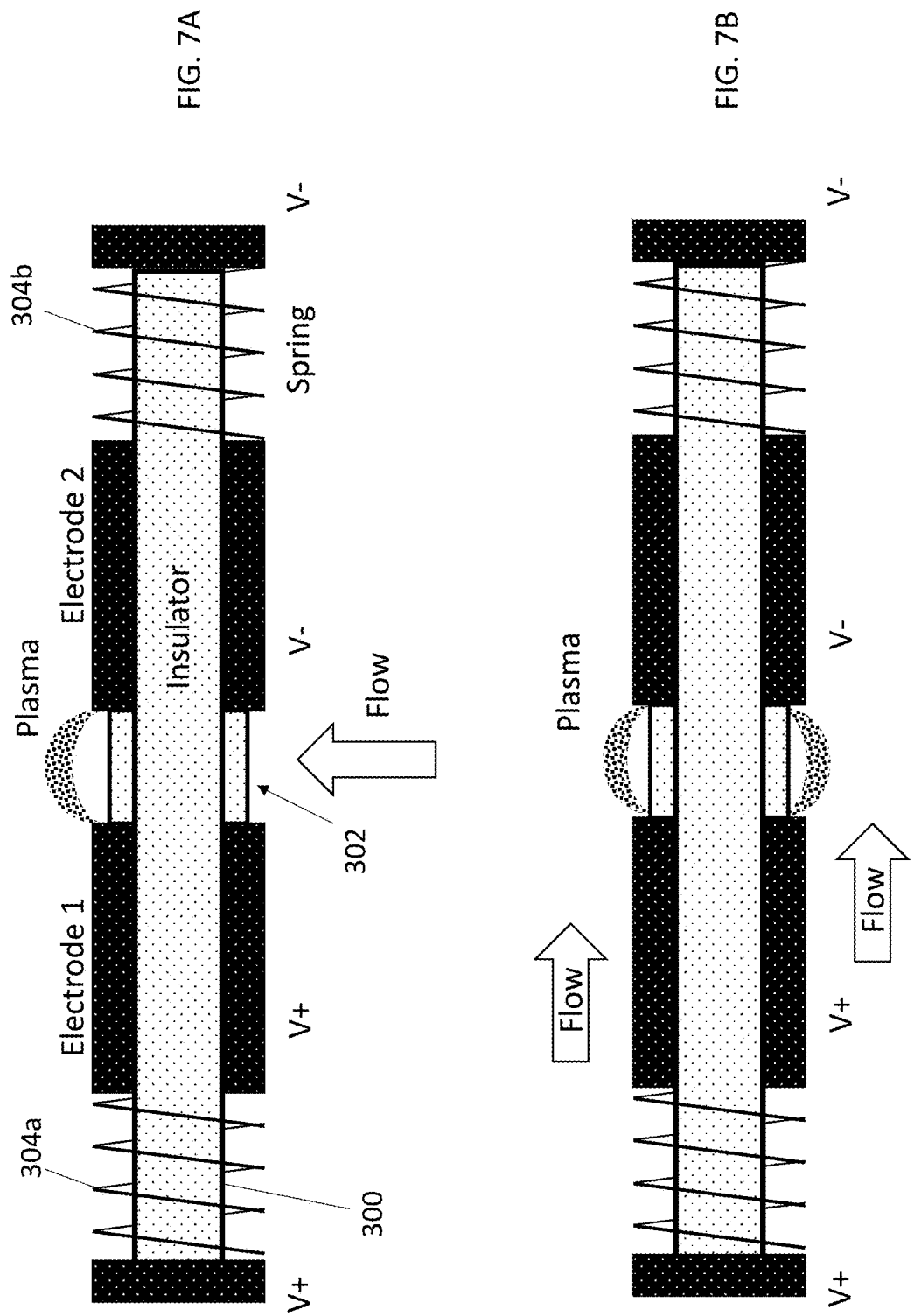
FIG. 7A and FIG. 7B are exemplary embodiments of electrodes formed from non-electrically conductive rods.

In some embodiments, an electrode can be comprised of a non-electrically conductive rod with beads (short tubes) slid onto its length, as shown in FIG. 7A and FIG. 7B. A non-conductive bead 302 (i.e. an insulator bead) is located in the middle of the central rod 300 with conductive beads on either side. High voltage is applied to beads located at each end of the rod with electrical arcing taking place across the center bead location. Springs 304a, 304b on one or both sides of the assembly complete the electrical connections and ensure that the electrode gap remains consistent by pressing the stack of beads towards the non-conductive bead in the center. This design offers consistent gap length and long electrode life because it accommodates for electrode wear. This design can also decouple reactant gas flow from NO production by eliminating arc bending described above. The orientation of this electrode with respect to the flow of reactant gas can have an effect on electrode life, the product gas and reactor production. This electrode is best suited to reactant gas flow that is parallel to the electrode long axis (as shown in FIG. 7B), where the plasma will wear the electrodes evenly, whereas orthogonal flow (as shown in FIG. 7A) will generally wear the electrodes on the down-stream side of the electrodes, meaning the springs will not be able to maintain the intended gap length set by the non-conductive bead.

Figure 8:
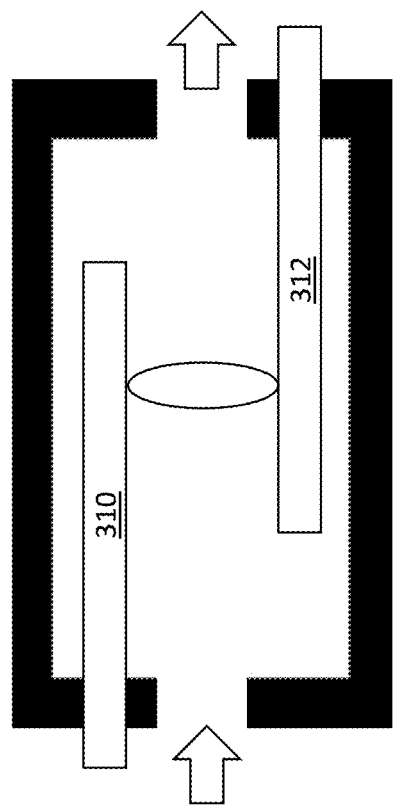
FIG. 8 is an exemplary embodiment of an electrode design having two electrodes oriented parallel to one another.

In some embodiments, two electrodes can be oriented parallel to each other, such as electrodes 310, 312 shown in FIG. 8, providing increased surface area for prolonged longevity. This design has the benefit of electrodes entering from opposite ends of the plasma chamber to keep high voltage lines far apart to minimize internal and external creepage distances around the chamber. Ridges inside and outside the chamber can further increase creepage distances. Larger overlap between the electrodes can improve electrode longevity by providing more material for arcing. This design has shown two discrete arcing locations from the end of one electrode to the side of the other, and vice-versa. When alternating current is applied, the electrodes break down from point to line fairly evenly between the two electrodes This design provides further benefit by establishing the electrode gap by the hole locations in the chamber, rather than sliding electrodes along their long axis. In some embodiments, the rods are not parallel so that a gliding arc design is created. Electrodes can be circular in cross section or have a non-circular cross section. Non-circular cross sections can provide sharp edges and features to intensify the electric field in that area to reduce break-down voltage. The electric field can be high between the electrodes. FIG. 8 shows air flow parallel to the electrodes 310, 312. This can be beneficial because gas can be more focused towards both arcing locations. A further benefit is that one electrode is upstream of the plasma, decreasing the potential for sputtered electrode materials establishing a conductive path between the two electrodes. In some embodiments, a parallel electrode design utilizes different materials at tip and shaft. In some embodiments, tungsten is the cathode and a noble metal or alloy, such as iridium, rhodium or palladium is the anode. This solution provides the high temperature resistance of tungsten but protects the tungsten from the highly oxidizing environment of the anode. Palladium is more resistant to oxidation, so it serves as the anode. In some embodiments, air flow is orthogonal to the plane of the electrodes and directed towards the region defined by the electrode gap and overlap region. Nozzle size and electrode overlap can impact NO production efficiency significantly.

Figure 9:
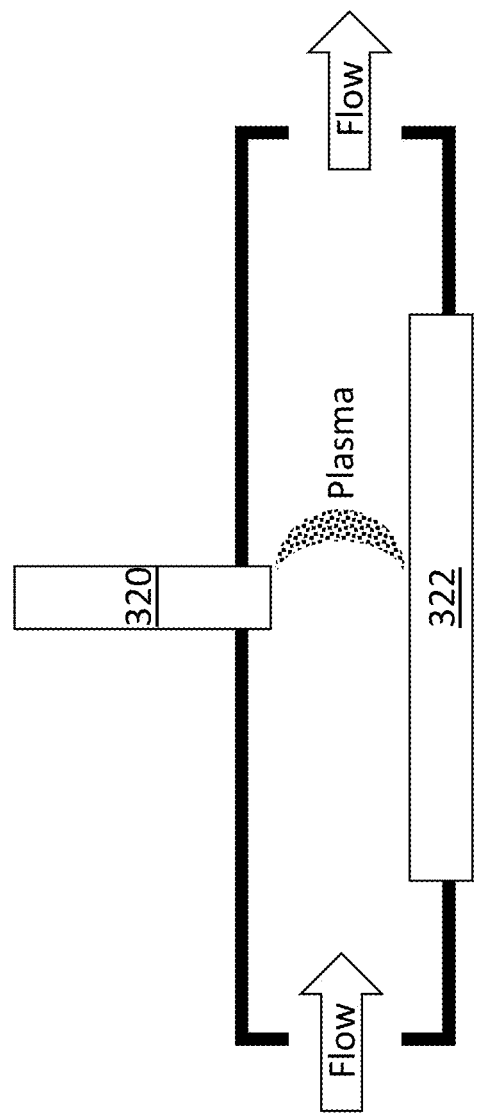
FIG. 9 is an exemplary embodiment of an electrode with a "T" orientation.

In some embodiments, the orientation of electrodes is asymmetrical to generate an asymmetrical electrical field. This can lower DC breakdown voltage. In some embodiments, this can be achieved with electrodes oriented like a "T" for a point-plane relationship, such as electrodes 320, 322 shown in FIG. 9. A similar approach can be achieved with two electrode rods where by the end of one electrode arcs to the side of the other electrode, which could be referred to as "point to line."

Figure 10:
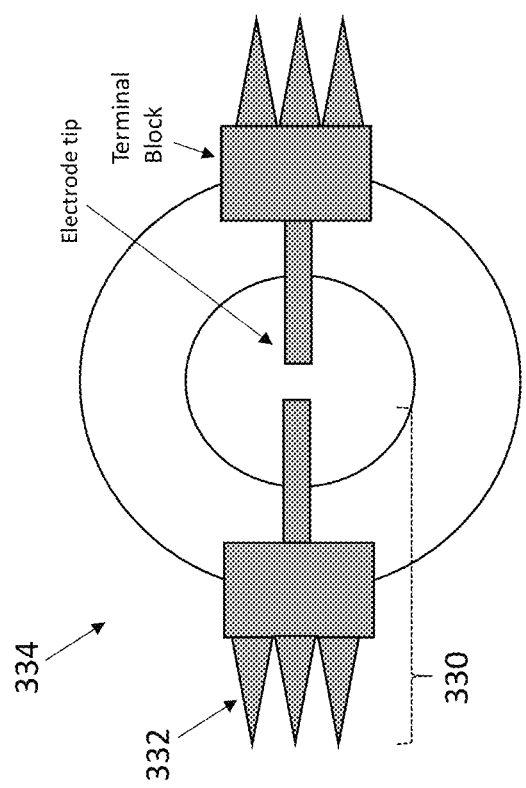
FIG. 10 is an exemplary embodiment of a monolithic electrode and heat sink design.

In some embodiments, as shown in FIG. 10, a monolithic electrode 330 and heat sink design is used in a plasma chamber 334 to maintain electrode temperature at an optimal level. A monolithic electrode can be made out of an economical base metal and plated with a desired electrode material. The monolithic electrode 330 can have cooling lines running through it, or can have cooling fins 332 to act as a heat sink. A monolithic electrode can be beneficial because the geometric features required to facilitate the plasma are not generally the features which facilitate heat removal, mechanical mounting, electrical connection, or pneumatic sealing. Because of the different features required for different requirements of the design, the electrode is typically more than one parts which must be joined together. The joining methods create failure modes, such as leak points or electrical shorts, as well as adding manufacturing complexities and costs. By having a single monolithic electrode, all required features can be combined into one part, thereby reducing complexity and increased reliability.

In some embodiments, the relationship between gas flow rate or velocity and electrode diameter and electrode length is controlled to maintain electrode temperature at optimal level. For example, the bulk of the electrode could be buried within a manifold thus relying on conduction to remove heat, or some amount of surface area could be intentionally in the gas flow path to remove heat from convection. The amount of surface area is controlled by the diameter and length.

In some embodiments, a pair of electrodes is provided where one electrode is a different material from the other electrode.

In some embodiments, a pair of electrodes is provided where the AC waveform is rectified to create a dedicated anode and dedicated cathode.

In some embodiments, a pair of electrodes is provided where a dedicated cathode, which is no longer subject to mass erosion via ion-bombardment is to be considered a permanent (or longer-lasting) part of the device and may be made from a noble metal, which is less susceptible to erosion via oxidization or vaporization of the base metal or its oxide species, while the dedicated anode which may be made from an economical electrode material, such as copper, tungsten, or steel which will not be in use long enough to experience mass erosion from ion-bombardment, but can be replaced before it erodes substantially from vaporization or oxidation.

In some embodiments, a pair of electrodes is provided where one electrode is tied to chassis or earth ground inside the device. This electrode can be at low voltage and therefore safely incorporated into a disposable cartridge which would otherwise require excessive creepage and clearance distances.

In some embodiments, an electrode is provided with an additive metal to form an alloy intended to lower the work function and improve the arc initiation or arc stability.

In some embodiments, one or more electrodes can be constructed from a metal that forms an oxide that has a substantially lower melting temperature than the base metal, such that a non-conductive oxide layer never builds up over the electrode surface. This improves arc starting stability as the non-conductive oxide layer.

Figure 11:
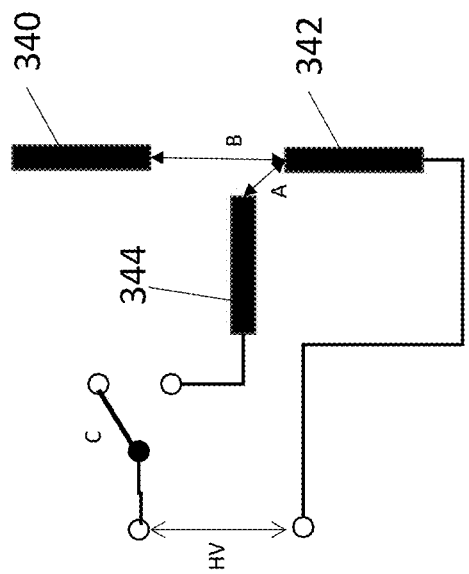
FIG. 11 is an exemplary embodiment of an electrode design having three electrodes providing two gaps.

In some embodiments, there are three electrodes 340, 342, 344 providing two gaps, as shown in FIG. 11. In some embodiments, there is a short gap A and a long gap B as shown in FIG. 11. The short gap can be used for low NO production levels and can provide electrons to assist in breaking down the long gap. The long gap can be used for higher range NO production. Using short and long gap for different NO production ranges drastically improves the total dynamic range of an NO Production system, while also drastically improving resolution within that range. In some embodiments, arcing is initiated at the short gap prior to changing the high voltage circuit to pass through the long gap. In some embodiments, the short gap sustains a plasma during device operation to shorten the breakdown of the large gap by providing constant source of electrons in the vicinity of the electrodes, much like a pilot light for a natural gas water heater maintains a flame. The dimensions of the short and long gaps can vary. In some embodiments, the short gap is roughly 0.1-0.5 mm while the large gap can be 1.5-6 mm depending on the desired dynamic range or resolution. In some pulsed NO generation embodiments, the short gap is energized before the large gap for each NO generation pulse. This can improve the reliability of breaking down the large gap. A double pole, single throw switch as shown in FIG. 11 can be used for DC applications. For AC applications, the switch would be a double pole, double throw unit.

Figure 12:
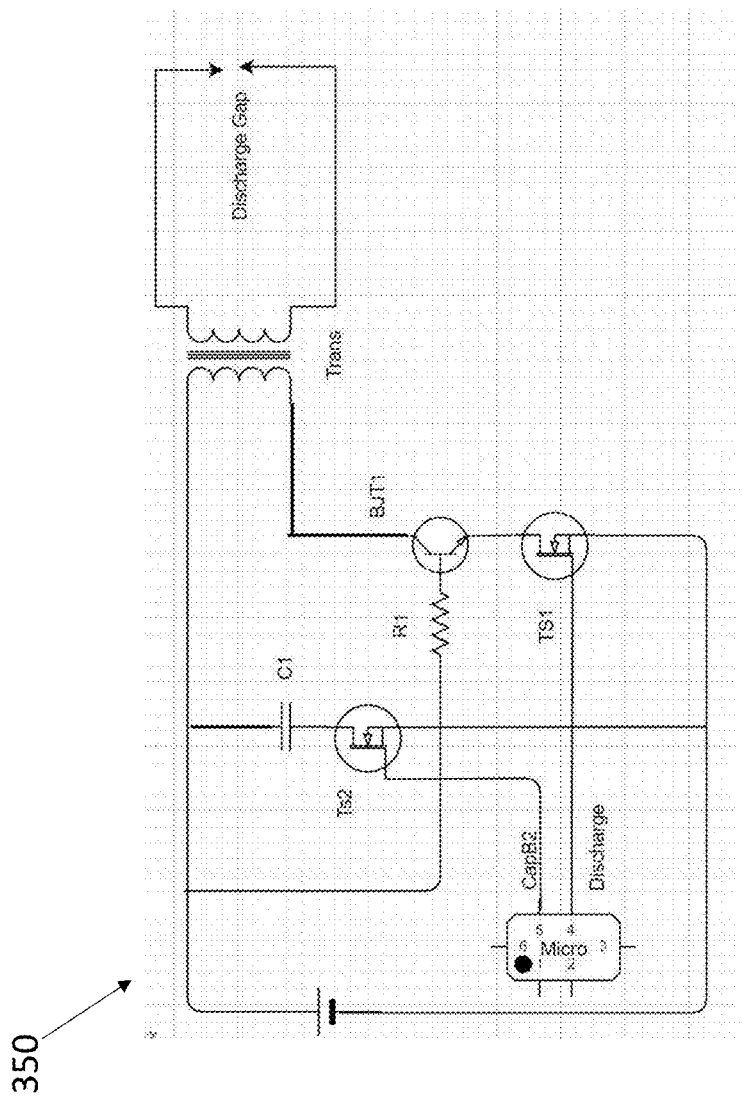
FIG. 12 is an exemplary embodiment of a circuit having a transformer tuned to raise the voltage to one that will arc across a specific electrode gap size.

In some embodiments, a capacitor is loaded with energy between electrical discharges and delivers its energy to an electrode gap at a time selected by the NO generation controller. The circuit 350 shown in FIG. 12 is a DC powered circuit with a transformer (Trans) tuned to raise the voltage from the battery voltage to a voltage that will arc across a specific gap size. R1 sets the bias voltage and limits the current to the base of the transistor (BJT1) thus enabling current to flow through BJT1. The microprocessor provides timing for the charging and enabling of the capacitor (C1). The microprocessor provides a switching circuit (TS1) to turn off and on the voltage/current to the transformer (which in-turn generates a high enough voltage to discharge across the electrode. In conjunction with this timing the microprocessor can coordinate the switching circuit TS2 to charge and discharge C1 allowing for the additional current into the primary circuit (when the discharge gap is generating plasma). As a person skilled in the art would know, C1 is tuned to the impedance of the circuit to maintain the proper time constants.

Figure 13:
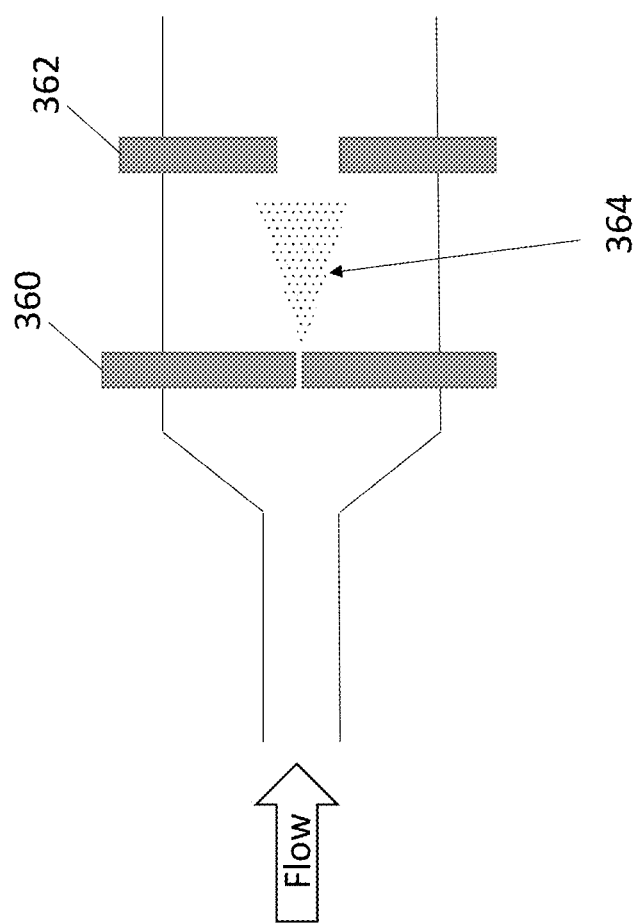
FIG. 13 is an exemplary embodiment of two electrode pairs with different gap sizes.

In some embodiments, multiple pairs of electrodes are located within a common plasma chamber. A first pair of electrodes 360 has a short gap for generating low amounts of NO. A second pair of electrodes 362 has a longer gap for generating high amounts of NO, as shown in FIG. 13. In some embodiments, the short gap electrode is energized first to generate electrons 364 (or an ion cloud) to facilitate break down of the longer gap electrodes. In some embodiments, a short gap generates electrical discharges at different frequency than a large gap. In some embodiments, two electrode pairs are used with the same gap by different electrode materials to provide different amounts of NO production from each electrode pair. In some embodiments, a channel of a NO generation device can include two or more flow controllers, each with a plasma chamber and specific electrode gap.

In some embodiments, a NO generation device contains multiple plasma chambers that can be selected one at a time for NO generation. In some embodiments, the chambers are oriented like a revolver where each chamber can be indexed into the flow path of the reactant gas.

Figure 14:
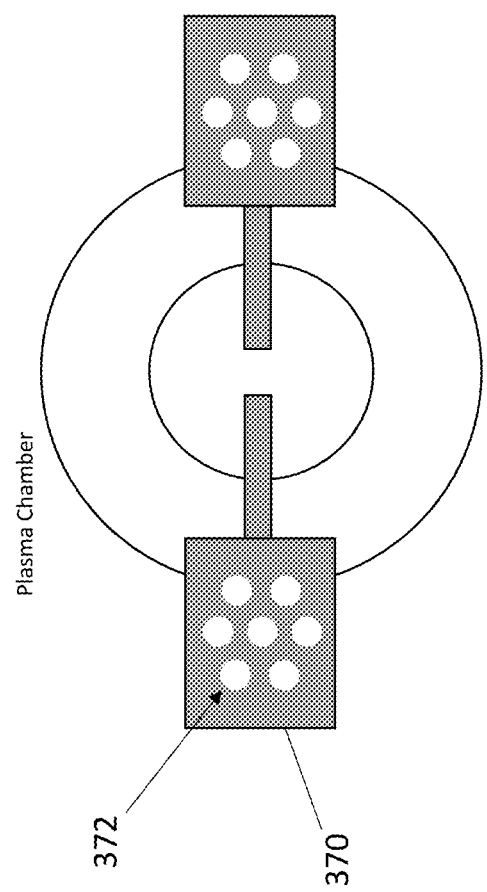
FIG. 14 is an exemplary embodiment of an electrode with coolant passageways.

In some embodiments, electrodes have coolant passageways within them, as shown in FIG. 14. Coolant passageways 372 pass through electrodes 370 to keep them cool and prolong electrode life. In some embodiments, reactant gas passes through the electrodes prior to being stored in the reservoir to minimize humidity condensation. In some embodiments, gliding arc electrodes include tubes with coolant flow within them. Coolant can be gas or liquid. In some embodiments, a non-electrically conductive coolant is pumped from a reservoir through one or more electrodes and back to the coolant reservoir.

In some embodiments, the NO generation system can include features that can be configured to cool the electrodes and/or plasma chamber. For example, reactant gases can be used to cool the electrodes and/or plasma chamber. In some embodiments, a plasma chamber can be removable for servicing. Removable plasma chambers can be made from high temperature materials, such as metals, glass, ceramic, composite and high temperature polymers. In some embodiments, the plasma chamber can be made from a thermally conductive material, such as aluminum. Seals between a removable plasma chamber and a manifold can be made with O-rings, lip-seals, gaskets, elastomeric materials, compression fittings, barb fittings, and the like. Space between the O-rings can collect $NO_2$ over time. In some embodiments, gas travels from the manifold to an O-ring groove and travels circumferentially around the plasma chamber prior to entry into the plasma chamber. A similar approach can be done for product gases exiting the plasma chamber. This approach can allow gases passing circumferentially around the plasma chamber to cool the plasma chamber and no dead-end cavities where $NO_2$ can stagnate. FIG. 15A, FIG. 15B, FIG. 15C, FIG. 15D, FIG. 15E, FIG. 15F, FIG. 15G and FIG. 5H illustrate an embodiment of a removable plasma chamber.

FIG. 15A and FIG. 15B depict an electrode 382 mounted to a plasma chamber 380. Circumferential grooves around the plasma chamber are used for O-ring seals and for routing reactant and product gas as shown. A high voltage connection is at one end of the assembly. High voltage current conducts through an insulator to a center electrode within the plasma chamber. The plasma chamber is grounded and electrically connected to the ground electrode.

FIG. 15C, FIG. 15D, FIG. 15E, FIG. 15F, and FIG. 15G depict cross-sectional views of a high voltage electrode assembly. The electrode 382 seals to the plasma chamber with an O-ring and is held in place with a retaining plate. The orientation of the ground electrode with respect to air flow is selected so that the electrode does not interfere with gas flow through the electrode gap while remaining upstream of the plasma. This prevents deposition of conductive materials from electrode degradation or carbon formation between the two electrodes, thereby creating a short circuit. In some embodiments, a staggered inlet and outlet facilitate one blind mate connection. In some embodiments, features that can contribute to air exchange in order to minimize a stagnant bolus of nitrogen dioxide include air circling the plasma chamber before entry and after exit ensures complete exchange, and staggered inlet and outlet within the plasma chamber. In some embodiments, the electrode can be "clocked" so the "ground wire" is upstream of any iridium oxide deposited on the ceramic which could create a creepage path.

Figure 15E:
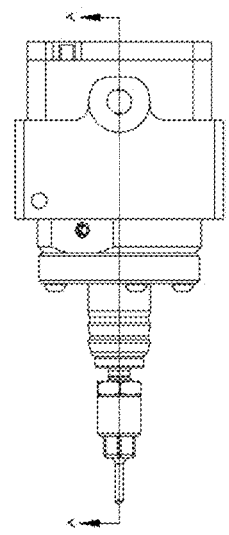
Figure 15G:
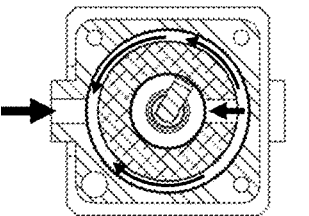
Figure 15F:
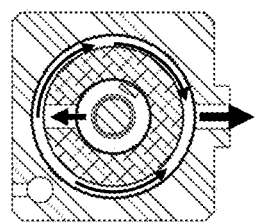
Figure 15C:
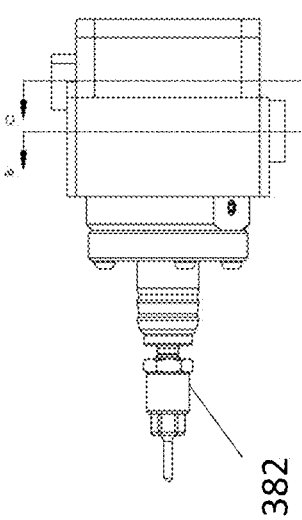
Figure 15D:
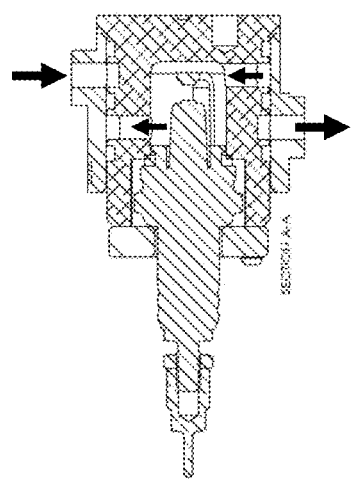
Figure 15H:
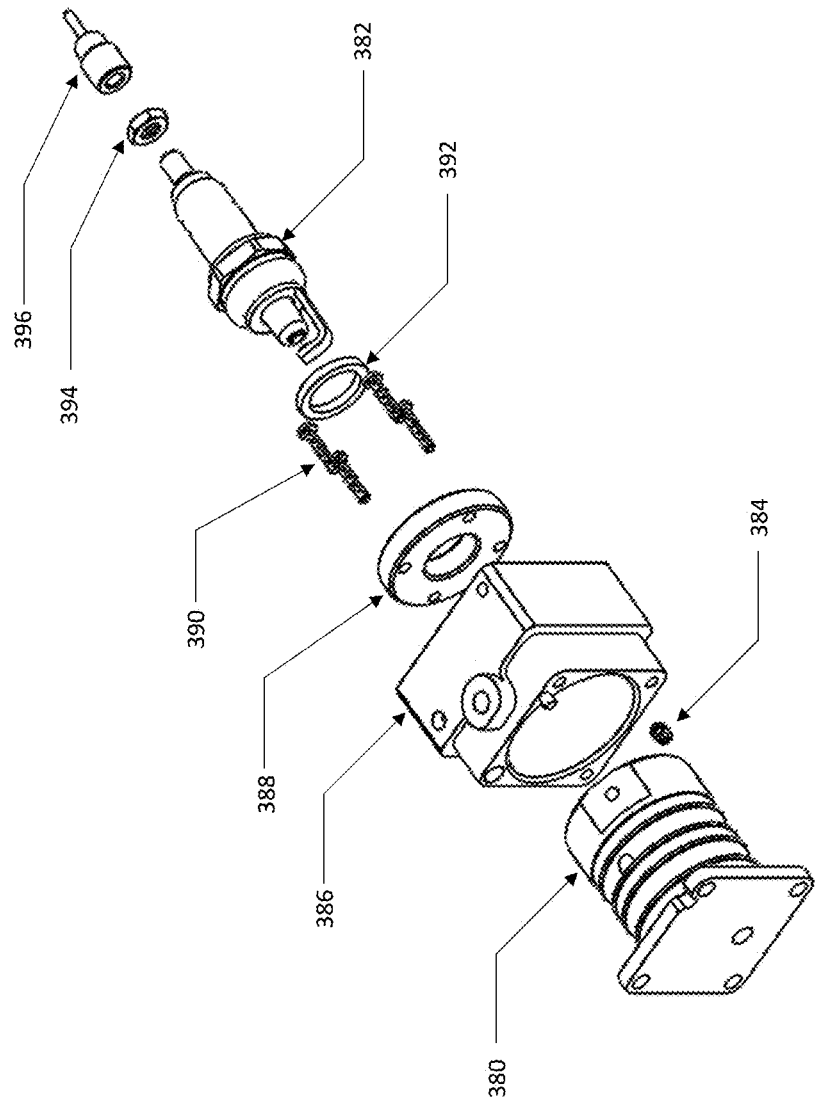

FIG. 15H shows an exploded view of an electrode and plasma chamber assembly. A plasma chamber component includes a cavity (directed away from the viewer) and has circumferential grooves for O-ring seals and gas pathways. In some embodiments, the plasma chamber is constructed from aluminum. A set-screw 384 is used to lock the electrode 382 in place and provide a reliable electrical connection between the electrode and the plasma chamber. A plasma manifold 386 provides reactant gas to the plasma chamber and directs product gases away from the plasma chamber. In some embodiments, the manifold is constructed from PEEK polymer. A clamp 388 and screws 390 provide compressive force to hold the electrode 382 to the plasma chamber 380 and maintain a pneumatic seal provided by the O-ring 392. The electrode consists of a center electrode housed within a ceramic insulator and secondary J-shaped electrode. A retaining nut 394 threads onto the top of the electrode and is used to jam against the threaded adaptor component 396 to provide a specific length to the assembly. The entire assembly (minus the manifold) can be removably inserted into the plasma manifold for replacement, as needed.

Conductive heat transfer between the electrode and chamber can be enhanced by material selection. Ceramic plasma chambers conduct heat better than polymeric chambers, resulting in lower electrode temperatures. Cooling fins on the inside or outside of the plasma chamber can aid in convective heat transfer into the internal or external gas flow, respectively. Certain ceramics can provide substantially better heat conductive over commodity ceramics such as alumina or quartz. These specialty ceramics include but are not limited to beryllium oxide, aluminum nitride, and boron nitride.

In some embodiments, there are one or more partially- or fully circumferential grooves around a plasma chamber. Grooves can be used for O-ring seals to prevent cross-communication of reactant gas and product gas that would decrease flow through the plasma chamber. In some embodiments, the reactant gas inlet is aligned with the electrode gap to aid in directing reactant gas flow through the plasma. In some embodiments, the complexity of the manifold that houses the plasma chamber does not support alignment of the reactant gas port in the manifold with the reactant gas inlet in the plasma chamber. In some embodiments, this is addressed by having a first groove that can receive reactant gas from a surrounding manifold, and a second groove that delivers the reactant gas to the plasma chamber with both grooves in fluid communication by use of slots between the first and second groove to enable cross flow. In some embodiments, the width of a single groove is made wider, rather than having two grooves that are connected by a slot. The second groove can be located in a position so that an entry portal into the plasma chamber is located such that reactant gas is directed towards an electrode gap for maximizing NO production In some embodiments, spiral grooves on the exterior of a removable plasma chamber can pneumatically connect the reactant gas galley from the plasma manifold to the reactant gas entry point with the plasma chamber. In some embodiments, reactant gas flows from the plasma manifold galley to the chamber entry point. In some embodiments, the plasma chamber galley is aligned with the chamber entry point. Alignment of the chamber entry point to the electrode gap is another variable. In some embodiments, a reactant gas flow 400 enters into a plasma chamber through a reactant gas entry point 402 that is aligned directly with the electrode gap to maximize reactant gas/plasma interaction, as shown in FIG. 16A.

Figure 16B:
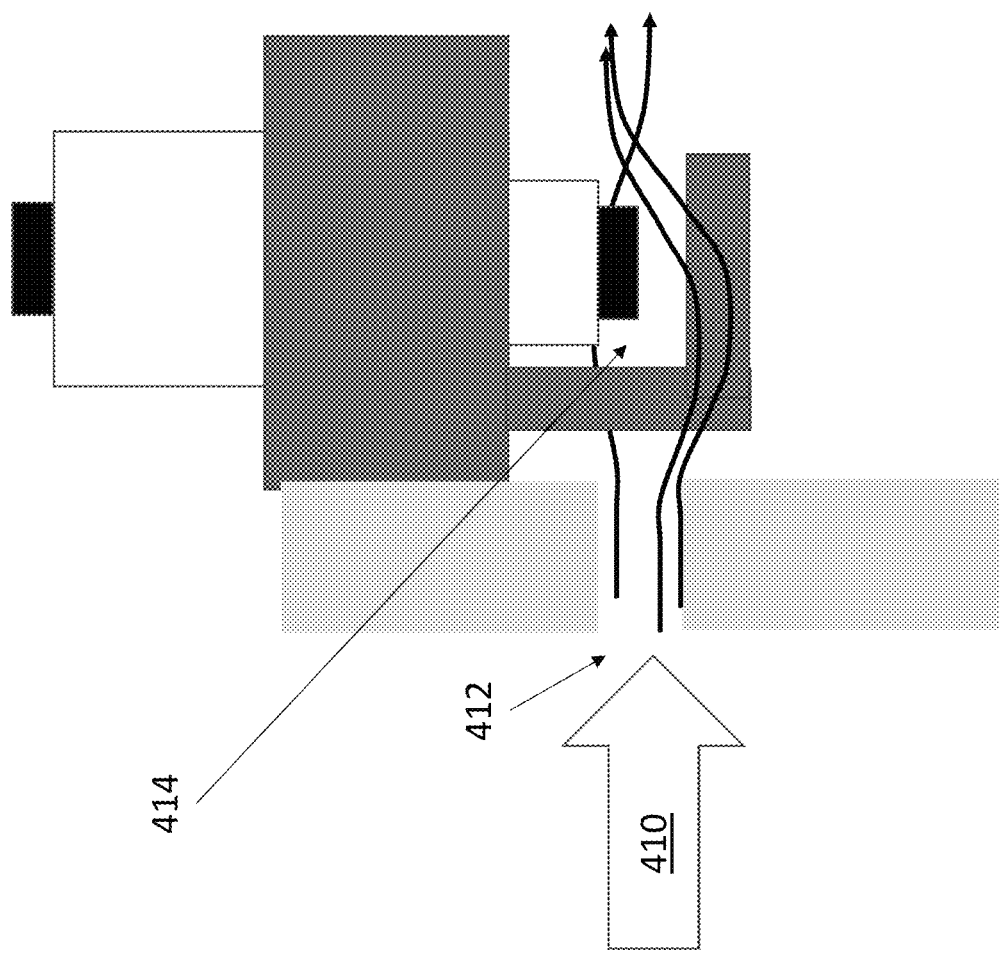

Electrodes in the form of a single-sided electrode pair, for example a J-shaped ground electrode, can generate a low-pressure zone 414 between the ground electrode and the center electrode. FIG. 16B illustrates a reactant gas flow 410 that can enter through the wall of the chamber through a reactant gas entry point 412, directed at the J-shaped electrode. The flow divides around the J-shaped electrode, creating a region of low pressure downstream of the J-shaped electrode. As materials sputter from the electrodes, this low-pressure zone can promote deposition of electrode materials which can lead to electrical creepage and ultimately reduced NO production. In some embodiments, the electrode ground electrode is rotated with respect to the reactant gas flow to be upstream but out of the reactant gas flow. For example, the ground electrode can be rotated 60% along its axis. This approach can prevent electrically conductive deposits between the center electrode and ground electrode while also enabling more consistent flow the plasma chamber across a range of flow rates.

In some embodiments, the plasma chamber can be in the form of a dome 420, as shown in FIG. 17A, FIG. 17B, and FIG. 17C. This approach is an example of one or more of the electrodes being part of the chamber wall. It provides a large surface area of electrode which prolongs electrode life.

Figure 18A:
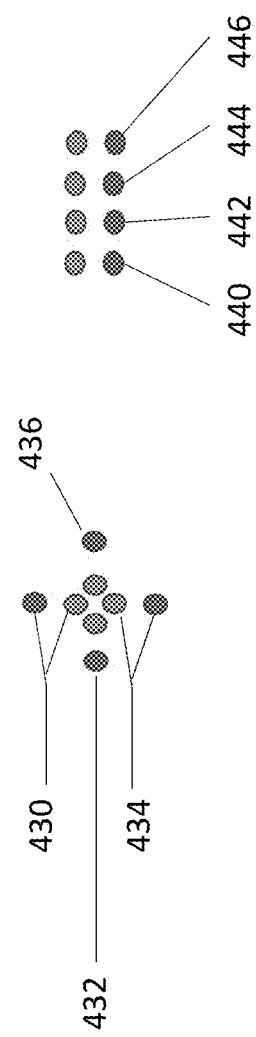
FIG. 18A, FIG. 18B, FIG. 18C, and FIG. 18D illustrate various embodiments of electrode arrays.
Figure 18B:
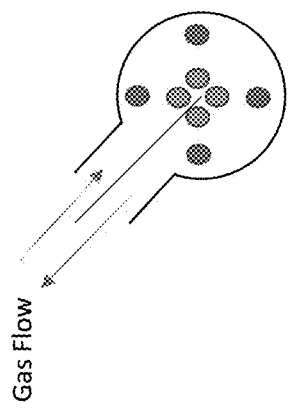
Figure 18C:
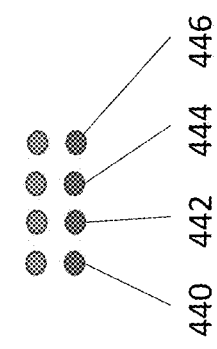
Figure 18D:
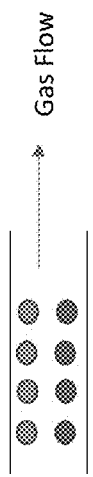

In some embodiments, an array of center electrodes arc to an array of outer electrodes. This approach provides redundancy and a way to shift heating so that no one electrode pair gets too hot. In some embodiments, pairs of electrodes are energized at a time, one inner and one outer. In some embodiments, all center electrodes are energized and outer electrodes are connected to close the circuit one at a time. Various embodiments of electrode arrays can be seen in FIG. 18A, FIG. 18B, FIG. 18C, and FIG. 18D. FIG. 18A depicts four electrode pairs 430, 432, 434, 436 where the inner four electrodes are at one polarity and the outer four electrodes are at the opposite polarity. FIG. 18C depicts a way of flowing gas through the electrodes shown in FIG. 18A. FIG. 18B shows four electrode pairs 440, 442, 444, 446 where the upper electrodes are at one polarity and the bottom electrodes are at the opposite polarity. FIG. 18D shows how air flow can be directed over all four electrode pairs. Electrode pairs can be energized as pairs. Alternatively, all upper electrodes could be energized, but only one bottom electrode is electrically connected so that arcing only occurs between one pair of electrodes.

Plasma Electrodes

Figure 19C:
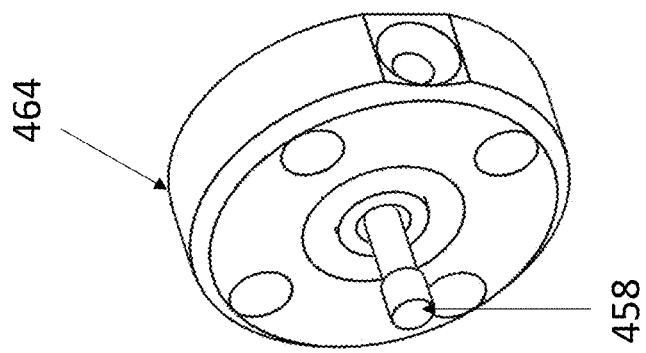

In some embodiments, the electrodes and plasma chamber of an NO generator are integrated into a single assembly. The one or more electrodes can be made from a single material, such as Iridium, or a composite. In some embodiments, a composite electrode is made from a titanium or tungsten substrate welded to an iridium tip. This approach offers the benefit of lower cost metal while still being weldable to iridium due to having a similar melting point. Electrodes are fixed into electrically conductive pucks that serve to transfer heat, anchor the electrodes in position at a specified electrode gap, and provide an electrical interface to a power supply. Pucks connect to a plasma chamber with sealed connections. In some embodiments, the seal between puck and plasma chamber employs an O-ring to seal in NO-containing gases. The plasma chamber can be made from ceramic, glass, high-melting point polymer, or a composite. In some embodiments, the plasma chamber is made from a polymer material with ceramic inserts in the region of the plasma chamber to prevent polymer melting. Reactant gas flow through the plasma chamber is directed towards the electrode gap for increased NO production and to direct any sputtered electrode materials away from the electrodes. In some embodiments, pneumatic fittings on either end of the plasma chamber consist of 90-degree angles so that the pneumatic openings are parallel with high voltage electrical connectors to enable connection of the plasma chamber and electrodes to an NO generator in a single motion. FIG. 19A, FIG. 19B, and FIG. 19C illustrate an embodiment of an electrode design including a plasma manifold 450, and air inlet 452, an air outlet 454, a pneumatic connection 456, and a plasma generation chamber 460 with controlled airflow for producing plasma 462. FIG. 19B shows a close-up view of an individual composite electrode 458 with a head that is larger in diameter and different material than the substrate shaft. In the embodiment shown, reactant gas flow is directed through a 4 mm nozzle to a 2.5 mm electrode gap. The nozzle terminates as it reaches the plasma chamber 460 and the internal diameter increase to 9 mm. This increase in diameter provides clearance between the electrode and plasma chamber and increases the surface distance/area between electrodes to prevent electrical creepage. FIG. 19C illustrates an embodiment of an opposing electrode assembly 464.

The relationship between nozzle size, electrode gap and spacing between nozzle and electrode gap have significant effects on plasma-gas interaction and resulting NO production. In some embodiments, a 1 mm nozzle is directed at a 0.5 mm gap. In this embodiment, high gas-plasma interaction results in a high level of NO conversion within the reactant gas. In some embodiments, a 2 mm nozzle is directed at a 0.5 mm gap. In this embodiment, less gas-plasma interaction results in low NO production levels, which can be advantageous in low NO doses. In some embodiments, a nozzle has variable size so that NO production can be optimized for a given treatment. In some embodiments, the orientation of the nozzle with respect to the electrode gap can be varied to adjust NO production. This can be accomplished by re-orienting a single nozzle or changing from a first nozzle to a second nozzle. In some embodiments, a first nozzle is aimed directly at an electrode gap and a second nozzle is parallel to a first nozzle but offset so that reactant gas passing through it is not directed towards the electrode gap. A system can choose between nozzles in a binary fashion or titrate between the two by means of a flow diverter or one or more proportional or digital valves.

In some embodiments, two or more independent pairs of electrodes are located within a single plasma chamber. This can provide electrode redundancy without added volume. In some embodiments, the two or more independent pairs of electrodes are configured like cross hairs in a gun site.

In some embodiments, a gas discharge tube is located in parallel with the electrode gap within the circuit. This provides protection to the system from excess voltage in the event of electrode failure. Electrical current, heat or optical emissions from the gas discharge tube can be used by the system to detect electrode failure.

The NO generation characteristics of sharp-edged solid electrodes can vary over their service life due to erosion of the sharp edges. In some embodiments, the electrode is constructed from a tube to ensure that there is always a relatively sharp edge at the end as it wears, ensuring consistent performance across its service life. This embodiment is also beneficial because it provides sharp edges provide high electric field strength.

Sharp edges on an electrode become rounded over time due to preferential arcing, resulting in a decreased electric field over the electrode surfaces. This decreased electric field at a given voltage can make arc formation take more time or fail to happen at all. In an NO generation device, longer or variable arc formation times can affect the stability of NO production and dose accuracy over time. In some embodiments, electrode edges are rounded during manufacturing to have a similar shape to a worn electrode. When this is done, higher voltage and longer duration are required to achieve breakdown within the gap, but those voltages and durations are more predictable over a longer period of time.

One way to increase the electric field in the proximity of the electrode gap is to concentrate electric field between the electrode and an insulator. In some embodiments, the electrode and plasma chamber are designed to increase electric field in the vicinity of the electrode when voltage is applied. In some electric field concentrator embodiments, the junction between electrode, reactant gas, and electrode insulator have one or more of the following parameters tuned to increase electric field strength in the vicinity of the electrodes: geometry, relative permittivity (i.e. dielectric constant), and other insulator material properties (susceptibility, polarizability, melting temperature). Increasing electric field strength can intentionally exceed the critical displacement (electric flux density) of the reactant gas, which will result in either partial discharge or corona, thereby generating free electrons that facilitate initiating a full discharge between the electrodes. This effect can be considered to be effectively a starter discharge that facilitates the generation of a larger arc. In some embodiments, the E-field concentrator is integral to the plasma chamber. A field concentrator can be made of a material with appropriate relative permittivity, such as ceramic, glass or polymer. In some embodiments, the field concentrator is made from alumina.

Figure 20:
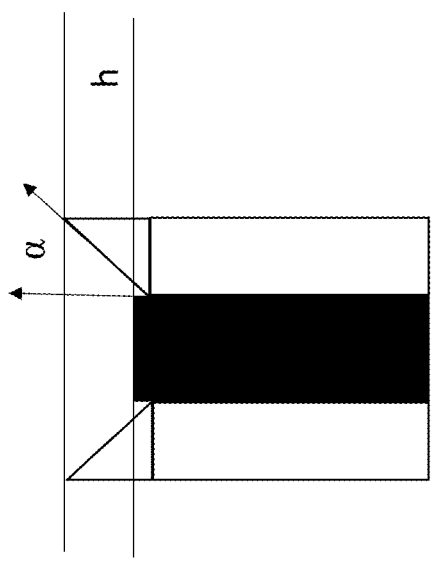
FIG. 20 depicts an exemplary insulator around an electrode.

FIG. 20 depicts an exemplary insulator around an electrode with "h," the height of the insulator with respect to the end of the electrode and "α," the angle between insulator and electrode. In some embodiments, "h" is between 0.1 and 0.5 mm and "α" is between 15 and 60 degrees to ensure that the electric field is concentrated while minimizing the impact to reactant gas flow. In some embodiments, a large angle α is used so that the angle remains in a functional range in the presence of carbon deposits. In some embodiments, a radial gap between the insulator and the electrode can create a local concentration of electric field.

The materials that form the insulator can vary. In some embodiments, electrode insulator materials have high chemical stability, high melting temperature and appropriate relative permittivity. In some embodiments, titanium dioxide is used to shape the electric field in the vicinity of an electrode gap. This material can be used as it is biocompatible and benign if it enters the patient airstream.

Electrical discharge for a given gap occurs at lower voltages when free electrons are available. Lower voltages are beneficial to an NO generation system because they decrease the potential for electrical discharge elsewhere in the system. In some embodiments, a specific class of materials release electrons more readily due to a low work function of the oxide layer. In some embodiments, pure yttrium oxide is used as a source of Schottky/Thermionic Emissions source. In some embodiments, yttrium partially stabilized zirconia can be used as a source of Schottky/Thermionic Emissions source. In some embodiments, barium titanate can be used as a very high relative permittivity (greater than 70 C/m2) and possibly Schottky/Thermionic Emission source.

Figure 21B:
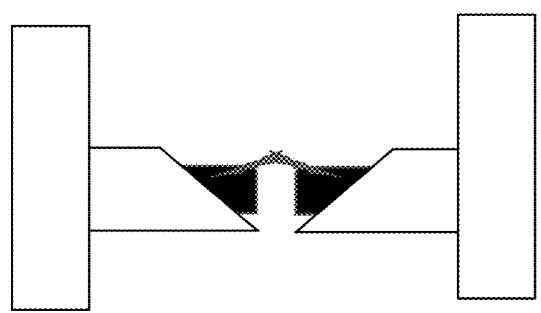
FIG. 21B illustrates the arc of FIG. 21A that has migrated across the surface of the electrode.
Figure 21A:
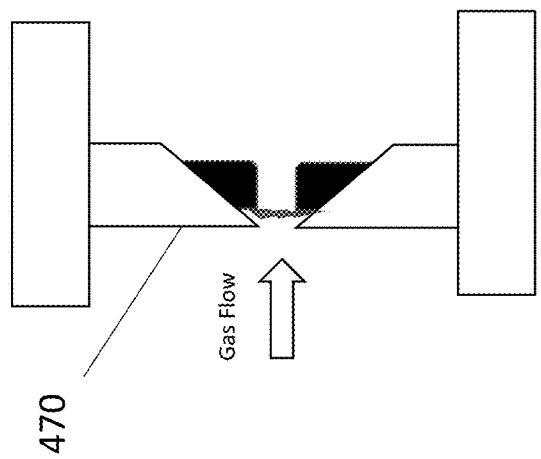
FIG. 21A illustrates an exemplary arc initiated on the upstream edge of the electrodes where electric field strength is high.

In some embodiments, an insulator 470 surrounds an electrode with a sloped end near the electrode gap, as shown in FIG. 21A and FIG. 21B. The tallest portion of the slope is located upstream in the reactant gas flow. The electric field is concentrated between the insulator and electrode at the upstream side, facilitating the breakdown of the gap in the presence of high voltage. The reactant gas flow directs the arc across the top of the electrode to the downstream edge as the arc is sustained. The insulator does not interfere with the arc on the downstream side because it is further from the electrode gap at that location. This approach enables the plasma to generate NO without interacting with the insulator material and potentially contaminating the plasma. In some embodiments, the insulator material is a ceramic. As shown in FIG. 21A, an arc initiates on the upstream edge where electric field strength is high due to proximity of the ceramic and electrode. As shown in FIG. 21B, the arc has migrated across the surface of the electrode and clings to the downstream edge of the electrodes. As shown, the arc has elongated due to the flow of reactant gas through the chamber.

Materials

Electrode performance is influenced by a variety of material properties, including but not limited to work function, melt temperature of the base material, and melt temperature of oxide layers (as applicable). NO generation electrodes can be made partially or wholly from graphite (carbon), carbon-carbon composite, glassy/vitreous carbon, iridium, tungsten, tungsten-silver alloy, hafnium, titanium, tantalum, barium, strontium, yttrium, lanthanum, and cerium. Copper, stainless steel, and electrically conductive ceramics (indium tin oxide (ITO), lanthanum-doped strontium titanate (SLT), yttrium-doped strontium titanate (SYT) can also serve as electrode materials. A substrate electrode can be plated with an ideal electrode material. For example, a titanium electrode can be plated with a noble metal such as Iridium. Alloys of more than one material can be used to leverage benefits of each constituent material. Biocompatibility of an electrode should also be considered due to the potential of electrode particles entering the inspiratory airstream.

TABLE 1

| Material | Overall Work Function | Base melt temperature | Oxide melt temperature |
| --- | --- | --- | --- |
| Titanium | Good | 1941K | 2116K |
| Hafnium | Good | 2506K | 3031K |
| Tantalum | Good | 3290K | 2145K |
| Glassy Carbon | Good | 3925K | |
| Stainless Steel 440c | Good | 1756K | |
| Tungsten | Good | 3695K | 1746K |
| Iridium | Poor | 2719K | 1370K |
| Barium | Excellent | N/A* | 2196K |
| Strontium | Excellent | N/A* | 2804K |
| Yttrium | Excellent | N/A* | 2698K |
| Lanthanum | Excellent | N/A* | 2588K |
| Cerium | Excellent | N/A* | 2670K |

*N/A because metal does not exist as base metal in the presence of oxygen.

In some embodiments, the electrode surfaces comprise a material with low work function, i.e. more readily releasing electrons. In some embodiments, an electrode substrate is coated with an oxide layer consisting of one or more of the following materials: alkaline oxide, barium oxide, strontium oxide, calcium oxide, aluminum oxide, or thorium oxide. In some embodiments, an electrode is coated with a boride-containing material, such as lanthanum hexaboride or cerium hexaboride to achieve a low work function. In some embodiments, the electrode contains an electron-emissive layer of thorium, zirconium dioxide, lanthanum oxide, yttrium(III) oxide, cerium(IV) oxide, and alloys thereof in the outer surface. In some embodiments, carbide materials provide a low work function on an electrode, such as zirconium carbide, tungsten carbide, hafnium carbide, and tantalum carbide. In some embodiments, the electrode material is selected from the group including: scandium, yttrium, gadolinium, lanthanides, samarium, hafnium, zirconium, and titanium). Tungsten, tantalum, molybdenum, and rhenium can also be used, owing to their high boiling point. In some embodiments, electrodes are made from a single-crystal manufacturing process. Single crystal materials can be beneficial because they do not have grain boundaries which are a common site for initiation of oxidation. By reducing the formation of oxides, which typically have a much lower melting temperature than their parent metal, the electrode erosion and NO production changes that result can be slowed.

Electrode Gap Adjustment

Figure 22:
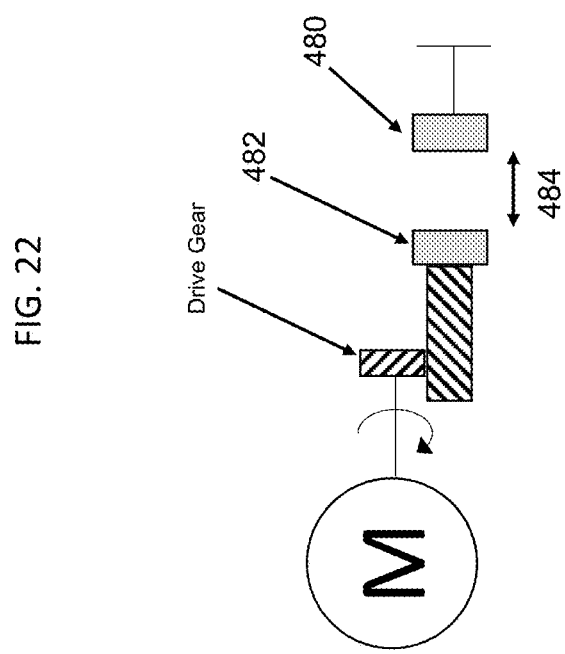
FIG. 22 illustrates an embodiment of a nitric oxide generation system that can adjust the electrode gap with a stepper motor.

In some embodiments, a nitric oxide generation system can adjust the electrode gap with a stepper motor, as shown in FIG. 22. The system can zero itself by running the electrodes together until they contact, then the stepper motor is operated to separate the electrodes by a known amount. This enables a system to accommodate for electrode wear. As shown in FIG. 22, a first electrode 480 can be fixed in position and a second electrode 482 can be movable such that a variable gap 484 exists between them. It will be understood that either or both electrodes can be movable to vary the size of the gap therebetween. In some embodiments, the electrode gap is varied to adjust the amount of NO produced and/or the $NO/NO_2$ ratio. Electrode gap adjustment can be made before NO generation and/or during NO generation. In some embodiments, the relationship between gap size and NO production at various input powers and flow rates is thoroughly characterized, enabling a controller to adjust the gap to achieve desired NO production levels during therapy.

It is possible for the system to vary the electrode gap to vary NO production and make up for worn electrodes. In some embodiments, a brush can make contact with the electrode. The electrode is mounted in a non-electrically conductive shaft that can be translated (or rotated) away from another electrode. Motion of the electrodes can be manual or by motor. In some embodiments, the electrodes are moved towards each other to establish zero gap and then moved apart a known amount. For example, possible ranges for the electrode gap are from 0.1 mm for low productions, up to 5 mm for high productions. This would establish a known zero-point, enabling the device to compensate for an offset change the latest calibration due to electrode wear. The movable electrode length could be designed so that several millimeters of electrode wear may be anticipated and accommodated over the service life of the device. In this manner, a substantially longer-life electrode can be created.

In some embodiments, an electrode assembly is disposable, lasting hours to days. This enables a lower cost material to be used, such as copper, titanium.

In some embodiments, electrodes are mounted in materials that have a coefficient of thermal expansion to minimize stress in components during thermal cycling. For example, for iridium and titanium electrodes, alumina has similar coefficient of thermal expansion.

Plasma Chamber Design

An NO generator plasma chamber has many requirements. The chamber must be gas-tight, preventing the loss of reactant and product gases. The chamber must locate electrodes in a consistent manner. The chamber must direct reactant gas towards the electrodes in a predictable manner. The chamber must prevent electrical shorting between electrodes other than within the electrode gap. This last requirement can present a challenge to designers when electrical creepage is considered. Electrical creepage is the phenomenon whereby electricity travels along the surface of a material. The distance in which electricity will creep depends on many factors, including but not limited to the distance between conductors, material type, material cleanliness, and voltage applied. In an NO generator, electrical creepage between electrodes would prevent electrical breakdown within the electrode gap and plasma formation. Thus, it is important to prevent electrical creepage within the plasma chamber. In some embodiments, undulations in the wall of the plasma chamber increase creepage distance.

As electrodes wear, there is a potential for electrically conductive electrode material to sputter onto the internal surfaces of a plasma chamber, changing the conductivity of plasma chamber walls and decreasing the voltage required to cause electrical creepage. One benefit to using undulations within the plasma chamber walls is that valleys are less likely to be coated with conductive deposits such as iridium-oxide or carbon.

In some embodiments, a plasma chamber is insulated to maintain a high temperature, thereby increasing the NO to $NO_2$ ratio. In some embodiments, the reactant gas is actively heated prior to the plasma chamber and/or within the plasma chamber.

Plasma chambers can be made from a variety of materials. In some embodiments, ceramic is used for its electrical resistance and thermal conductivity (for example, alumina nitride with a k=140-180 W/mK). In some embodiments, a high temperature polymer is used for its lower cost to ceramic, electrical resistance, chemical resistance, and light weight. Examples of a suitable polymer are PEEK, Ultem, PVDF, FEP, and PTFE.

Polymer materials can be susceptible to melting due to plasma temperatures. In some embodiments, the plasma chamber includes ceramic inserts to insulate chamber material from high temperature electrodes and/or plasma.

In some embodiments, a plasma chamber recycles heat from the product gas exiting the chamber to the inlet gas stream for the purpose of increasing $NO:NO_2$ ratios.

In some embodiments, a plasma chamber recycles heat from the exhaust gas to the inlet gas stream for the purpose of cooling the outlet gas stream to a manageable temperature for downstream seals, valves, scrubber materials or sensors.

In some embodiments, a plasma chamber is provided that removes heat from the exhaust gas so as to "quench" the NO and prevent formation of $NO_2$. This can be accomplished by passing outlet gas through geometry which facilitates heat exchange to another air flow (for example, flowing over fins, or splitting flow over many smaller diameter tubes).

A plasma chamber can incorporate a heat exchanger to actively transport thermal energy from one manifold element to another. In some embodiments, a heat exchanger cools the outlet gas stream and moves the heat into the inlet gas stream. In some embodiments, a heat exchanger can cool electrodes and heat an inlet gas stream. In some embodiments, a heat exchanger can heat electrodes and cool an outlet gas stream. In some embodiments, the heat exchanger can be a Peltier device. In some embodiments, the head exchanger uses compression and expansion of a coolant gas. In some embodiments, the heat exchanger involves the pumping of a liquid. In some embodiments, heat transfer between components relies on thermal contact and conduction through thermally conductive materials (for example, aluminum or copper). In some embodiments, copper electrodes are plated with iridium in the region of arcing. This provides excellent electrical thermal conduction of copper and high melting temperature and electrically conductive oxides of iridium.

In some embodiments, a plasma chamber can use reactant gas flow velocity to create an elongated beam of plasma as a means of controlling of NO production.

Figure 23:
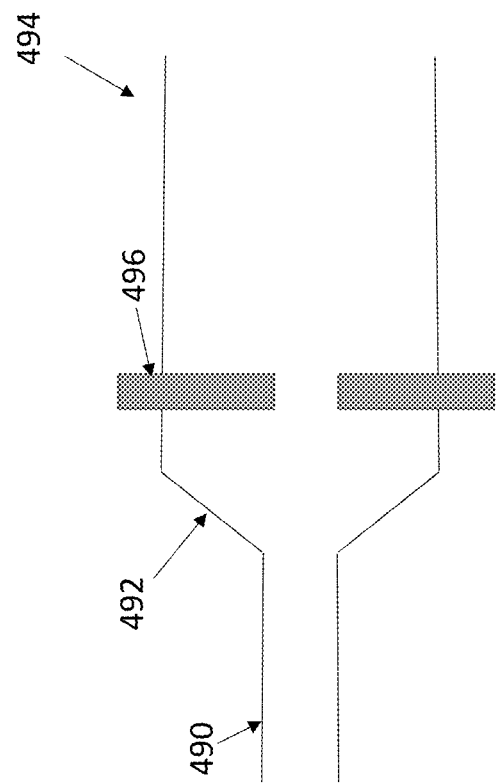
FIG. 23 is an exemplary plasma chamber design including a nozzle end, a flare, and a chamber.

In some embodiments, a plasma chamber design can include a nozzle end 490, a flare 492, electrodes 496, and a chamber 494, as shown in FIG. 23. The nozzle diameter is centered with the electrode gap and sized to produce a desired reactant gas velocity at the electrodes for a specific volumetric/mass flow rate. The flare increases the diameter of the chamber, thereby increasing the electrical creepage distance from one electrode to another.

Figure 24B:
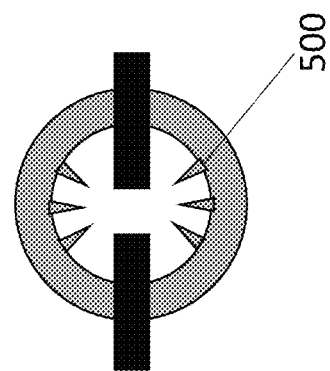
FIG. 24B illustrates an exemplary embodiment of a plasma chamber having surface features within the chamber.
Figure 24A:
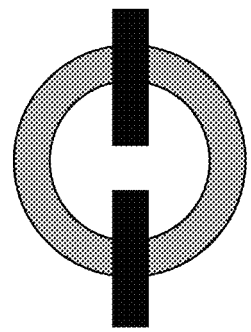
FIG. 24A illustrates an exemplary embodiment of a plasma chamber having surface features within the chamber.

Creepage distance within the plasma chamber can be increased further by adding surface features, such as ridges, valleys or splines within the chamber, as shown in FIG. 24A and FIG. 24B (which includes a plurality of splines 500 inside the chamber). Because the junction between electrode, air, and insulator typically results in a locally intense electric field, arcs often appear to run along the surface of an insulator—so adding features to increase that length makes the distance function more like an equivalently sized gap, not aided by the increased electrode.

Figure 25:
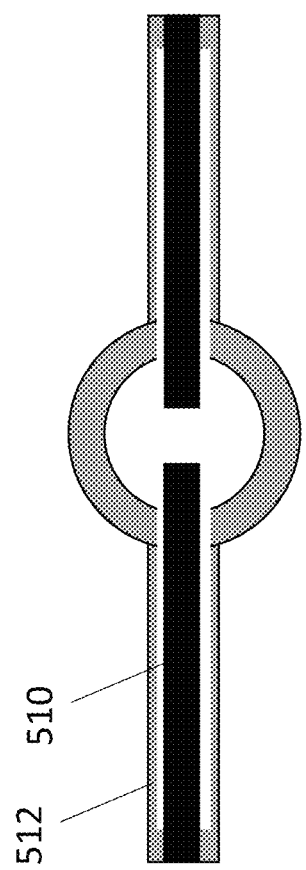
FIG. 25 is an exemplary plasma chamber having an electrode within a non-conductive tube with a clearance.

Creepage distance within the plasma chamber can be increased further by locating the electrodes 510 within a non-conductive tube 512 with a clearance, as shown in FIG. 25. This can prevent sputtered electrode materials from shorting the path between electrodes because materials cannot sputter down into the tubes.

Figure 26B:
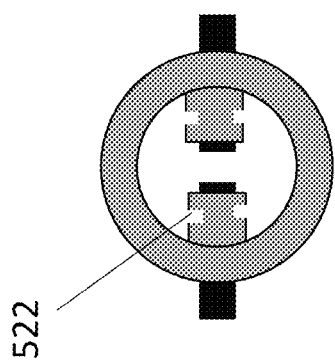
FIG. 26B illustrates an exemplary embodiment of an electrode insulator having ridges to shield a portion of a plasma chamber wall from sputtered electrode materials.
Figure 26A:
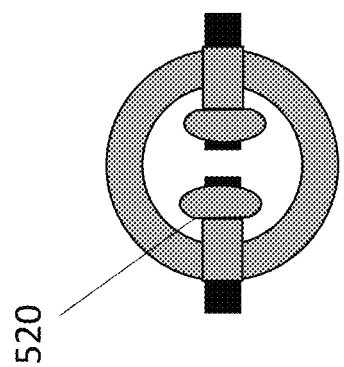
FIG. 26A illustrates an exemplary embodiment of an electrode insulator having grooves to shield a portion of a plasma chamber wall from sputtered electrode materials.

Creepage distance can be increased by shielding a portion of the plasma chamber wall from sputtered electrode materials, as shown in FIG. 26A and FIG. 26B. In some embodiments, surface features 520, 522, such as grooves or ridges, in an electrode insulator provide creepage distance in addition to protection from sputtered materials.

Figure 27:
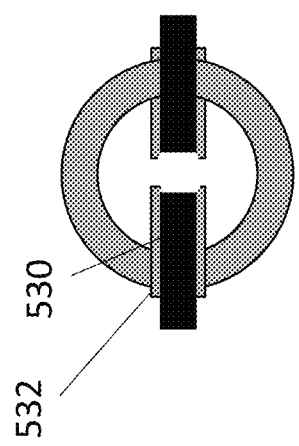
FIG. 27 illustrates an exemplary embodiment of an electrode recessed within an insulator.

In some embodiments, an electrode 530 can be recessed within an insulator 532 to shield the chamber from sputtered electrode materials, as shown in FIG. 27. This feature can also provide enhancement of the electric field at the electrode/insulator interface to decrease the voltage required to initiate plasma in the electrode gap.

Gliding Arc

In some embodiments, a gliding arc design can be used. A gliding arc electrode design can include two or more electrodes with elongated surfaces. The surface can be parallel or diverging with respect to the direction of reactant gas flow. This type of design offers benefits in electrode longevity because plasma is carried by the flow along the surfaces of the electrodes, thereby distributing electrode wear over a greater surface area, decreasing the electrode surface temperatures and erosion. Gliding arc electrodes have a range of electrode gap and can provide a small gap to improve the reliability of initial electrode breakdown. This offers benefits in lower voltage being required to initiate the arc. Gliding arc also offers the potential to decrease the back pressure associated with flowing gas through plasma since the arc can travel with the air flow. The duration of an individual arc can be limited by the voltage applied to the electrodes, the duty cycle, and/or the gas flow rate. In some applications, it is possible to extinguish an arc before it reaches the far end of the electrode where the arc elongates and NO production is less precise. A gliding arc design can be used in the field of NO generation because 1) arcing occurs over large surfaces of the electrodes, decreasing temperatures and decreasing electrode wear, 2) The initial gap can be very short to initiate the arc with low voltage, thereby decreasing the potential for arcing elsewhere in the system, 3) NO production can be very high due to the large gap that can occur with long duty cycles, 4) NO production can be continuous (duty cycle=100%), and 5) NO production can be very low with fine resolution, owing to the small gap.

In some embodiments, a gliding arc design includes electrodes constructed from monolithic blocks with edges that diverge. As arcs travel along the length of the electrode edges, the velocity of the arc slows due to the increasing cross-sectional area. This can produce more NO as the arcs spend more time at long lengths. In some embodiments, the length required for gliding arc electrodes is determined by the reactant gas flow rate through the plasma chamber, maximum voltage available and the maximum duty cycle. The length and surface profile of the gliding arc can be tuned to a particular flow rate and duty cycle/period, so as to clear all electrons & ions from the chamber during the "off-time" of the plasma. A desired NO output curve can create by setting the electrode's angle of divergence. If a single angle represents a linear equation, then a polynomial, exponential, power, log or any other type of function, including a combination of functions, can be utilized to create a desired NO output curve.

Figure 28:
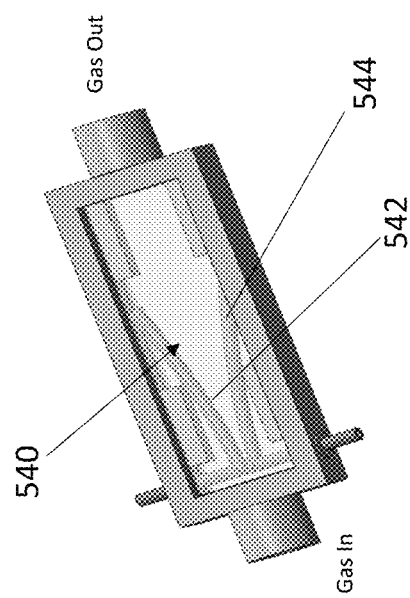
FIG. 28 illustrates an embodiment of a gliding arc electrode design constructed from bent rods.
Figure 29B:
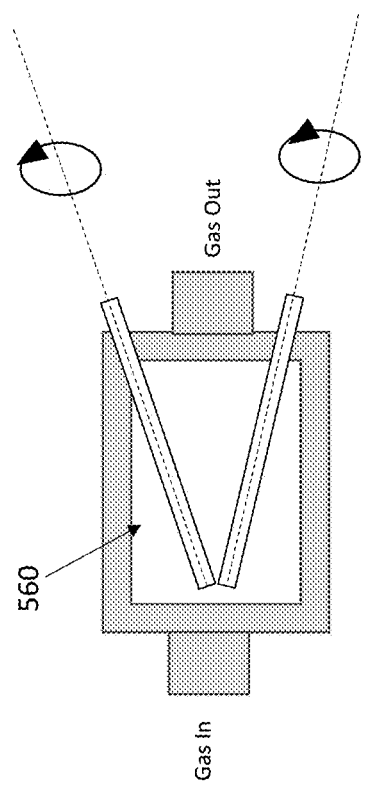
FIG. 29B illustrates an embodiment of a gliding arc electrode design constructed from straight rods.
Figure 29A:
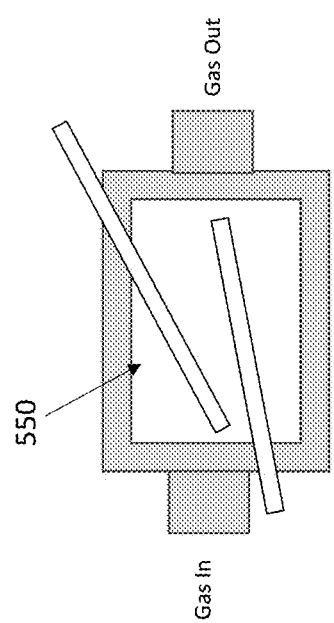
FIG. 29A illustrates an embodiment of a gliding arc electrode design constructed from straight rods.

The electrodes of a gliding arc design can be constructed from bent rods or straight rods. One benefit of straight rods is ease of insertion into the plasma chamber. When rods (such as rods 542, 544 shown in FIG. 28) are inserted from opposite ends of a plasma chamber 540, 550, 560, as shown in FIG. 28, FIG. 29A, and FIG. 29B, there is significant creepage distance between electrodes. In some embodiments, straight electrode rods can be rotated about their long axis periodically to align a new surface with the electrode gap, thereby prolonging the useful life of a particular electrode. Curved arrows in the FIG. 29B depict this rotation.

Figure 30:
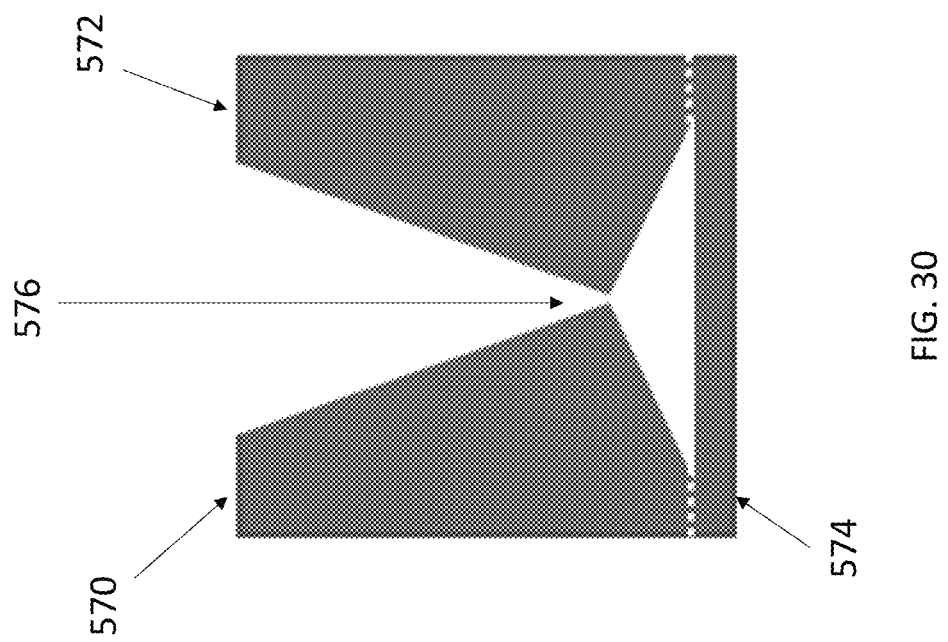
FIG. 30 is an exemplary embodiment of two gliding arc electrodes cut into sheet metal.
Figure 31:
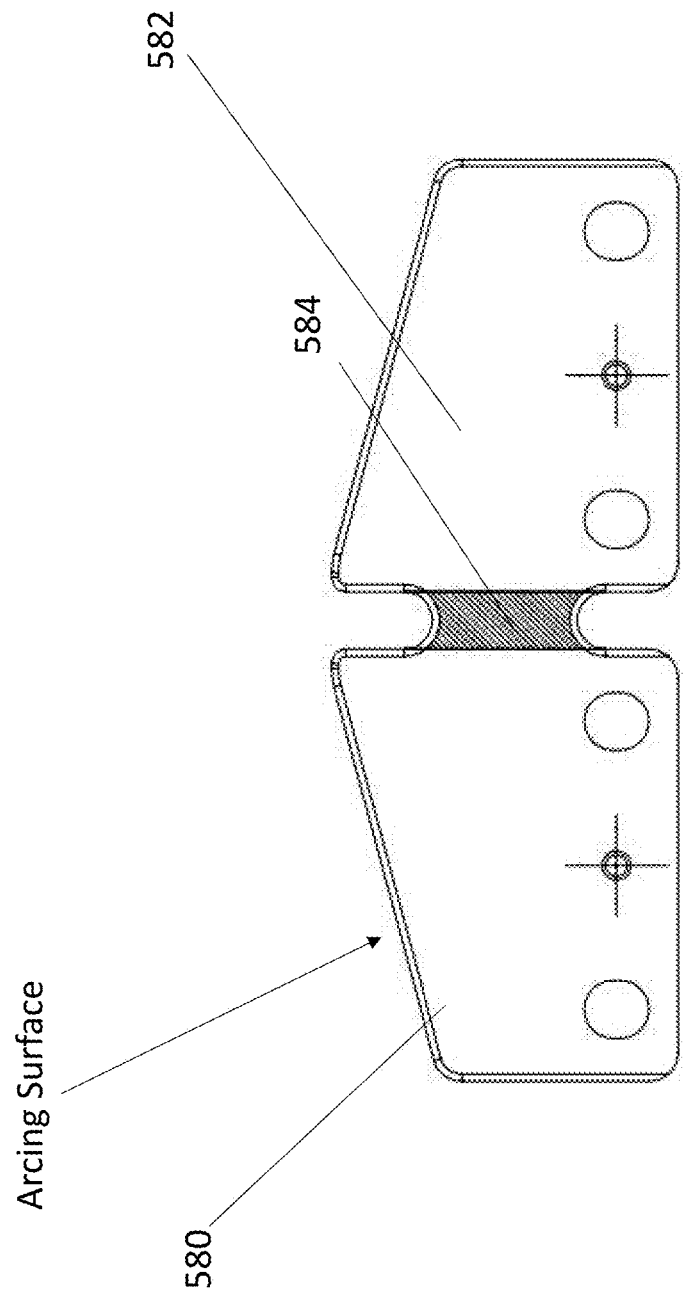
FIG. 31 is an exemplary gliding arc electrode pair design that is machined from a single piece of material.

The electrodes of a gliding arc can be constructed from sheet metal where the edge of the sheet metal serves as the arcing surface. This edge can be rounded, as needed, to make electrode performance more consistent over time. It will be understood that the edges of the gliding arc electrodes can be, but do not need to be, straight. In some embodiments, sheet metal is cut to contain two, opposed gliding arc electrodes 570, 572 held at a correct gap 576 by one or more metal tabs 574, as shown in FIG. 30. After installation of the electrodes into the plasma chamber, the one or more metal tabs can be broken off the assembly, leaving the two gliding arc electrodes electrically independent. In some embodiments, a pair of electrodes is machined from a single plate of material to ensure that chamfering of the edges is the same for each electrode. The final machining step is to separate the electrodes so they can be independently mounted to the plasma chamber. FIG. 31 depicts an embodiment of an electrode design made from sheet material. The upper edges of the electrodes 580, 582 are chamfered to present a sharper edge to the electrode gap. An area 584 is removed as a final machining step to separate the two electrodes.

A gliding arc electrode plasma chamber can operate at a full range of duty cycles. In some embodiments, a gliding arc plasma chamber can be designed to operate at a low duty cycle due to the small electrode gap that can exist between the gliding arc electrode pair. This can allow for lower amounts of NO to be generated. In some embodiments, a gliding arc plasma chamber is designed to operate at high duty cycles (for example, 50 to 100%). This can allow for a longer electrode life due to distributed wear along the length of the electrodes. It also provides continuous NO production when 100% duty cycle is utilized.

The initial gap and angle between gliding arc electrodes are a critical design features of a gliding arc design for nitric oxide generation. Smaller gaps enable lower production levels due to the shorter length arcs and decreased gas/plasmas interaction. In some embodiments, the small gap is 0.5 mm in length, however lengths up to 2.5 mm have been utilized. In some embodiments, the angle between electrodes is 30 degrees. In some embodiments, angles of 20 to 40 degrees have been utilized. In some embodiments, angles of 0 to 75 degrees can be used. Arcs travel along the length of the gliding arc electrode due to gas flow. Larger angles between electrodes result in more rapid elongation of the arc and higher production levels for a given electrical discharge duration. It follows that the interaction between electrode angle and gas flow rate is important in specifying a gliding arc electrode design for a specific range of NO production. When gas flow is low, an arc may not glide at all. If the electrode gap increases to rapidly (steep angle), the gas flow could extinguish the arc before the end of the high voltage pulse. In the event of premature extinguishing of the arc, an arc will reform at the small gap and continue generating NO until the end of the high voltage pulse, albeit at a smaller gap and correspondingly lower production levels. This can create a discontinuity in NO production which is typically avoided. In some embodiments, a NO generation system can detect premature extinguishing of the arc and truncate the duration of the arc to protect against applying high levels of current to the small gap. In some embodiments, a NO generation system can detect premature extinguishing of an arc and reset current modulation within the arc for an appropriate level of the small gap. In some embodiments, a NO generation system can detect premature extinguishing of an arc and restarting of the arc at the small gap and prolongs the duration of the arc so that the NO production for that electrical discharge remains on target.

In some embodiments, an NO generation system can detect premature extinguishing of the plasma during a discharge by detecting discontinuities in either the plasma voltage, plasma power or both. In some embodiments, premature extinguishing of the plasma arc can be detected as a discontinuity in the plasma light output using an optical sensor. In some embodiments, the optical sensor is directed towards the small gap region of a gliding arc electrode. In some embodiments, the optical sensor can view the electrode gap through a optically transparent window, such as a quartz window.

Electrical field strength is higher in the small gap region of a gliding arc electrode. For a fixed current in the plasma, this contributes to higher energy density in the small gap than other locations along the length of the gliding arc electrode. High energy density is associated with increased temperature and sputtering of electrode materials, which corresponds with higher levels of electrode erosion in the small gap region of a gliding arc electrode. Because the voltage is set by the gap, modulation of power density must be accomplished by modulation of the plasma current. In some embodiments, current applied to the plasma is modulated within an electric discharge event to minimize energy density within the electrode gap. This approach offers two significant benefits: 1) Electrode erosion is lessened and 2) lower NO production levels can be achieved.

The orientation of the gliding arc electrode can have an effect on gas production. For example, gliding arc electrodes can produce additional gas that can travel further when oriented vertically. In some embodiments, a system can use an orientation sensor to compensate for differences in NO production based on the orientation of the system.

In some embodiments, an NO generation system can truncate the duration of an electrical discharge in the event that the arc extinguishes prematurely.

Figure 32C:
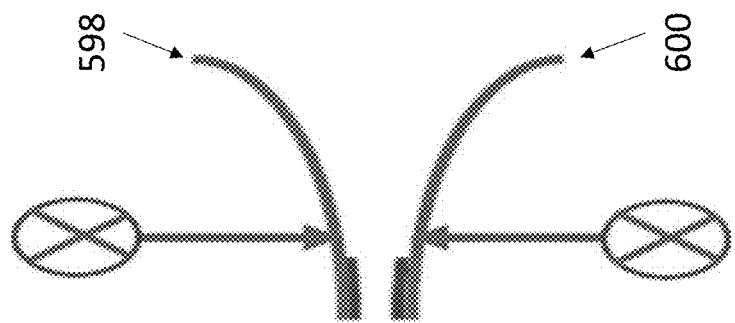
FIG. 32A, FIG. 32B and FIG. 32C depict embodiments of gliding arc electrodes constructed from more than one material.
Figure 32B:
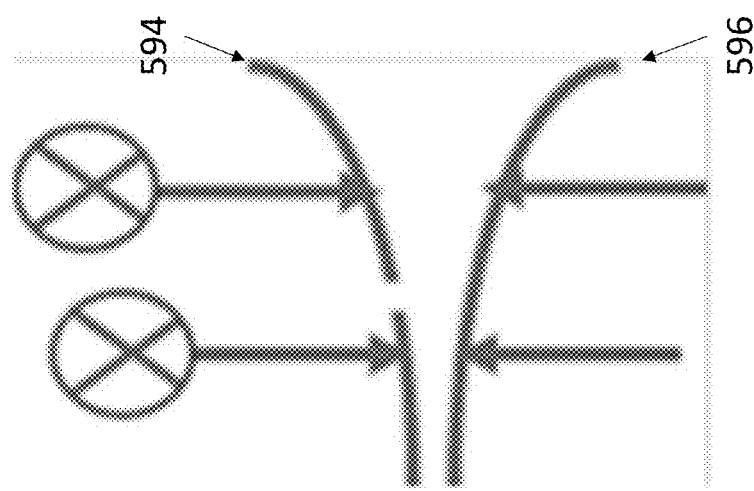
Figure 32A:
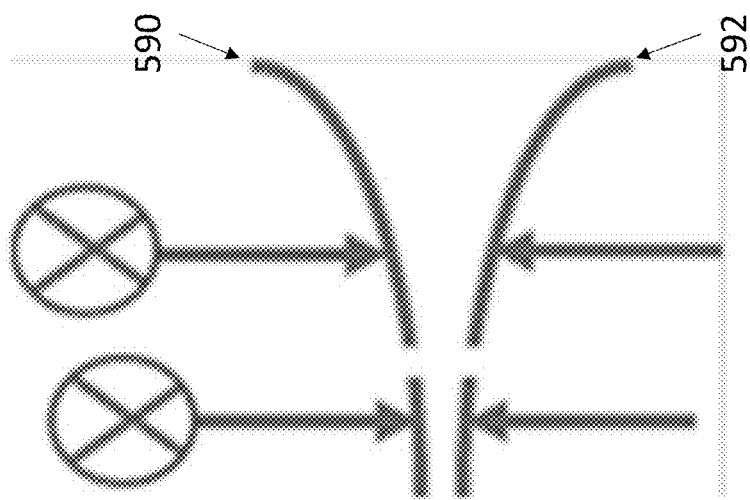

In some embodiments, a gliding arc electrode is constructed from more than one material. In some embodiments, a high melting temperature/high cost electrode material is used in the small gap region and a lower cost material is utilized in the large gap region. FIG. 32A depicts an embodiment including 590, 592 having two electrode materials located in series. FIG. 32B depicts an embodiment where only one side of the gliding arc electrode pair 594, 596 is a composite. This can be used in DC current systems where further cost reduction can be achieved by only using high melting point/high cost material at the cathode. FIG. 32C depicts an embodiment in which gliding arc electrode pair 598, 600 is plated/coated/shielded by a higher melting point material in the short gap region.

In some embodiments, multiple electrode pairs are stacked within a plasma chamber. The NO generation controller can selectively energize one or more electrode pairs at a time. In some embodiments, the system exhausts one electrode pair prior to using the next and so-on. Each electrode pair may have a dedicated nozzle, or they can share a common nozzle. In designs with multiple nozzles, the system can flow through reactant gas through all nozzles at the same time, or a subset of the nozzles at one time. In some embodiments, only the nozzle(s) associated with active electrodes flows reactant gas at a time. In some embodiments, a nozzle that is not associated with the active electrode is utilized to reduce NO production due to decreased plasma/reactant gas interaction.

With every electrical discharge, NO is formed. Making copious amounts of NO is a function of gap, gas/plasma interaction and energy density and is straight-forward. Making low levels of NO is a challenge, however, because there are practical limits to how short an electrical discharge duration and gap length can be. Lower levels of NO generation can be achieved by 1) decreased gap, 2) decreased gas/plasma interaction, and 3) decreased energy/current within the gap.

In some embodiments, a nozzle size and orientation with respect to the electrodes (location and angle) is selected to achieve the desired range of NO production. In some embodiments, the degree of gas/plasma interaction is modulated as a way to vary NO production and achieve low levels of NO production. This can be done by varying one or more of the nozzle diameter, nozzle location, nozzle quantity and nozzle orientation. In some embodiments, a plasma chamber has two nozzles. A first nozzle is directed towards the electrode gap for high efficiency in generating NO within the reactant gas. A second nozzle does not flow reactant gas directly towards the electrode gap so that a lower portion of the gas interacts with the plasma. A NO generation system varies the proportion of flow going through each nozzle to modulate the level of NO production to low levels.

In some embodiments, electrodes are located in a low-pressure zone within a plasma chamber or in an eddy of the reactant gas flow to reduce the plasma-reactant gas interaction and produce less NO.

Figure 33:
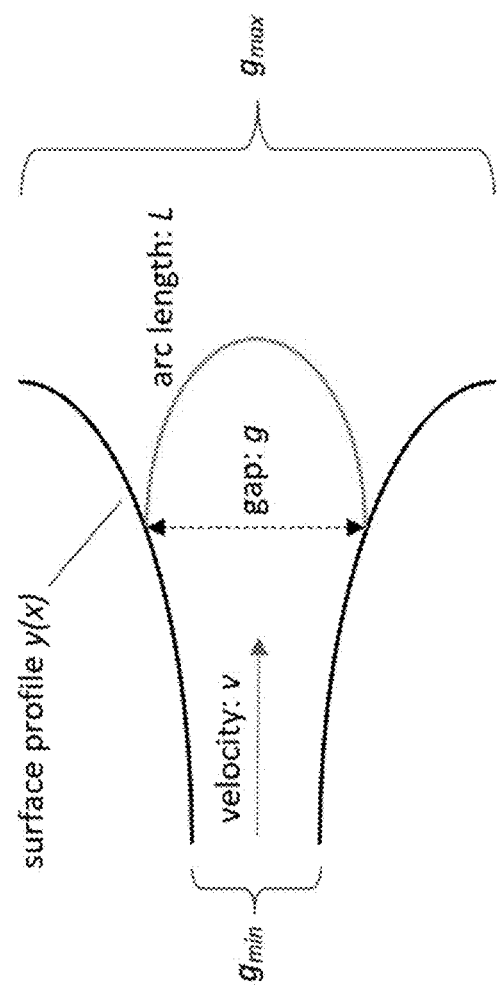
FIG. 33 illustrates an exemplary gliding arc electrode surface profile.

In some embodiments, a gliding arc electrode surface profile can create a constant arc length growth rate, facilitating stable control of arc length as a function of pulsation duration, as shown in FIG. 33. This can be accomplished by maintaining a relatively constant dL/dx across all range of duty cycles, where X is the horizontal direction in FIG. 33 and L is the arc length (not the gap) as depicted in FIG. 33.

In a gliding arc configuration, as the arc travels across the electrode surface, it will bend/stretch as a function of the velocity and input power. Because NO production is a function of effective arc length, it is possible that NO production does not change linearly or predictably as pulsation duration changes. To compensate for this, the profile of the electrode may be tuned to a chamber dimensions and flow rates to ensure linear, controllable NO production as a function of pulsation duration. The chamber dimensions, flow rate, and pulsation duration (proxy for input power) can be balanced by considering the gliding arc NO production as an integrator—knowing that at some point in the direction of flow, the surface profile has a gap, which along with a given velocity and input power creates an effective arc length, creates a certain level of NO production. By quantifying the relationship of all of these variables, it is possible to create a surface profile with a linear NO production response for a change in pulsation duration.

In some embodiments of the gliding arc electrode, the chamber dimensions, flow rate, and pulsation parameters are balanced such that the resulting velocity moves the plasma arc the desired distance for a given pulsation duration.

In some embodiments, a gliding arc design incorporates electrodes with wires sufficiently thin that they do not alter the reactant gas velocity in the region of the electrodes. This approach in concert with a constant cross-section plasma chamber can promote constant gas flow through the plasma chamber to facilitate modeling and NO production control.

In some embodiments, a gliding arc design includes electrodes that have sufficiently thin wires so that any mass erosion will electrically isolate the shortest gap area of the electrode, resulting in a detectable failure (input current will be substantially higher).

In some embodiments, a gliding arc design can be used for continuous plasma generation (for example, not pulsed, 100% duty cycle). In some embodiments, a system of continuous plasma generation varies one or more of duty cycle of an AC waveform, AC voltage, AC current and AC power to vary NO production. When an AC voltage peak is limited, the length of the arc may be controlled, thereby controlling production of NO.

In some embodiments, a gliding arc electrode is used to generate NO generation with DC voltage. In some embodiments, the material for each electrode may be selected for their suitability for cathode and anode applications.

In some embodiments, the output of a gliding arc electrode may vary with respect to its orientation with respect to gravity. This effect is more noticeable at slow reactant gas flow rates where the effects of hot air rising contribute a larger component to plasma gas motion. In some embodiments, a NO generation system uses its orientation sensor to compensate for differences in NO production related to the device orientation with respect to gravity. In some embodiments, the orientation sensor is a 3-axis accelerometer.

In some embodiments, a gliding arc plasma reactor is presented which produces a desirable amount of nitric oxide for treatment of hypoxic respiratory diseases. The amount of NO can be controlled by the flow and electrical parameters of the plasma source. The feed gas is ambient air which mainly includes oxygen and nitrogen.

Figure 34:
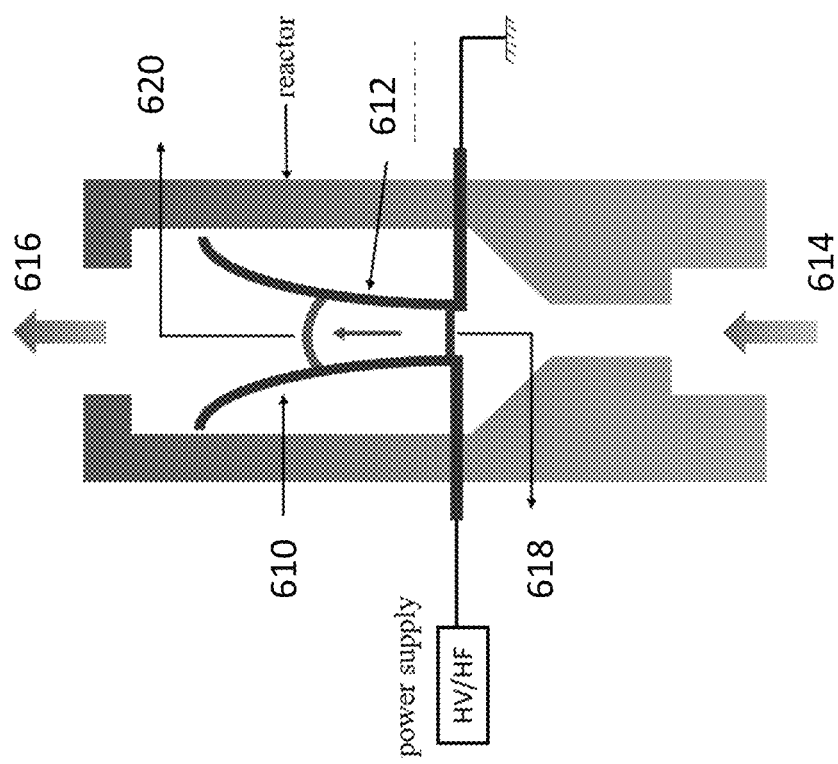
FIG. 34 illustrates an exemplary embodiment of a gliding arc plasma source.

Gliding arc plasma is a periodic plasma, generated between two diverging electrodes, including a powered electrode 610 and a ground electrode 612 as shown in FIG. 34 which illustrates an exemplary embodiment of a gliding arc plasma source. The reactant, or working, gas flows from the gas inlet 614 to the outlet 616. By applying high voltage to the electrodes, an initial arc 618 is initiated in the narrowest gap and glides between electrodes by the gas flow, toward the downstream of the reactor. As the arc glides between diverging electrodes, its length increases (shown as gliding arc 620) which causes enhancement of voltage and power consumption. The arc extinguishes at downstream, when the power supply cannot provide the required voltage to sustain the arc. The arc will be reignited in narrowest gap and a new arc movement cycle will be started.

In a gliding arc plasma source, the arc carries the gas toward the downstream till the arc extinguishes and a new cycle will be generated. Therefore, in this case the gas residence time in plasma volume is more than the one in conventional arc discharge configuration which can result in more NO production. In addition, as the arc length grows between electrodes, the power deposited inside the plasma increases which can result in higher electron temperature inside the plasma and consequently higher NO production. The gliding arc can also be used due to the convective heat loss of the plasma as the gas pushes the gas along the electrodes. The lower gas temperature in plasma in fixed electron temperature (fixed power deposited) causes the reduction of $NO_2$ production while the NO production can remain at the high value. It is because the high temperature plasma gas can favor the reaction of NO and $O_2$ or O to generate $NO_2$.

The main problem of conventional arc discharge plasmas (free burning opposed electrode arc) to generate the NO, is electrode erosion. In conventional arc discharge, plasma is always attached to the electrode on a tiny surface called electrode spot. The high heat flux from plasma to the electrode spots can cause electrode wear. In gliding arc plasma, the electrode spots move along the surface of the diverging electrodes which reduces electrodes erosion, significantly.

In gliding arc technology, voltage can either continuously or partially be applied to the electrodes. Power deposited in plasma can be adjusted by varying the voltage and duty cycle. The voltage and duty cycle flexibility in this system can provide a wide range of power deposited inside the plasma from 5 to 50 W, which leads to 2-8000 ppm·lpm of NO production. Increasing the power can increase the overall plasma volume in one period of gliding operation, meaning that in higher power, gas has more time to be placed inside the plasma. Therefore, a wide range of power operation results in a wide range of NO production.

Figure 35:
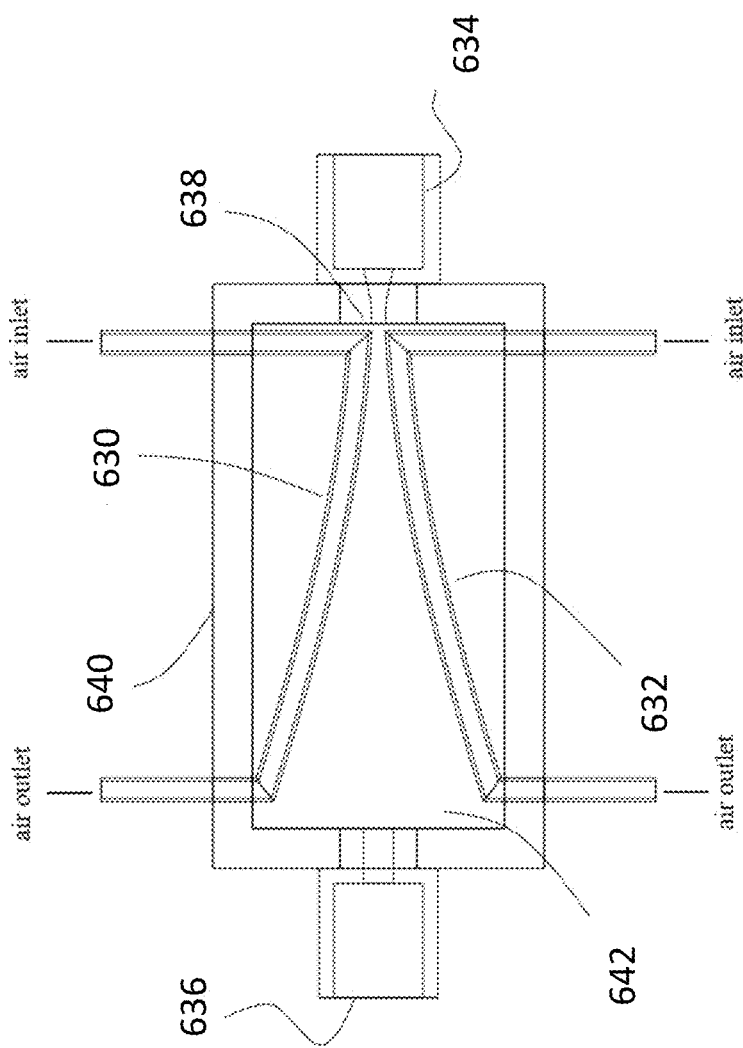
FIG. 35 illustrates an exemplary cross-sectional view of a gliding arc plasma source.

FIG. 35 illustrates an exemplary cross-sectional view of a gliding arc source. It includes two diverging hollow electrodes 630, 632, a gas inlet 634, a gas outlet 636, a nozzle 638 and a reactor body 640. The electrodes are placed between two quartz plates 642, i.e. electrodes are sandwiched between quartz plates. The benefit of this design is that all the gas inlet is forced to path between the electrodes and placed inside the plasma arc, instead of circumventing the arc. It enhances the efficiency of the process. FIG. 35 illustrates an exemplary cross-sectional view of a gliding arc plasma reactor. Gas flows from right to left.

Figure 36:
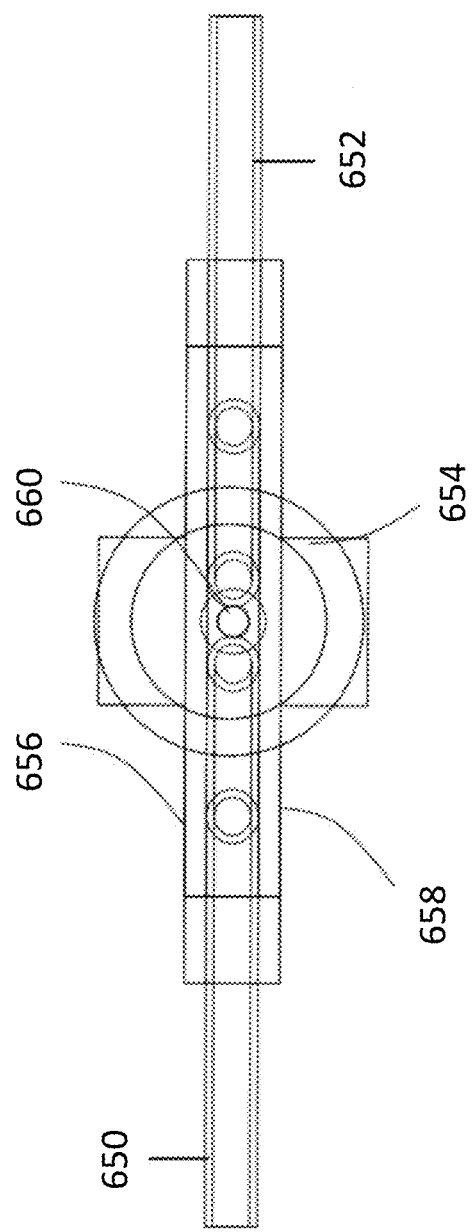
FIG. 36 illustrates an exemplary cross-sectional view (from the inlet) of a gliding arc plasma reactor.

FIG. 36 illustrates an exemplary cross-sectional view (from inlet) of a gliding arc plasma reactor that includes electrodes 650, 652, an air inlet 654, quartz plates 656, 658, and a nozzle 660. FIG. 36 illustrates a schematic diagram of an exemplary embodiment of an NO generating system. In some embodiments, the air flow is directed to the plasma reactor by a flow controller in the range of 0.05 to 6 slpm. The air flow glides the arc between the electrodes and the treated air which would be air enhanced nitric oxide would be obtained from the outlet. Quartz plates on one or more side of the plasma chamber enable visualization of the plasma and optical means of plasma detection and analysis. In some embodiments, light emitted from the plasma chamber is used to monitor and assess plasma performance. In some embodiments, the outlet of the plasma reactor is connected to a diluted airline controlled by an additional flow controller to keep the NO concentration of the gas below the highest capacity of the NO analyzer. In some embodiments, the concentration of the NO out of the plasma is the concentration of NO measured by analyzer times the dilution ratio. In some embodiments, the internal shape of the plasma chamber is designed to have a constant cross-section along the length of the chamber. This maintains a constant velocity of gas through the plasma chamber, facilitating modeling of the chamber performance and promoting event wear on the electrode surfaces.

Figure 37:
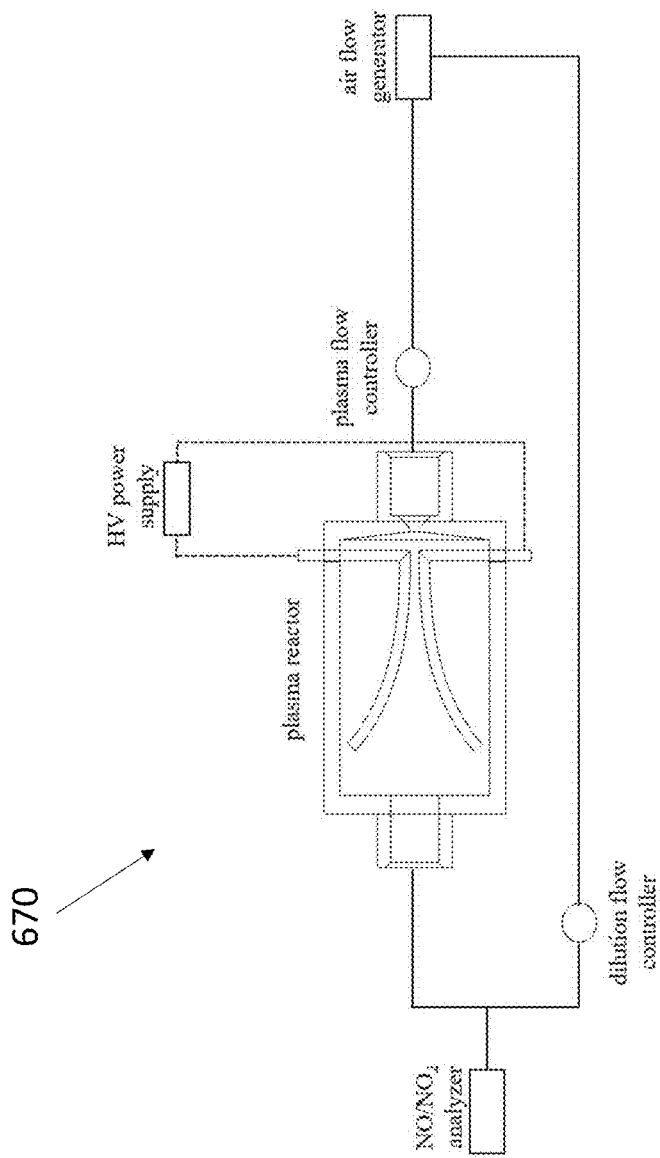
FIG. 37 illustrates an exemplary cross-sectional view of the gliding arc plasma reactor.

FIG. 37 illustrates a cross-sectional view of the gliding arc plasma reactor 670.

NO and $NO_2$ production are modulated by varying one or more of the power supply frequency (20-70 kHz), primary circuit voltage, second circuit voltage (i.e., across the plasma) (5-8 kV), duty cycle and plasma flow rate (0.05-6 slpm). In some embodiments, NO generation can be modulated by varying the impedance of the secondary circuit using a rheostat, or equivalent component, to vary the voltage across the plasma.

Figure 38:
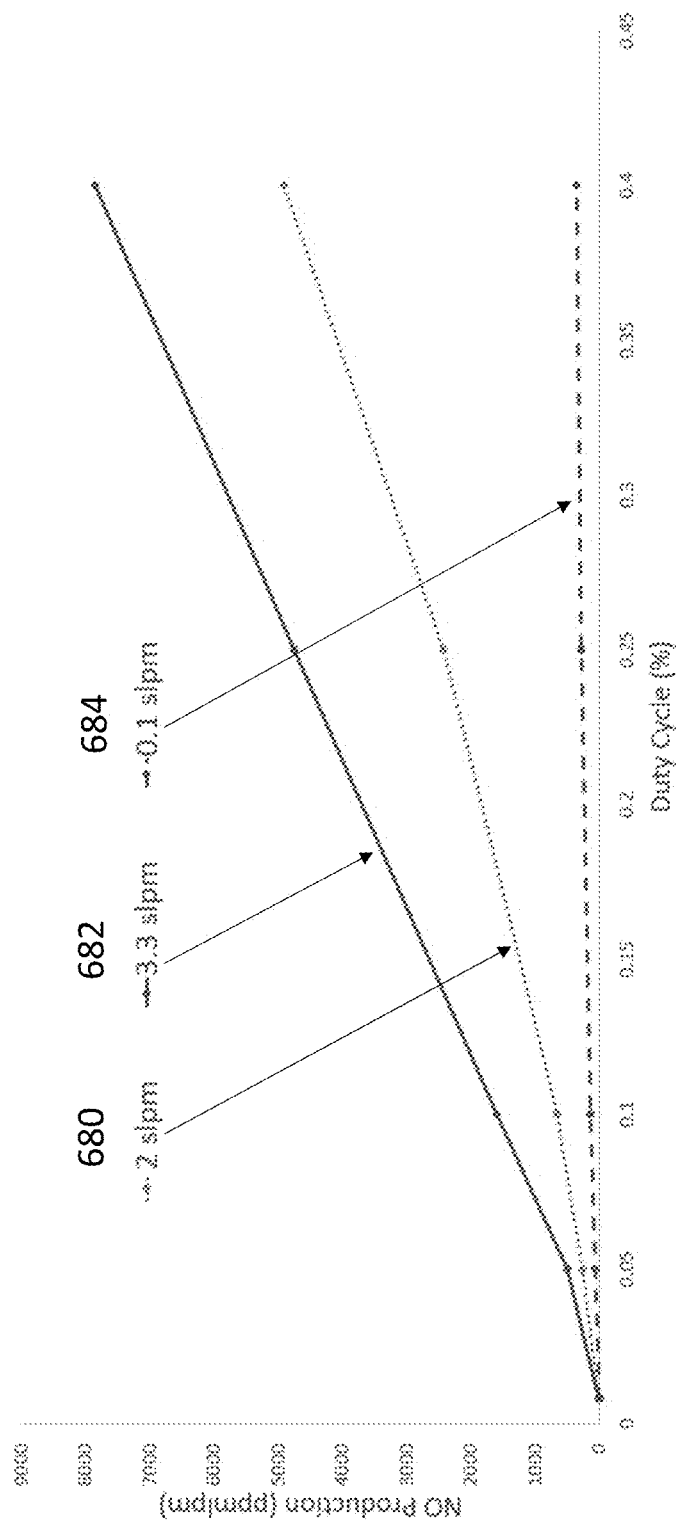
FIG. 38 illustrates an exemplary graph showing NO and $NO_2$ concentration and $NO/NO_2$ ratio versus power.

FIG. 38 illustrates an exemplary graph showing NO and $NO_2$ concentration and $NO/NO_2$ ratio versus power for various air flow rates (2 slpm air flow rate 680, 3.3 slpm air flow rate 682, and 0.1 slpm air flow rate 684). With increasing duty cycle, NO and $NO_2$ concentration increases as can be seen in FIG. 38. Enhancement of the power can make more high energy electrons to dissociate the nitrogen and oxygen molecules (thanks to the vibrational excitation of molecules due to the electrons impact) and increase the possibility of $NO/NO_2$ production. In addition, power enhancement enlarges the arc discharge gliding distance between the electrodes which can provide more residence time for the gas molecules to exist inside the plasma and increase the possibility of NO production.

Furthermore, the results in FIG. 38 indicate that the gliding arc can provide a large range of NO production from 2 to 8000 ppmlpm which is very desirable for treatment of hypoxic respiratory diseases. Respiratory applications often have variable flow rates to the patient, requiring NO production to vary as well. In some embodiments, NO production is linearly proportional to ventilator flow rates. These results demonstrate that a gliding arc design can produce a wide range of NO concentrations and production levels when regulated by the amount of power delivered to the plasma.

Figure 39:
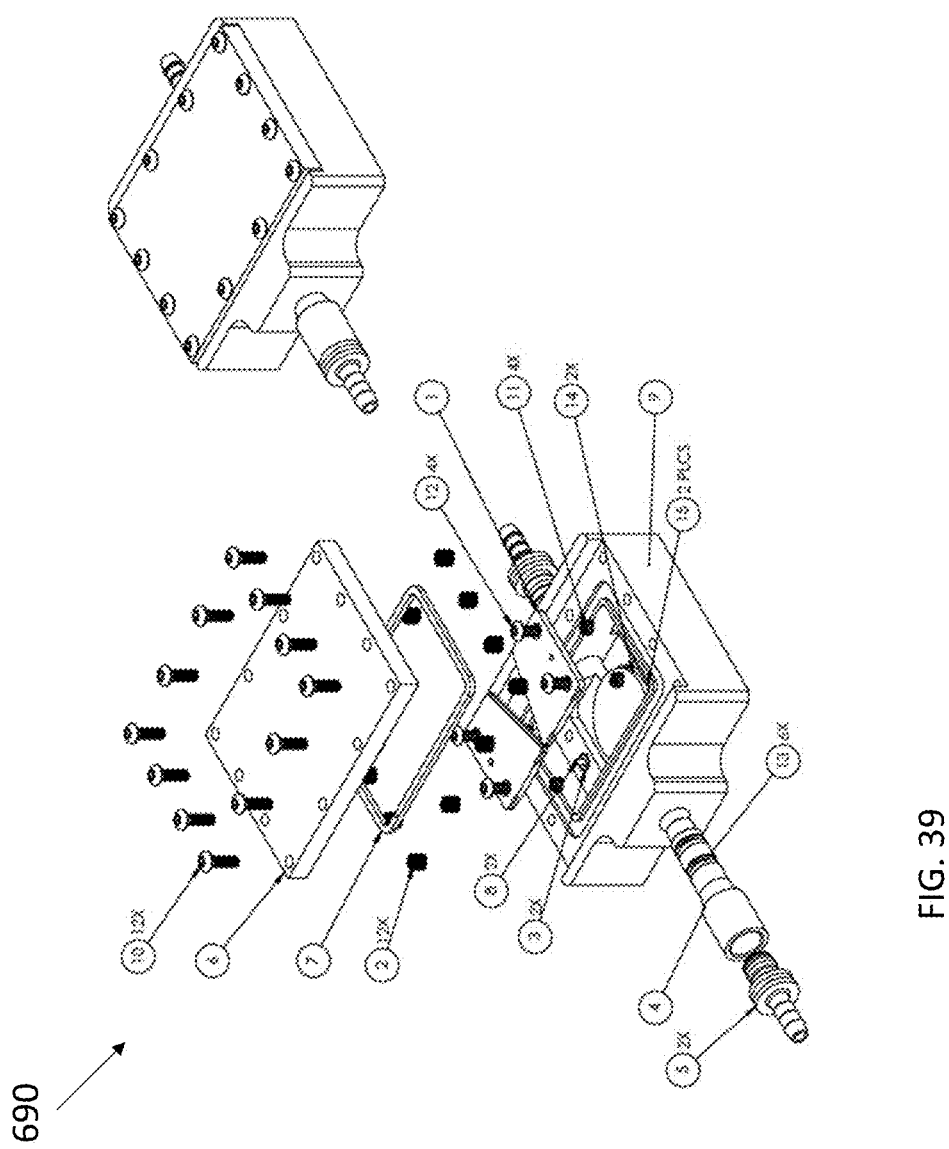
FIG. 39 is an exploded view of a gliding arc electrode chamber.

FIG. 39 depicts an embodiment of a modular gliding arc design constructed of a plasma chamber 690 with a cavity, triangular gliding arc electrodes, removable nozzle, a seal and a lid. The plasma chamber can be fabricated from high temperature polymers (PEEK), ceramic, or metal. In the event that a conductive material is used, such as metal, additional electrical isolation features are necessary to prevent shorting between electrodes. In this design, the tolerance stack-up between nozzle, chamber and electrode can significantly impact nozzle to gap alignment, thereby affecting NO production efficiency.

Figure 40:
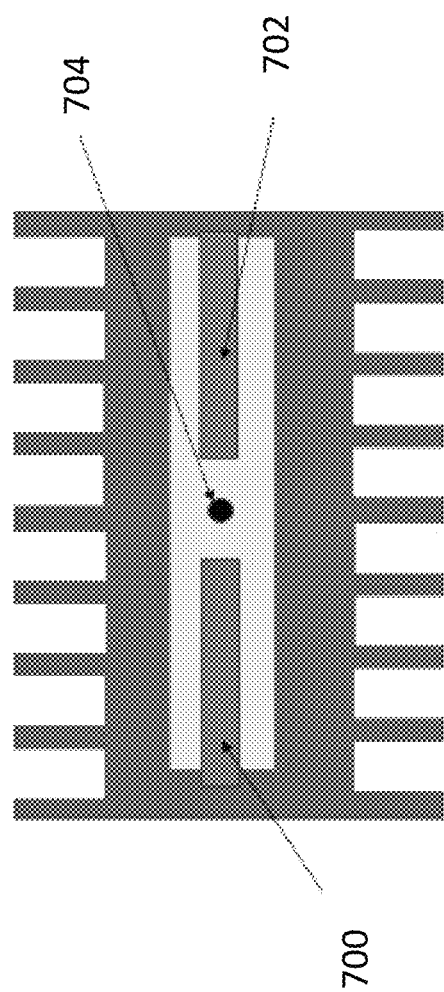
FIG. 40 is an exemplary view of a plasma chamber design that minimizes tolerance stack-up between the nozzle and electrodes.

FIG. 40 depicts an embodiment to an approach to fabricating a plasma chamber to minimize tolerance stack-up between a nozzle and an electrode gap. The chamber is split along a plane orthogonal to the direction of gas flow. The upstream half of the plasma chamber includes features to locate the electrodes 700, 702 and the nozzle 704.

Plasma Torch

Figures 41A, 41B:
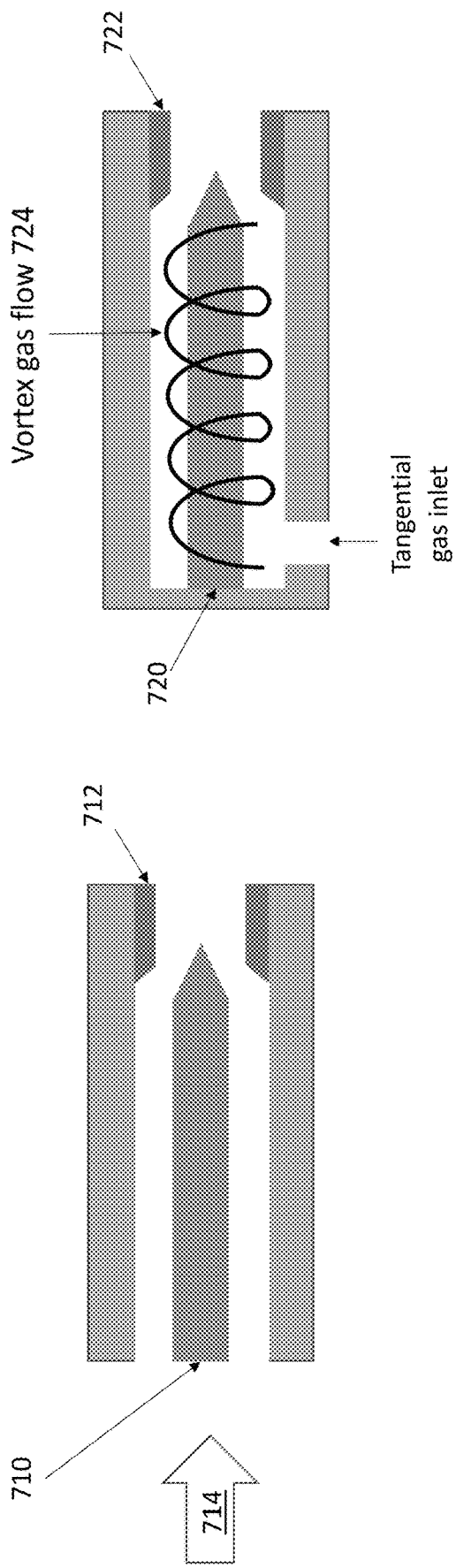
FIG. 41A and FIG. 41B are an exemplary embodiment of a plasma torch electrode configuration.

In some embodiments, a plasma torch electrode configuration as shown in FIG. 41A and FIG. 41B are utilized within an NO generation system. This approach offers a large electrode surface for electrode longevity, long creepage distance between electrodes with low probability of sputtering of Ir-oxide shorting the electrode, and passage of all reactant gas through the plasma zone. In one embodiment shown in FIG. 41A, reactant gas travels parallel to the center electrode 710. In some embodiments shown in FIG. 41B, reactant gas is introduced to the plasma chamber tangentially, creating a vortex flow within the chamber. A vortex/helical flow pattern increases reactant gas-plasma interaction. In both embodiments, a cylindrical center electrode 710, 720 is located within a tubular nozzle electrode 712, 722. Arcing occurs between electrodes, where the gap is minimum. When a reactant gas flow 714 is parallel to the electrodes, as in FIG. 41A, only a portion of the reactant gas passes through the electrical discharge. When gas flows in a vortex 724, as in FIG. 41B, gas flow can carry the arc discharge in a helical path, increasing the plasma-gas interaction and NO production in a given amount of reactant gas flow.

Diverging Electrode Plasma Torch

Figure 42:
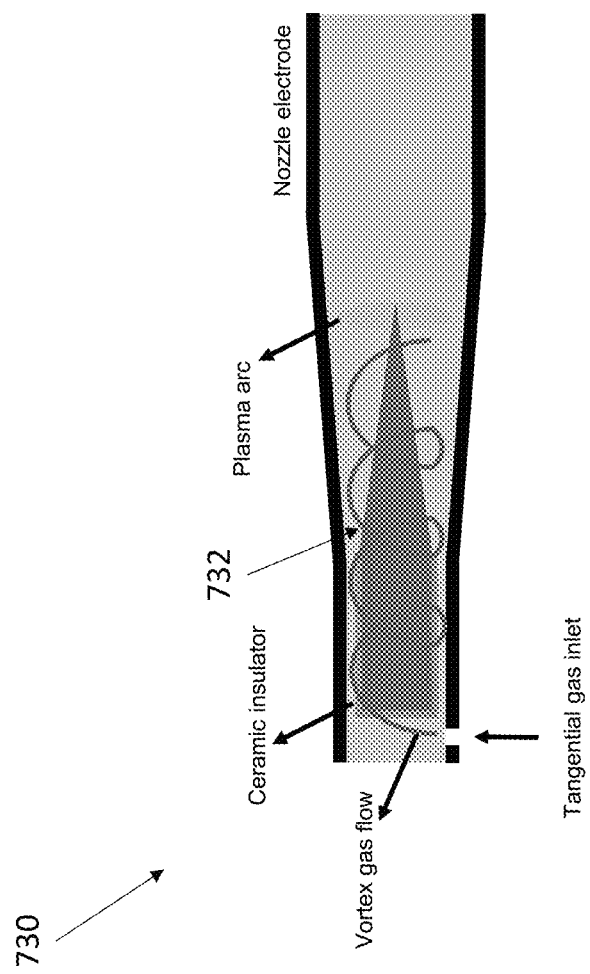
FIG. 42 is an exemplary embodiment of a plasma torch design with an increasing gap along the direction of reactant gas flow.

In some embodiments of an NO generator, the shape of the center electrode and nozzle electrode is such that the gap increases along the direction of reactant gas flow, as shown in FIG. 42. This design offers similar features to a plasma torch design with the addition of larger gaps for increased production and the traveling of arcs along the electrode surfaces to prolong electrode life and reduce electrode temperature. Gas-plasma interaction is greater in a diverging electrode plasma torch than in a gliding arc design, thereby increasing NO production efficiency.

Figure 43:
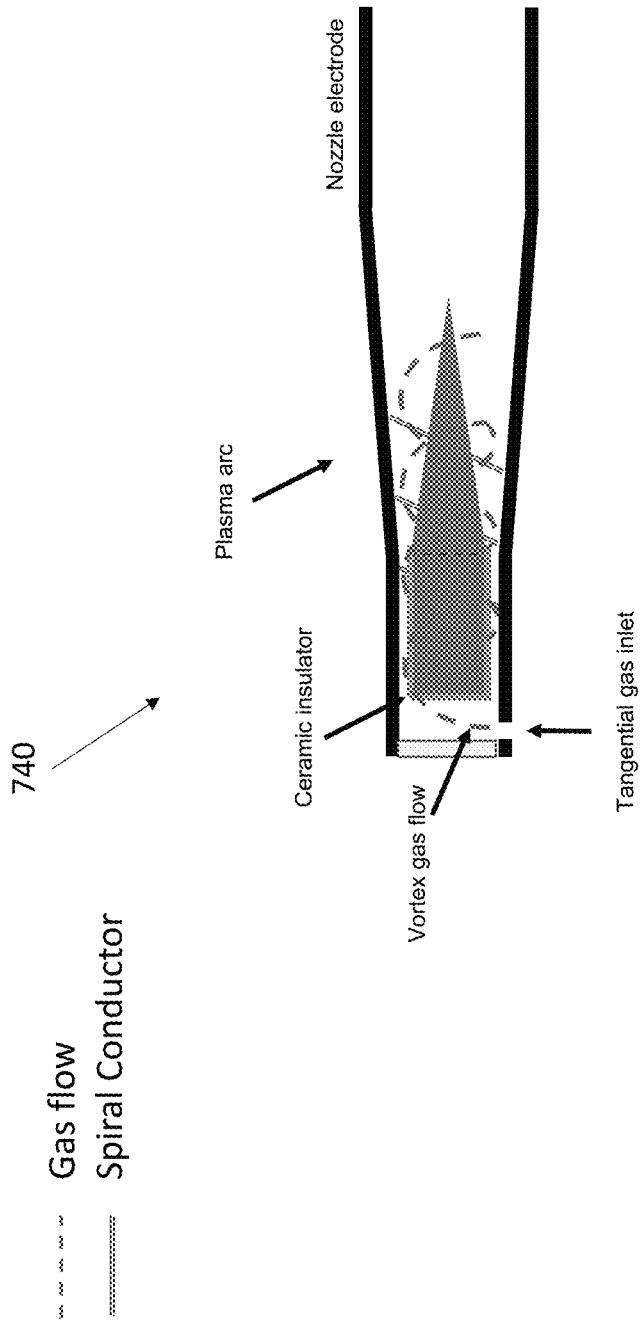
FIG. 43 is a cross-sectional view of an exemplary embodiment of a plasma torch design with helical outer conductive path.

A plasma torch design 730, as shown in FIG. 42 can present a complex phenomenon to model due to plasma and reactant gas flow traveling in three dimensions. In some embodiments, a nozzle contains a helical electrode 732 within it. Reactant gas flow is directed to travel parallel to the helix, thereby generating a predictable and consistent gas and plasma interaction. FIG. 43 depicts a cross-sectional view of a plasma torch design 740 with helical nozzle electrode. The helical electrode is shown as double lines along the wall of the chamber. In some embodiments, the electrode helix is continuous from the smallest gap region to a point beyond where the plasma can travel. Plasma travel is limited by parameters including, but not limited to voltage duty cycle, gas velocity, gap, electrode cleanliness, and voltage magnitude.

Gliding Opposed Electrode

Figure 44A:
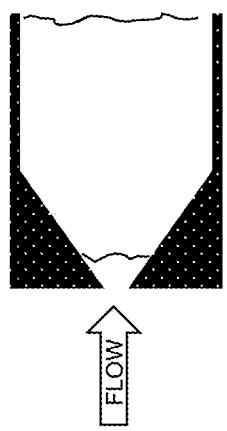
FIG. 44A and FIG. 44B illustrate an embodiment of a combination of a gliding arc and an opposed electrode.
Figure 44B:
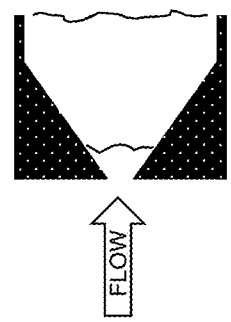

A combination of electrode concepts as shown in FIG. 44A and FIG. 44B can combine relative advantages of each electrode. FIG. 44A (a new electrode) and FIG. 44B (an older electrode) depict a combination of a gliding arc and an opposed electrode. The gliding arc portion of the electrode is upstream, so any arc initiated will move with the velocity downstream to where the slope becomes flat, eventually hanging at that location as long as the pulse is held. When the arc is gliding, the air velocity does not stretch the arc, but when the arc reaches the end of the electrodes, it will stretch, resulting in a plasma beam longer than the electrode gap at that point.

This combination system can yield greater efficiencies associated with larger plasma beam lengths, while only requiring minimal voltage to initiate associated with small gaps. In a NO generation system designed to run on batteries, or an NO system where set-point resolution requirements are less-demanding, such an electrode can be used.

Additionally, this electrode configuration can be used when NO production is controlled via current modulation, while the plasma beam is left on (i.e. not pulsed). This may further enhance the efficiency, as well as result in less $NO_2$ production associated with long-duration pulses and large gaps.

The straight section of the electrode may be intentionally low mass to promote erosion in a controlled manner.

Ring Cartridge

Figure 45B:
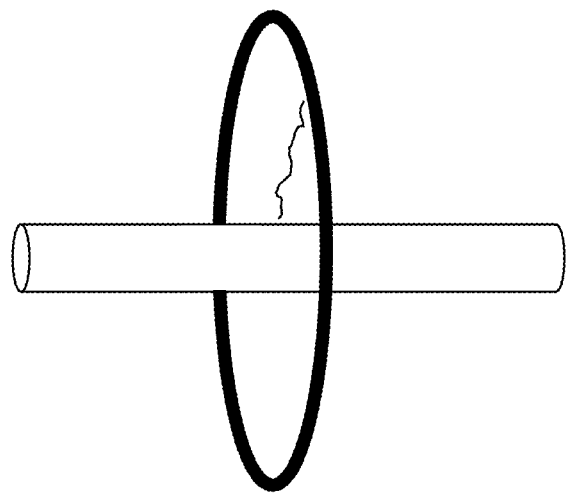
FIG. 45A and FIG. 45B illustrate an embodiment of an electrode ring cartridge.
Figure 45A:
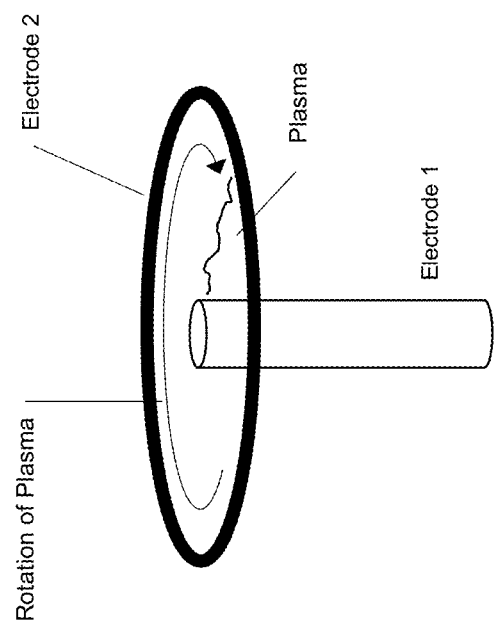

An electrode pair can be constructed from a rod and concentration ring, as shown in FIG. 45A and FIG. 45B. In some embodiments, the rod may have a cut edge aligned with the ring (FIG. 45A) so as to facilitate arcing with the concentrated field of the cut edge. In some embodiments, the rod ends may be substantially far away from the ring electrode; this will impose a higher starter voltage, but will not erode as fast.

Electrode Cartridge

Figure 46F:
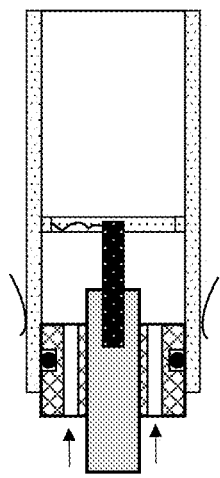
Figure 46E:
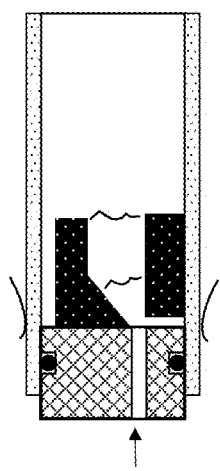

An electrode may be designed as a cartridge, such that a metal cylinder can contain electrode geometry (FIG. 46A, FIG. 46B, FIG. 46C, FIG. 46D, FIG. 46E, and FIG. 46F), including either an opposed electrode (FIG. 46B), a gliding arc (FIG. 46D), or some combination thereof (FIG. 46E). The metal cylinder can be high voltage, but in some embodiments can tie the cylinder electrode to circuit or earth ground. Grounding the cylinder can allow for the creation of an EMI cage and facilitating management of creepage and clearance distances. Additional benefits of the cartridge pertain to thermal management—manifolds and housings supporting most electrode concepts are inherently large or heavy, owing to use of dense ceramics and large creepage distances. A metal cylinder as the manifold is intrinsically heat resistant with generally similar temperatures to ceramics, but without the difficult manufacturing processes.

In some embodiments, the grounded electrode is a unibody construction with the metal cylinder to facilitate conductive heat transfer to reduce electrode erosion. This can be accomplished through an extrusion, welding a feature, or a casting.

An insulative body containing one electrode is inserted into the metal cylinder. The insulative body may have ridges to create adequate creepage & clearance distances within the cartridge. The insulative body must contain holes or create them upon insertion to the cylinder to allow air to pass through the cartridge.

In some embodiments, both electrodes are packaged within the cylinder to create one electrode cartridge (FIG. 46A). In some embodiments that would lean towards a consumable cartridge, the insulative body can be part of the permanent device (FIG. 46C, FIG. 46D, FIG. 46E, and FIG. 46F). In those consumable embodiments, the permanent electrode may be a corrosion resistant metal or alloy, while the other consumable electrode may be a more commodity metal which is not subjected to corrosion because of its replacement schedule. In some consumable embodiments, both electrodes and insulative body would be in the cartridge and therefore replaceable. Accordingly, both electrodes would be a more commodity metal. Additionally, a cylindrical electrode cartridge that inserts in a single direction, creating blind pneumatic and electrical connections inside of a controller, is well suited to being replaced by someone less skilled than a technician, such as a respiratory therapist or an end-user of an ambulatory device.

In some embodiments, a consumable cartridge may also contain a $NO_2$ scrubbing media immediately after the electrode pair (FIG. 46B).

Clinical Applications

Various therapies can be used with an NO generation device. In some embodiments, an NO generation and delivery device can be combined with a humidifier.

In some embodiments, an NO generation and delivery device is in the form of an ET tube. In some embodiments, the ET tube generates NO continuously with NO-containing gas entering and exiting the patient. In some embodiments, the system only generates NO as inspiratory gas enters the patient. The system can use a flow sensor to measure inspired gas and generate plasma accordingly. In some embodiments, the device pulses plasma constantly at an adjustable frequency and or duty cycle. The user can increase plasma activity to vary the dose In some clinical applications in home and/or in hospital, it can be advantageous to inhale NO for short intervals, periodically. In some embodiments, a patient inhales NO concentrations in excess of 80 ppm for several minutes, multiple times a day to treat or prevent pulmonary infection. In some embodiments, the range of inhaled NO concentration to prevent infection can be 100 to 300 ppm. NO delivery means for periodic dosing include but are not limited to an inhaler, an ambulatory device, a ventilator, an oxygen concentrator, and a NO tank. Treatments at high NO concentration can be based on elapsed time or clinical parameters, such as methemoglobin level. In some embodiments, a NO delivery system measures and/or receives methemoglobin readings and terminates a treatment when methemoglobin levels reach a threshold. In some embodiments, a NO delivery system can resume NO delivery when methemoglobin levels fall below a threshold.

In some clinical applications, a patient inhales NO on an as-needed basis. For example, after a short walk, ascending a flight of stairs, when their $SpO_2$ is low, when $O_2$ needs are high. In some embodiments, a NO delivery device permits the patient to select a dose within a pre-determined range. In some embodiments, a NO delivery device limits the amount of NO a patient can inhale over a period of time.

There are also a variety of clinical applications of inhaled NO in a hospital/clinical setting. Clinical applications include but are not limited to respiratory failure of prematurity, bronchopulmonary dysplasia (infants), serious lung infection, respiratory failure in the intensive care unit (PCU) or pediatric intensive care unit (PICU), heart surgery, acute iNO testing in pulmonary hypertension (PH) or chronic pulmonary hypertension (e.g. PAH), cardiac surgery in the USA, acute respiratory distress syndrome, cardiopulmonary resuscitation, cardiopulmonary bypass prevention of renal injury, acute stroke and traumatic brain injury, and acute ST-Elevation myocardial infarction (STEMI).

In some embodiments, a clinical application can include the prevention and/or treatment of ventilator associated pneumonia. NO is an anti-infective agent currently being explored in cystic fibrosis (CF) for mycobacterial infections and bacterial infections, e.g pseudomonas. It can be used with prolonged ventilated patients to reduce ventilator associated pneumonia.

In some embodiments, a clinical application can include periodically dosing a patient with NO to prevent ventilator associated pneumonia. In some embodiments, a ventilator that generates NO periodically doses a patient to prevent ventilator associated pneumonia.

In some embodiments, a clinical application can include Acute Right Heart Failure (diverse etiology) including pulmonary embolism. In this application, NO decreasing the pulmonary resistance, thereby offloading the right heart.

In some embodiments, a clinical application can include Administration with hemoglobin oxygen carriers and stored blood. Hemoglobin-based oxygen carriers (HBOCs) or hemoglobin based oxygen carrying solutions (HBOCs) can cause scavenging of NO and systemic and pulmonary vasoconstriction inhibited by iNO. Hemolyzed blood scavenges NO leading to systemic and pulmonary vasoconstriction.

There are also a variety of clinical applications of inhaled NO in an ambulatory setting, including the following:
- WHO Group 1 PAH—Potential to subtype e.g. idiopathic, familial etc., pediatric PAH, and PAH during pregnancy (avoids toxicity from PAH drugs)
- WHO group 2 PAH—Selected well-controlled patients with left heart failure (risk of pulmonary edema, and LVAD recipients with right heart disease (RHD) and pulmonary hypertension (PH) (Orphan)
- WHO group 3 PH—PH-ILD or subtype ILD e.g. IPF, CT-related ILD, cHP, etc., PH-COPD, and Combined pulmonary fibrosis emphysema (CPFE)
- WHO group 4 Chronic Thromboembolic PH (CTEPH)— Improve right heart disease (RHD)
- Sarcoidosis
- Right heart dysfunction, diverse etiology—Afterload reduction even in absence of pulmonary hypertension (PH), and Etiologies include ischemic heart disease, valvular disease etc.
- Infectious diseases, such as cystic fibrosis e.g. pseudomonas, B. Cepacia, NTM, Multiple Drug-resistant tuberculosis, Non-tuberculous mycobacterial infection (NTM), and Bronchiectasis Bridge to lung and/or heart transplant—Addresses pulmonary hypertension (PH), oxygenation, RVD etc Post lung and. or heart transplant—Reduces pulmonary vascular resistance and contributes to the prevention of bacterial infections High altitude medicine—To address mountain sickness, High altitude pulmonary edema (HAPE), and reduce hypoxic pulmonary vasoconstriction Military field applications, such as inhalation injury, cardiopulmonary resuscitation/shock, and High-altitude sickness including during flight Cardiopulmonary Resuscitation—reverses acute PH due to pulmonary vasoconstriction increasing cardiac output (compressions)

With stored blood or hemoglobin oxygen carriers to prevent complications

During cardiopulmonary bypass to prevent complications

With ECMO to reduce the use of heparin

All publications, patent applications and patents mentioned herein are hereby incorporated by reference in their entirety as if each individual publication or patent was specifically and individually indicated to be incorporated by reference. Reference is made to U.S. application Ser. No. 15/907,241, filed Feb. 27, 2018, U.S. application Ser. No. 16/388,464, filed Apr. 18, 2019, U.S. application Ser. No. 16/697,498, filed Nov. 27, 2019, U.S. application Ser. No. 15/907,258, filed on Feb. 27, 2018, U.S. application Ser. No. 16/363,505, filed Mar. 25, 2019 and U.S. application Ser. No. 16/724,233, filed Dec. 21, 2019 which are hereby incorporated by reference in their entireties.

What is claimed is:

1. A nitric oxide (NO) generation system, comprising:
   at least one pair of electrodes configured to generate a product gas containing NO from a flow of a reactant gas, the at least one pair of electrodes having a first end and second end with a length therebetween such that a plasma produced is carried by the flow of the reactant gas and glides along the length of the at least one pair of electrodes from the first end towards the second end;
   a controller configured to regulate the amount of nitric oxide in the product gas produced by the at least one pair of electrodes using one or more parameters as an input to the controller, the one or more parameters including information from a plurality of sensors configured to collect information relating to at least one of the reactant gas, the product gas, and a medical gas into which the product gas flows, and
   one or more nozzles positioned to direct the flow of reactant gas in the area around the least one pair of electrodes, the one or more nozzles having a size, location, and orientation in relation the at least one pair of electrodes to achieve a reactant gas velocity to control the rate of plasma arc travel along the at least one pair of electrodes and an amount of plasma arc bending for a given reactant gas flow rate;
   wherein the controller is configured to control at least a duty cycle of a voltage applied to the at least one pair of electrodes to control a distance along the electrodes which a discharge travels to control the amount of NO in the product gas.

2. The nitric oxide (NO) generation system of claim 1, wherein the at least one pair of electrodes is formed from a material selected from the group consisting of hafnium, glassy carbon, iridium, rhodium, platinum, graphite, carbon-carbon composite, steel, stainless steel, titanium, copper, nickel, tungsten-silver alloy, tungsten, and alloys thereof.

3. The nitric oxide (NO) generation system of claim 1, wherein more than one material is used to form at least one of the electrodes in the at least one pair of electrodes along an edge thereof.

4. The nitric oxide (NO) generation system of claim 1, wherein the electrodes in the at least pair of electrodes diverge from one another such that the electrodes move away from each along their length from the first end to the second end.

5. The nitric oxide (NO) generation system of claim 4, wherein the diverging electrodes form a gap at the first end in a range of about 0.05 mm to about 10 mm.

6. The nitric oxide (NO) generation system of claim 4, wherein the diverging electrodes form a gap at the second end in a range of about 1 mm to about 100 mm.

7. The nitric oxide (NO) generation system of claim 1, wherein a distance the plasma glides along the length of the electrodes ranges from 1 mm to 200 mm.

8. The nitric oxide (NO) generation system of claim 4, wherein the angle between the electrodes in the at least one electrode pair is between about 0 and about 75 degrees.

9. The nitric oxide (NO) generation system of claim 1, wherein the nozzle ranges in diameter from about 0.1 mm to about 15 mm.

10. The nitric oxide (NO) generation system of claim 1, wherein a cross-sectional area of the nozzle ranges from 0.03 mm$^2$ to 707 mm$^2$.

11. The NO generation system of claim 1, wherein a cross-sectional area of the nozzle can be varied by the NO generation system.

12. The nitric oxide (NO) generation system of claim 8, wherein the reactant gas flow along the electrode surfaces ranges in velocity from about 0 to about 100 m/second.

13. The nitric oxide (NO) generation system of claim 1, wherein a shape of an edge of the electrodes in the at least one electrode pair are configured to increase the length of an arc at a specific rate for a specific flow rate of reactant gas.

14. A nitric oxide (NO) generation system, comprising:
    a plasma chamber comprising:
       at least one pair of electrodes configured to generate a product gas containing NO from a flow of a reactant gas, the at least one pair of electrodes having a first end and a second end with a length therebetween such that a plasma produced is carried by the flow of the reactant gas and glides along the length of the at least one pair of electrodes from the first end towards the second end; and
       at least one nozzle through which the reactant gas flows into the plasma chamber to the at least one pair of electrodes, the one or more nozzles having at least one of a location and orientation in relation the at least one pair of electrodes to achieve a reactant gas velocity to control the rate of plasma arc travel along the at least one pair of electrodes and an amount of plasma arc bending for a given reactant gas flow rate; and
    a controller configured to regulate the amount of nitric oxide in the product gas by the at least one pair of electrodes using one or more parameters as an input to the controller, the one or more parameters including information from a plurality of sensors configured to collect information relating to at least one of the reactant gas, the product gas, and a medical gas into which the product gas flows,
    wherein the controller is configured to control at least a duty cycle of a voltage applied to the at least one pair of electrodes to control a distance along the electrodes which a discharge travels to control the amount of NO in the product gas.

15. The nitric oxide (NO) generation system of claim 14, wherein a shape of an edge of the electrodes in the at least one electrode pair are configured to increase the length of an arc at a specific rate for a specific flow rate of reactant gas.

16. The nitric oxide (NO) generation system of claim 14, wherein the plasma chamber is formed from a material selected from the group consisting of a high temperature polymer, ceramic, glass, quartz, metal, coated metal, and composite materials.

17. The nitric oxide (NO) generation system of claim 14, wherein the at least one nozzle comprises a first nozzle configured to supply reactant NO gas to the at least one pair of electrodes and a second nozzle configured to cool the plasma chamber.

18. The nitric oxide (NO) generation system of claim 14, wherein the at least one nozzle comprises a first nozzle configure to supply reactant gas to the at least one pair of electrodes and a second nozzle configured to vary an interaction between the plasma and the reactant gas.

* * * * *